US012703876B2

(12) United States Patent
Hauptmann et al.

(10) Patent No.: US 12,703,876 B2
(45) Date of Patent: Aug. 11, 2026

(54) METHOD FOR REDUCING MISINCORPORATION OF NON-CANONICAL BRANCHED-CHAIN AMINO ACIDS

(71) Applicants: SANOFI AVENTIS DEUTSCHLAND GMBH, Frankfurt am Main (DE); TECHNISCHE UNIVERSITÄT BERLIN, Berlin (DE)

(72) Inventors: Peter Hauptmann, Frankfurt am Main (DE); Angel Corcoles Garcia, Frankfurt am Main (DE); Claus Tobias Lattemann, Frankfurt am Main (DE); Arne Matzen, Frankfurt am Main (DE); Peter Neubauer, Berlin (DE)

(73) Assignees: SANOFI-AVENTIS DEUTSCHLAND GMBH (DE); TECHNISCHE UNIVERSITÄT BERLIN (DE)

( * ) Notice: Subject to any disclaimer, the term of this patent is extended or adjusted under 35 U.S.C. 154(b) by 112 days.

(21) Appl. No.: 17/416,308

(22) PCT Filed: Dec. 10, 2019

(86) PCT No.: PCT/EP2019/084504
§ 371 (c)(1),
(2) Date: Jun. 18, 2021

(87) PCT Pub. No.: WO2020/126700
PCT Pub. Date: Jun. 25, 2020

(65) Prior Publication Data

US 2022/0064692 A1 Mar. 3, 2022

(30) Foreign Application Priority Data

Dec. 20, 2018 (EP) .................................... 18214562

(51) Int. Cl.

| | |
|---|---|
| ***C12P 21/02*** | (2006.01) |
| ***A61K 38/28*** | (2006.01) |
| ***C07K 14/62*** | (2006.01) |
| ***C12N 9/02*** | (2006.01) |
| ***C12N 9/10*** | (2006.01) |
| ***C12N 9/12*** | (2006.01) |
| ***C12P 13/06*** | (2006.01) |

(52) U.S. Cl.
CPC ............. *C12P 21/02* (2013.01); *C07K 14/62* (2013.01); *C12Y 101/01086* (2013.01); *C12Y 202/01006* (2013.01); *C12Y 207/02004* (2013.01); *C12Y 403/01009* (2013.01)

(58) Field of Classification Search
None
See application file for complete search history.

(56) References Cited

U.S. PATENT DOCUMENTS

2016/0244765 A1 8/2016 Khvorova et al.

FOREIGN PATENT DOCUMENTS

| | | | | |
|---|---|---|---|---|
| KR | 10-1844452 B1 | 5/2018 | | |
| RU | 2495131 C2 | 10/2013 | | |
| WO | WO 2005/038017 A2 | 4/2005 | | |
| WO | WO-2007103521 A2 * | 9/2007 | ............... | C12N 1/20 |
| WO | WO 2009/104199 A1 | 8/2009 | | |

OTHER PUBLICATIONS

Hashiguchi et al., Biosci. Biotechnol. Biochem. 63:672-679, 1999 (Year: 1999).*
Eisenstein, E., J. Biol. Chem. 266:5801-5807, 1991 (Year: 1991).*
Veeravalli et al., Biotechnol. Prog. 31:204-211, 2015 (Year: 2015).*
Deliverable D3.12: Validating the methodology to investigate oscillation effects on product quality, Feb. 26, 2017, 15 pages (Year: 2017).*
Fisher et al., PLoS ONE 6:e15364, 2011, 9 pages (Year: 2011).*
Gu et al., Microb. Cell. Fact. 16:167, 2017, 8 pages (Year: 2017).*
Apostol et al., J. Biol. Chem. 272:28980-28988, 1997 (Year: 1997).*
Ning et al., Metabolic Engineering 36:10-18, 2016 (Year: 2016).*
Gardner et al., Nature 403:339-342, 2000 (Year: 2000).*
Gupta et al., Nat. Biotechnol. 35:273-279, 2017 (Year: 2017).*
Janes et al., J. Bacteriol. 18:2709-2714, 2001 (Year: 2001).*
Pezo et al., PNAS 101:8593-8597, 2004 (Year: 2004).*
Apostol et al., Incorporation of norvaline at leucine positions in recombinant human hemoglobin expressed in *Escherichia coli*. Journal of Biological Chemistry, 1997, 272(46): 28980-28988.
Baba et al., "Construction of *Escherichia coli* K-12 in-frame, single-gene knockout mutants: the Keio collection", Molecular Systems Biology, 2006, 2: 2006.0008.
Bogosian et al., "Biosynthesis and incorporation into protein of norleucine by *Escherichia coli*", Journal of Biological Chemistry, Jan. 5, 1989, 264(1): 531-539.
Cvetesic et al., "Proteome-wide measurement of non-canonical bacterial mistranslation by quantitative mass spectrometry of protein modifications", Scientific Reports, 2016, 6: 28631.

(Continued)

*Primary Examiner* — David Steadman
(74) *Attorney, Agent, or Firm* — LATHROP GPM LLP; James H. Velema, Esq.

(57) ABSTRACT

The present invention relates to a method for producing a recombinant polypeptide of interest in a microbial host cell, comprising (a) introducing a polynucleotide encoding the polypeptide of interest into a microbial host cell which has been modified such that an enzymatic activity selected from the group consisting of ketol-acid reductoisomerase (NADP (+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase activity (EC 4.3.1.19) is modulated in said microbial host cell as compared to the enzymatic activity in an unmodified microbial host cell, and (b) expressing said polypeptide of interest in said microbial host cell. Moreover, the present invention relates to a method for reducing misincorporation of at least one non-canonical branched-chain amino acid into a recombinant polypeptide of interest expressed in a microbial host cell.

7 Claims, 12 Drawing Sheets

Figure 1:
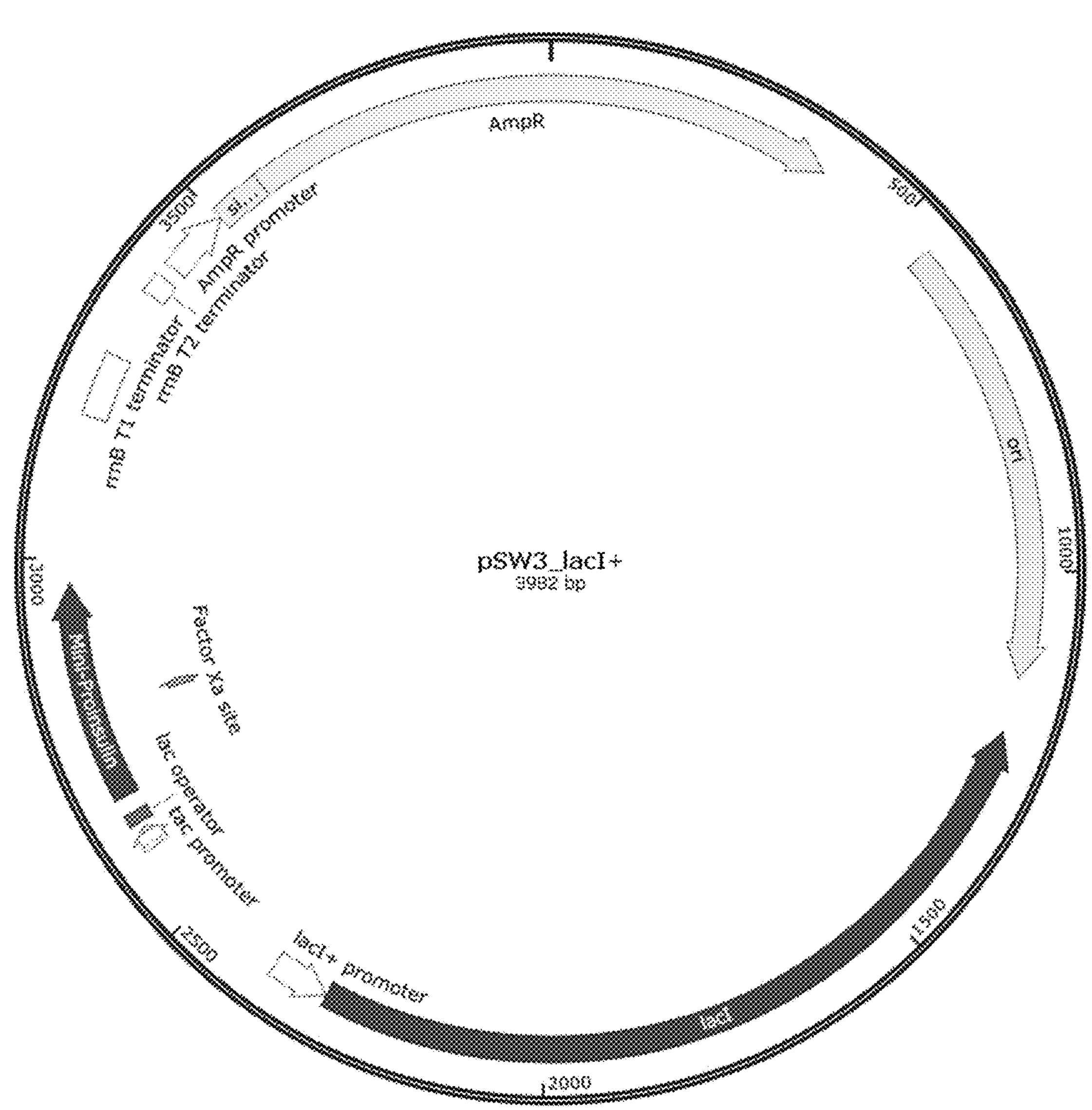

Specification includes a Sequence Listing.

(56) References Cited

OTHER PUBLICATIONS

Datsenko et al.,. "One-step inactivation of chromosomal genes in *Escherichia coli* K-12 using PCR products", PNAS USA, Jun. 2000, 97(12), 6640-6645.
Didiot et al., "Exosome-mediated Delivery of Hydrophobically Modified siRNA for Huntingtin mRNA Silencing", Mol Ther. Oct. 2016, 24(10):1836-1847.
Enfors et al., "Physiological responses to mixing in large scale bioreactors. Journal of biotechnology", Feb. 13, 2001, 85(2): 175-185.
Extended European Search Report for European Application No. 19792271.9, mailed Jul. 11, 2022.
Franco et al., "Bacterial Branched-Chain Amino Acid Biosynthesis: Structures, Mechanisms, and Drugability", Biochemistry, Oct. 23, 2017, 56(44): 5849-5865.
Grenier, "Complete Genome Sequence of *Escheria coli* BW25113", Genome Announcements, Sep./Oct. 2014, 2(5): e01038-14.
Guzman et al., "Tight regulation, modulation, and high-level expression by vectors containing the arabinose PBAD promoter", Journal of Bacteriology, Jul. 1995, 177(14): 4121-4130.
Haraszti et al., "High-resolution proteomic and lipidomic analysis of exosomes and microvesicles from different cell sources", J Extracell Vesicles, Nov. 17, 2016, 5: 32570.
Harris et al., "Amino acid misincorporation in recombinant biopharmaceutical products", Current Opinion in Biotechnology, Dec. 2014, 30: 45-50.
International Search Report & Written Opinion for PCT International Patent Application No. PCT/EP2019/084504 mailed Mar. 2, 2020.
Kiick et al., "Identification of an expanded set of translationally active methionine analogues in *Escherichia coli*", Jul. 27, 2001, FEBS Letters, 502(1-2), 25-30.
Lawther et al., "Molecular basis of valine resistance in *Escherichia coli* K-12", PNAS USA, Feb. 1981, 78(2): 922-925.
Martinis et al, "Non-standard amino acid recognition by *Escherichia coli* leucyl-tRNA synthetase", Nucleic Acids Symp Ser., 1997, 36: 125-128.
Megerle et al, "Timing and dynamics of single cell gene expression in the arabinose utilization system", Biophysical Journal, Aug. 2008, 95(4): 2103-2115.
Min et al., "Insulin related compounds and identification", Journal of Chromatography B Analyt Technol Biomed Life Sci, Nov. 1, 2012, 908: 105-112.
Muramatsu et al., "Finding of an isoleucine derivative of a recombinant protein for pharmaceutical use", Journal of Pharmaceutical and Biomedical Analysis, Apr. 1, 2003, 31(5): 979-987.
Parekh et al., "Growth rate-related regulation of the ilvGMEDA operon of *Escherichia coli* K-12 is a consequence of the polar frameshift mutation in the ilvG gene of this strain", Journal of Bacteriology, Mar. 1997, 179(6): 2086-2088.
Park et al., "Fermentative production of branched chain amino acids: a focus on metabolic engineering", Applied Microbiology and Biotechnology, Jan. 2010, 85(3): 491-506.
Reitz et al., "Synthesis of non-canonical branched-chain amino acids in *Escherichia coli* and approaches to avoid their incorporation into recombinant proteins", Curr Opin Biotechnol., Oct. 2018, 53: 248-253.
Schleif, "Regulation of the L-arabinose operon of *Escherichia coli*," Trends in Genetics, Dec. 2000, 16(12): 559-565.
Schweder, "Monitoring of genes that respond to process-related stress in large-scale bioprocesses", Biotechnology and Bioengineering, Oct. 20, 1999, 65(2): 151-159.
Soini et al, "Norvaline is accumulated after a down-shift of oxygen in *Escherichia coli* W3110", Microb. Cell Fact., Oct. 21, 2008, 7: 30.
Soini et al., "Accumulation of amino acids deriving from pyruvate in *Escherichia coli* W3110 during fed-batch cultivation in a two-compartment scale-down bioreactor, Advances in Bioscience and Biotechnology", Oct. 2011, 2(5): 336-339.
Sycheva et al., "Overproduction of noncanonical amino acids by *Escherichia coli* cells", Microbiology, Nov.-Dec. 2007, 76(6): 712-718.
Tsai et al., "Control of misincorporation of de novo synthesized norleucine into recombinant interleukin-2 in *E. coli*", Biochemical and Biophysical Research Communications, Oct. 31, 1988, 156(2): 733-739.
Wubbolts et al. "Proteomic and biochemical analyses of human B cell-derived exosomes. Potential implications for their function and multivesicular body formation", J Biol Chem., Mar. 28, 2003, 278(13): 10963-10972.
Bogosian et al., "Biosynthesis and Incorporation into Protein of Norleucine by *Escherichia coli*", The Journal of Biological Chemistry, 1989, 264(1): 531-539.
Efimov et al., "Synthesis of Human Proinsulin in *Escherichia coli* Cells", Aug. 1989, Bioorg. Khim., 15(8): 1078-1090. (Article in Russian with English Abstract).
Franco et al., "Bacterial Branched-Chain Amino Acid Biosynthesis: Structures, Mechanisms, and Drugability", Biochemistry, Nov. 2017, 56(44): 5849-5865.
Park et al., "Fermentative production of branched chain amino acids: a focus on metabolic engineering", Appl. Microbiol. Biotechnol., 2010, 85: 491-506.
Reitz et al., "Synthesis of non-canonical branched-chain amino acids in *Escherichia coli* and approaches to avoid their incorporation into recombinant proteins", Current Opinion in Biotechnology, 2018, 53: 248-253.
Soini et al., "Norvaline is accumulated after a down-shift of oxygen in *Escherichia coli* W3110", Microbial Cell Factories, Oct. 2008, 7(30): 14 pages.
Stokes et al., "Sequential Immunoaffinity Purification of Post-Translationally Modified Peptides for Improved Enrichment Specificity", Cell Signaling Technology, 2016 ASMS Poster Presentation.
Sycheva et al., "Overproduction of Noncanonical Amino Acids by *Escherichia coli* Cells", Microbiology, 2007, 76(6): 712-718.
Tapia et al., "Bioreactors for high cell density and continuous multi-stage cultivations: options for process intensification in cell culture-based viral vaccine production", Appl. Microbiol. Biotechnol., 2016, 100(5): 2121-2132.
Berry et al., "Substitution of cysteine for selenocysteine in type I iodothyronine deiodinase reduces the catalytic efficiency of the protein but enhances its translation", Endocrinology, 1992, 131(4): 1848-1852.
Gasser et al., "Antibody production with yeasts and filamentous fungi: on the road to large scale?", Biotechnol Letters, Feb. 2007, 29(2): 201-212.
Blombach et al., "L-Valine Production with Pyruvate Dehydrogenase Complex-Deficient Corynebacterium glutamicum", Applied and Environmental Microbiology, Apr. 2007, 73(7): 2079-2084.
Wikipedia, Beta-lactamse, obtained from url: <https://en.wikipedia.org/wiki/Beta-lactamase>, originally retrieved Nov. 27, 2025.

* cited by examiner

METHOD FOR REDUCING MISINCORPORATION OF NON-CANONICAL BRANCHED-CHAIN AMINO ACIDS

RELATED APPLICATIONS

This application is a 35 U.S.C. § 371 filing of International Patent Application No. PCT/EP2019/084504, filed Dec. 10, 2019, which claims priority to European Patent Application No. 18214562.3, filed Dec. 20, 2018, the entire disclosures of which are hereby incorporated herein by reference.

SEQUENCE LISTING

The instant application contains a Sequence Listing which has been submitted electronically in ASCII format and is hereby incorporated by reference in its entirety. Said ASCII file, created on Jun. 18, 2021, is named 719118_SA9-311US_ST25.txt and is 108,823 bytes in size.

DESCRIPTION

The present invention relates to a method for producing a recombinant polypeptide of interest in a microbial host cell, comprising (a) introducing a polynucleotide encoding the polypeptide of interest into a microbial host cell which has been modified such that an enzymatic activity selected from the group consisting of ketol-acid reductoisomerase (NADP (+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase activity (EC 4.3.1.19) is modulated (such as increased) in said microbial host cell as compared to the enzymatic activity in an unmodified microbial host cell, and (b) expressing said polypeptide of interest in said microbial host cell. Moreover, the present invention relates to a method for reducing misincorporation of at least one non-canonical branched-chain amino acid into a recombinant polypeptide of interest expressed in a microbial host cell. Further envisaged by the present invention is a microbial host cell comprising (a) a recombinant polynucleotide encoding a polypeptide of interest, and (b) a recombinant polynucleotide encoding a polypeptide having an enzymatic activity.

BACKGROUND OF THE INVENTION

Expression of recombinant proteins in microbial hosts such as *Escherichia coli* (*E. coli*) has become a standard technique for the manufacturing of recombinant therapeutic proteins such as insulin. Today, a variety of biopharmaceutical products produced by microbial cells such as *E. coli* are on the market.

However, overexpression of recombinant proteins is known to cause stress to the microbial host, often resulting in misfolding of proteins or incorporation of non-wanted amino acids. Altered proteins may display unwanted properties such as modified biological activity, increased sensitivity to proteolysis or immunogenicity. In particular, the misincorporation of amino acids into recombinant proteins is a problem, since pharmaceutical products such as recombinant insulin have to be homogenous and pure. As a result, recombinant proteins comprising misincorporated amino acids have to be removed from the product.

Branched-chain amino acids (BCAAs) are amino acids with a non-linear molecular structure. BCAAs have aliphatic side-chains with a branch, i.e. a central carbon atom is bound to three or more carbon atoms. Leucine, isoleucine and valine are so called proteinogenic or canonical BCAA. Besides the canonical BCAAs, non-canonical or non-proteinogenic BCAAs also exist. Such non-canonical BCAAs (ncBCAAs) are norleucine, norvaline, homoisoleucine and β-methylnorleucine.

Non-canonical branched chain amino acids (ncBCAA) such as norleucine and norvaline have been reported to be respectively misincorporated in place of leucine and methionine in recombinant proteins expressed in *E. coli* (Apostol I. et al., 1997, Incorporation of norvaline at leucine positions in recombinant human hemoglobin expressed in *Escherichia coli*. Journal of Biological Chemistry 272.46:28980-28988; Tsai et al., (1988), Control of misincorporation of de novo synthesized norleucine into recombinant interleukin-2 in *E. coli*. Biochemical and biophysical research communications 156 (2): 733-739). Synthesis and accumulation of ncBCAA is a result of the low specificity of the leu and ilv-operon-coded enzymes involved in the BCAA biosynthetic pathway for α-ketoacids. Several studies have shown that the enzymes of the leucine biosynthetic pathway, encoded by the leuABCD operon, are crucial for the production of non-canonical branched chain amino acids such as norleucine. In their canonical mode, the enzymes of the leucine pathway convert α-ketoisovalerate to α-ketoisocaproate; meaning that they cause a one carbon addition to a five carbon α-ketoacid. Moreover, the leucine biosynthetic pathway was also shown to display quite broad substrate specificity and its enzymes can act on a variety of α-ketoacids. For example, enzymes of the leucine pathway can also convert α-ketovalerate to α-ketocaproate, which is the precursor of norleucine.

Non-canonical branched chain amino acids (ncBCAA) misincorporation into nascent recombinant proteins happens due to promiscuity of amino-acyl tRNA synthetases (aaRS). The fidelity of protein synthesis counts on the aptitude of aaRSs to charge the appropriate canonical amino acid onto its corresponding tRNA (e.g. reviewed by Reitz et al., 2018, Synthesis of non-canonical branched-chain amino acids in *Escherichia coli* and approaches to avoid their incorporation into recombinant proteins, Curr Opin Biotechnol. October; 53:248-253). Such fidelity can be jeopardized by a number of non-canonical amino acids, particularly ncBCAA, which are structurally similar to their canonical equivalents (Martinis S A, Fox G E. Non-standard amino acid recognition by *Escherichia coli* leucyl-tRNA synthetase. Nucleic Acids Symp Ser. 1997; 36:125-128). For instance, leucyl-tRNA synthetase (leuRS) must distinguish between leucine and the non-canonical counterpart norvaline, which only differ by a single methyl group (Apostol, I., et al., 1997, Incorporation of norvaline at leucine positions in recombinant human hemoglobin expressed in *Escherichia coli*. Journal of Biological Chemistry, 272(46), 28980-28988.). The same applies for methionyl-tRNA synthetase (metRS), which must discriminate between methionine and norleucine (Kiick, K. L., et al., 2001, Identification of an expanded set of translationally active methionine analogues in *Escherichia coli*. FEBS Letters, 502(1-2), 25-30.), and isoleucyl-tRNA synthetase (ileRS), which must differentiate between isoleucine and β-methylnorleucine (Muramatsu, R., et al., 2003. Finding of an isoleucine derivative of a recombinant protein for pharmaceutical use. Journal of pharmaceutical and biomedical analysis, 31(5), 979-987.). For example, when *E. coli* is grown on a mineral salt medium and methionine is limiting, norleucine can undergo acylation onto a methionyl transfer RNA and subsequently become incorporated into the recombinant protein whenever methionine codons are translated.

Although different expression systems for recombinant protein production are available and adaption of culture conditions for improved recombinant protein production have been reported, the problem of a potential overflow metabolism and misincorporation of unwanted amino acids into the recombinant protein of interest is still unsolved.

The conditions under which misincorporation of non-canonical branched chain amino acids into heterologous recombinant proteins occur and how to efficiently prevent such misincorporations are not completely understood. A method for the production of recombinant polypeptides without misincorporation of non-canonical branched-chain amino acids would therefore be highly desired.

The technical problem underlying the present invention can be seen as the provision of means and methods for complying with the aforementioned needs. The technical problem is solved by the embodiments characterized in the claims and herein.

SUMMARY OF THE INVENTION

The present invention relates to a method for producing a recombinant polypeptide of interest in a microbial host cell, comprising the steps of (a) introducing a polynucleotide encoding the polypeptide of interest into a microbial host cell which has been modified such that an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase activity (EC 4.3.1.19) is modulated (such as increased) in said microbial host cell as compared to the enzymatic activity in an unmodified microbial host cell, and (b) expressing said polypeptide of interest in said microbial host cell.

The present invention further relates to a method for reducing misincorporation of at least one non-canonical branched-chain amino acid into a recombinant polypeptide of interest expressed in a microbial host cell, said method comprising (a) modulating (such as increasing) an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase activity (EC 4.3.1.19) in the microbial host cell, (b) introducing a polynucleotide encoding the polypeptide of interest into said microbial host cell, and (c) expressing said polypeptide of interest in said microbial host cell.

Further envisaged by the present invention is a microbial host cell comprising:

(a) a recombinant polynucleotide encoding a polypeptide of interest, and (b) a recombinant polynucleotide encoding a polypeptide having an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase activity (EC 4.3.1.19).

Further envisaged by the present invention is a bioreactor comprising the microbial host cell of the present invention. In some embodiments, the bioreactor has a volume of at least 10 L.

Moreover, the present invention relates to the use of a polypeptide having an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase activity (EC 4.3.1.19), or of a polynucleotide encoding said polypeptide for reducing misincorporation of at least one non-canonical branched-chain amino acid into a recombinant polypeptide of interest produced in a microbial host cell.

Finally, the present invention concerns the use of a microbial host cell for producing a recombinant polypeptide of interest, wherein the microbial host cell has been modified such that an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase activity (EC 4.3.1.19) is modulated in said microbial host cell as compared to the enzymatic activity in an unmodified microbial host cell.

In an embodiment of the method, the use, or the microbial host cell of the present invention, the microbial host cell does not express an endogenous polypeptide having said enzymatic activity. Accordingly, the endogenous, i.e. naturally occurring polynucleotide, encoding for the polypeptide having said enzymatic activity has been deleted, i.e. knocked out in the microbial host cell.

In an embodiment of the method, the use, or the microbial host cell of the present invention, the polypeptide of interest is a therapeutic polypeptide such as a proinsulin, an insulin or an insulin analogue.

In an embodiment of the method, the use, or the microbial host cell of the present invention, the polynucleotide encoding the polypeptide of interest and/or the polynucleotide encoding the polypeptide having said enzymatic activity is operably linked to an inducible promoter.

In an embodiment of the method, the use, or the microbial host cell of the present invention, the microbial host cell is an *Escherichia coli* cell.

DETAILED DESCRIPTION OF THE INVENTION

As set forth above, the present invention relates to a method for producing a recombinant polypeptide of interest in a microbial host cell. The method comprises (a) the introduction of a polynucleotide encoding the polypeptide of interest into a microbial host cell which has been modified such that an enzymatic activity as set forth elsewhere herein is modulated in said microbial host cell as compared to the enzymatic activity in an unmodified microbial host cell, and (b) expressing said polypeptide of interest in said microbial host cell.

In accordance with the present invention, a recombinant polypeptide of interest shall be produced in a microbial host cell. The term "recombinant polypeptide" as used herein refers to a genetically engineered polypeptide. Accordingly, the polypeptide to be produced shall be heterologous with respect to the microbial host cell which means that the host cell does not naturally express the polypeptide of interest. The term "heterologous", thus, means that the polynucleotide/polypeptide does not occur naturally in the microbial host cell.

In a preferred embodiment of the present invention, the recombinant polypeptide of interest to be produced is a therapeutic polypeptide.

In particular, it is envisaged that the recombinant polypeptide of interest is an antibody or antigen-binding fragment thereof, an enzyme, a receptor, a secreted protein, a fusion protein, or a hormone, in particular a peptide hormone (such as insulin, or a precursor thereof such as a proinsulin).

In a preferred embodiment, the recombinant polypeptide of interest is an antibody or antigen-binding fragment thereof. The antibody is, preferably, selected from a multispecific antibody, a human antibody, a humanized antibody, a chimeric antibody, and a single-chain antibody. Preferably, the antigen-binding fragment of the antibody is selected from the group consisting of a Fab fragment, a Fab' fragment, a $F(ab')_2$ fragment, a scFv fragment, and a Fv fragment. For example, the antigen-binding fragment is a $F(ab')_2$ fragment.

In another preferred embodiment, the recombinant polypeptide of interest is proinsulin or insulin. Insulin is a peptide hormone which is naturally secreted by the islets of Langerhans and functions in the regulation of the metabolism of carbohydrates and fats, particularly the conversion of glucose to glycogen. The insulin may be a naturally occurring insulin, in particular human insulin, or an analog of a naturally occurring insulin, in particular an analog of human insulin. Accordingly, the term "insulin" encompasses naturally occurring insulins and analogs thereof. An insulin analog is an altered form of insulin, different from any occurring in nature, but still available to the human body for performing the same action as human insulin in terms of glycemic control. Preferably, the insulin analog is selected from insulin lispro, insulin aspart, insulin glulisine, insulin detemir, and insulin glargine.

Other recombinant polypeptides of interest are hirudin, somatotropin, an interleukin such as interleukin-2, or hemoglobin.

It is to be understood that the recombinant polypeptide of interest shall comprise at least one isoleucine residue, at least one leucine residue, and/or at least one methionine residue.

In an embodiment, the recombinant polypeptide of interest is a leucine-rich polypeptide. For example, at least 5%, at least 10%, or at least 15% or all amino acids of the polypeptide are leucine residues. For example, the recombinant polypeptide of interest may have a length of 96 amino acids and may comprise 14 leucine residues. Alternatively, the recombinant polypeptide of interest may have a length of 44 amino acids and may comprise 8 leucine residues. Alternatively, the recombinant polypeptide of interest may have a length of 52 amino acids and may comprise 6 leucine residues.

In another embodiment, the recombinant polypeptide of interest is an isoleucine-rich polypeptide. For example, at least 5%, at least 10%, or at least 15% or all amino acids of the polypeptide are isoleucine residues.

In another embodiment, the recombinant polypeptide of interest is a methionine-rich polypeptide. For example, at least 5%, at least 10%, or at least 15% or all amino acids of the polypeptide are methionine residues.

In particular, the analog of insulin is insulin glargine. Insulin glargine is a long-acting basal insulin analogue. Insulin glargine is produced by recombinant DNA technology using a non-pathogenic laboratory strain of *Escherichia coli* (K12) as the production organism. It is an analogue of human insulin made by replacing the asparagine residue at position A21 of the A-chain with glycine and adding two arginine residues to the C-terminus (positions B31 and 32) of the B-chain. The resulting protein is soluble at pH 4 and forms microprecipitates at physiological pH 7.4. Small amounts of insulin glargine are slowly released from microprecipitates giving the drug a long duration of action (up to 24 hours) and no pronounced peak concentration. It is marketed under the name Lantus®. The CAS Registry Number for insulin glargine is 160337-95-1.

The recombinant polypeptide of interest is preferably not a polypeptide that is expressed in the organism in the untransformed state. Preferably, it is also not a polypeptide which is expressed as a selection marker (i.e. the polypeptide shall not confer a resistance such as a resistance to an antibiotic to the cell). Further, it is preferably not a polypeptide which is expressed as reporter polypeptide (such as a fluorescent polypeptide or the GUS-polypeptide).

In an embodiment of the method of the present invention, the recombinant polypeptide of interest and the polypeptide having an enzymatic activity as referred to herein are co-expressed. Thus, the recombinant polypeptide of interest is not the polypeptide having an enzymatic activity as referred to herein in connection with the method of the present invention. Preferably, the recombinant polynucleotide encoding the polypeptide of interest and the polynucleotide encoding the polypeptide having an enzymatic activity as referred to herein are not present on the same plasmid. Accordingly, it is envisaged that they are expressed from different plasmids. Thus, the polypeptides are comprised by different DNA molecules.

In accordance with the present invention, the recombinant polypeptide of interest is produced by introduction of a recombinant polynucleotide encoding the polypeptide of interest into the microbial host cell as defined herein and by expressing said recombinant polypeptide of interest in said microbial host cell.

Preferably, the polynucleotide encoding the polypeptide of interest is comprised by an expression plasmid, i.e. a plasmid which allows for the expression of said polynucleotide. The same applies to the polynucleotide encoding for a polypeptide having enzymatic activity as defined elsewhere herein. In order to express the polynucleotide, said polynucleotide is operably linked to a promoter. The term "operably linked" as used herein refers to a functional linkage between the promoter and the polynucleotide to be expressed, such that the promoter is able to initiate transcription of said polynucleotide. Preferred promoters are described elsewhere herein.

The expression plasmid may comprise further elements. Preferably, the plasmid additionally comprises a selectable marker gene which allows for the selection of microbial host cells. For example, this can be a gene which confers resistance to an antibiotic such as ampicillin, chloramphenicol, kanamycin, or tetracycline.

Furthermore, it is envisaged that the plasmid comprises a replicon which allows for the replication of the plasmid in the microbial host cell. In a preferred embodiment, only one copy of the plasmid comprising the polynucleotide encoding the polypeptide having an enzymatic activity as set forth herein in connection with the method of the present invention is present in the microbial host cell. Thus, the copy number of said plasmid in the microbial host cell shall be one. This may be achieved by the presence of ori2 and its elements repE, sopA, sopB, and sopC which ensures 1 copy of the plasmid per cell. In contrast, the polynucleotide encoding the polypeptide of interest may be present on a medium or high copy plasmid.

Methods of introducing a polynucleotide into a microbial host cell are well known in the art. Preferably, said polynucleotide is introduced into the microbial host cell by transformation. Transformation is the process by which an organism acquires a heterogeneous or recombinant polynucleotide. In an embodiment, the transformation of the microbial host cell involves use of divalent cations such as calcium chloride to increase the permeability of the membrane of the host cell, making the host cell chemically competent, thereby increasing the likelihood of uptake of the recombinant polynucleotide. In another embodiment, the polynucleotide is transformed into the host cell by electroporation. Further, the polynucleotide may be stably introduced into the host cell, i.e. into the chromosome of the host cell.

The microbial host cell is preferably a bacterium. More preferably, the microbial host cell is an *Escherichia coli* (*E. coli*) cell. *E. coli* is a Gram-negative gammaproteobacterium. The descendants of two isolates, K-12 and B strain, are used routinely in molecular biology as both a tool and a model organism. Preferably, the *E. coli* cell is an *E. coli* cell of the strain K12. Preferably, the *E. coli* cell strain is *E. coli* K12 BW25113 (see Grenier, 2014, Genome Announc. September-October; 2(5): e01038-14).

The present invention is not limited to *E. coli*, as the misincorporation of ncBCAAs also occurs in other bacteria such as *B. subtilis* or *S. marcescens*.

According to the present invention, the polynucleotide encoding the polypeptide of interest shall be introduced into a microbial host cell. Said microbial host cell shall have been modified such that an enzymatic activity as set forth elsewhere herein has been modulated (such as increased) in said microbial host cell as compared to the enzymatic activity in an unmodified microbial host cell. Thus, the method of the present invention may further comprise (prior to step a), i.e. the introduction step) the step of providing or obtaining a microbial host cell having a modulated enzymatic activity selected from the group consisting of ketol-acid reductoisomerase (NADP(+) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase activity (EC 4.3.1.19). In this particular method said enzymatic activity shall be modulated as compared to an unmodified microbial host cell. Alternatively, an exemplary method of the present invention may comprise prior to step a), the step of modulating an enzymatic activity as set forth above in the microbial host cell.

In an embodiment of the present invention, the term "modulating an enzymatic activity" refers to increasing the enzymatic activity (as compared to the control or unmodified enzymatic activity). In another embodiment, the term refers to decreasing the enzymatic activity (as compared to the control or unmodified enzymatic activity).

Methods of increasing enzymatic activity of a polypeptide are well known in the art. For example, a polypeptide having enzymatic activity can be mutated to increase its activity (e.g. by enzyme design or enzyme engineering).

In an embodiment of the present invention, the enzymatic activity as referred to herein is increased in the microbial host cell into which the polynucleotide encoding the polypeptide of interest is introduced. Preferably, the enzymatic activity is increased by at least 10% as compared to the corresponding enzymatic activity in the unmodified microbial host cell. More preferably, the enzymatic activity is increased by at least 20%, even more preferably by at least 30%, and even more preferably by at least 50% as compared to the enzymatic activity in the unmodified microbial host cell. In an embodiment the enzymatic activity is increased by at least 100% or in another embodiment by at least 150%. Further, it is envisaged that the enzymatic activity is increased by 20% to 300%, such as by 50% to 200%. In an embodiment, the enzymatic activity is increased by overexpressing a polynucleotide encoding a polypeptide having said enzymatic activity.

In an embodiment of the present invention, the enzymatic activity as referred to herein is decreased in the microbial host cell into which the polynucleotide encoding the polypeptide of interest is introduced. Preferably, the enzymatic activity is decreased by at least 10% as compared to the corresponding enzymatic activity in the unmodified microbial host cell. More preferably, the enzymatic activity is decreased by at least 20%, even more preferably by at least 30%, and even more preferably by at least 50% as compared to the enzymatic activity in the unmodified microbial host cell. In an embodiment the enzymatic activity is decreased by at least 80% as compared to the enzymatic activity in the unmodified microbial host cell. However, it is envisaged that the enzymatic activity is not completely knocked-out. For example, the host cell might retain at least 5%, at least 10% or at least 20% of the enzymatic activity of the unmodified microbial host cell. Thus, the enzymatic activity might be decreased by 20% to 80%. Alternatively, the enzymatic activity might be decreased by 30 to 70%. In an embodiment, the enzymatic activity is decreased by antisense RNAs which inhibit expression of the polynucleotide encoding a polypeptide having said enzymatic activity. Thus, the antisense RNAs should be complementary to the target gene.

In certain embodiments, the unmodified microbial host cell may be a wild-type cell. In a particular embodiment, an unmodified microbial host cell is of the same strain which has been modified. For example, the unmodified microbial host cell may be the *E. coli* K 12 strain, which may be subsequently modified as described herein.

The enzymatic activity to be modulated such as increased in the microbial host cell is, preferably, selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase activity (EC 4.3.1.19). The aforementioned enzymatic activities can be determined by assays well known in the art. The number in brackets is the so-called Enzyme Commission number (abbreviated "EC number"). As known in the art, every EC number consists of the letters EC followed by four numbers separated by periods. Those numbers represent a progressively finer classification of the enzyme. Based on the EC number, the reaction catalyzed by an enzyme is specified.

In an embodiment of the present invention, the enzymatic activity to be modulated is ketol-acid reductoisomerase (NADP(+)) activity. Accordingly, the activity of a ketol-acid reductoisomerase shall be modulated, preferably increased. The systematic name for this enzyme is (R)-2,3-dihydroxy-3-methylbutanoate: $NADP^+$ oxidoreductase (isomerizing). The EC number for this enzyme is EC 1.1.1.86. A ketol-acid reductoisomerase shall be capable of catalyzing the chemical reaction of (R)-2,3-dihydroxy-3-methylbutanoate+ $NADP^+$ into (S)-2-hydroxy-2-methyl-3-oxobutanoate, NADPH, and $H^+$. Accordingly, it shall be capable of catalyzing the following chemical reaction:

(R)-2,3-dihydroxy-3-methylbutanoate+$NADP^+$⇆(S)-2-hydroxy-2-methyl-3-oxobutanoate+NADPH+$H^+$ In another embodiment of the present invention, the enzymatic activity to be modulated is acetohydroxyacid synthase activity. Accordingly, the activity of an acetohydroxyacid synthase shall be modulated (e.g. increased or decreased). This enzyme is also known as acetolactate synthase. The EC number for this enzyme is EC 2.2.1.6. An acetohydroxyacid synthase shall be capable of catalyzing the conversion of two pyruvate molecules to an acetolactate molecule and carbon dioxide. The reaction uses thiamine pyrophosphate to link the two pyruvate molecules. Accordingly, it shall be capable of catalyzing the following chemical reaction:

2 pyruvate⇆2-acetolactate+$CO_2$

In another embodiment of the present invention, the enzymatic activity to be modulated is L-threonine dehydratase activity. Accordingly, the activity of a threonine synthase shall be modulated. The systematic name for this enzyme is L-threonine ammonia-lyase (2-oxobutanoate-forming). The EC number for this enzyme is EC 4.3.1.19.

In another embodiment of the present invention, the enzymatic activity to be modulated is aspartate kinase activity. Accordingly, the activity of an aspartate kinase activity shall be modulated. The systematic name for this enzyme is ATP:L-aspartate 4-phosphotransferase. The EC number for this enzyme is EC 2.7.2.4. An aspartate kinase shall be capable of catalyzing the conversion of beta-aspartyl phosphate from aspartic acid and ATP. Threonine serves as an allosteric regulator of this enzyme to control the biosynthetic pathway from aspartic acid to threonine. Accordingly, it shall be capable of catalyzing the following chemical reaction:

ATP+L-aspartate⇆ADP+4-phospho-L-aspartate

In another embodiment of the present invention, the enzymatic activity to be modulated is homoserine dehydrogenase activity. Accordingly, the activity of a homoserine dehydrogenase shall be modulated. The systematic name for this enzyme is L-homoserine: NAD $(P)^+$ oxidoreductase. The EC number for this enzyme is EC 1.1.1.3. A homoserine dehydrogenase shall be capable of catalyzing the chemical reaction of L-homoserine and $NAD^+$ (or $NADP^+$) into L-aspartate 4-semialdehyde, NADH (or NADPH), and $H^+$. Accordingly, it shall be capable of catalyzing the following chemical reaction:

L-homoserine+$NAD(P)^+$⇆L-aspartate 4-semialdehyde+NAD(P)H+$H^+$

The enzyme from *Escherichia coli* which has aspartate kinase activity also catalyses the reaction of EC 1.1.1.3 homoserine dehydrogenase. Accordingly, said enzyme is a bifunctional enzyme which has both aspartate kinase activity and homoserine dehydrogenase activity. Accordingly, it is envisaged that both enzymatic activities, i.e. the activity of an aspartate kinase and the activity of a homoserine dehydrogenase are modulated in the microbial host cell as compared to the aspartate kinase activity and the homoserine dehydrogenase activity in an unmodified microbial host cell.

The enzymatic activity as referred to herein is preferably increased by introducing a polynucleotide encoding a polypeptide having said enzymatic activity into the microbial host cell and expressing said polynucleotide. For example, the polynucleotide shall be overexpressed. The polypeptide encoded by said polynucleotide shall be an enzyme having the enzymatic activity as referred to herein. Preferred polypeptides conferring said enzymatic activities are disclosed elsewhere in this specification in detail. It is to be understood that the polypeptides referred to herein may also exhibit further biological activities.

It is to be understood that said polynucleotide encoding a polypeptide having said enzymatic activity is not the polynucleotide encoding the polypeptide of interest. Accordingly, the microbial host cell as referred to herein comprises a) a polynucleotide encoding a polypeptide having an enzymatic activity as referred to herein and b) polynucleotide encoding the polypeptide of interest. Accordingly, the polynucleotides under a) and b) are co-expressed in the microbial host cell. Further, it is to be understood that both polynucleotides are recombinant polynucleotides which have been introduced into the host cell artificially.

Preferred sequences for the polynucleotide encoding a polypeptide having an enzymatic activity as referred to herein are provided below.

In an embodiment of the present invention, the polynucleotide encodes a polypeptide having ketol-acid reductoisomerase (NADP(+) activity (EC 1.1.1.86). Preferably, said polynucleotide i) comprises a nucleic acid sequence having at least 40% sequence identity to the nucleic acid sequence as shown in SEQ ID NO: 3, and/or ii) encodes a polypeptide comprising an amino acid sequence having at least 40% sequence identity to the amino acid sequence shown in SEQ ID NO: 4.

In another embodiment of the present invention, the polynucleotide encodes a polypeptide having L-threonine dehydratase activity. Preferably, said polynucleotide i) comprises a nucleic acid sequence having at least 40% sequence identity to the nucleic acid sequence as shown in SEQ ID NO: 11, and/or ii) encodes a polypeptide comprising an amino acid sequence having at least 40% sequence identity to the amino acid sequence shown in SEQ ID NO: 12.

In an embodiment, the enzymatic activity to be modulated is acetohydroxyacid synthase (AHAS) activity, in particular, the activity of AHAS isoform I, or variants thereof, AHAS isoform II, or variants thereof, or AHAS isoform III, or variants thereof. The activity of AHAS isoform I, or variants thereof, is preferably decreased in order to reduce misincorporation of ncBCAAs. The activity of AHAS isoforms II and III, or variants thereof, is preferably increased in order to reduce misincorporation of ncBCAAs.

As known in the art, a functional acetohydroxyacid synthase (e.g. AHAS I, AHAS II or AHAS III) comprises two large subunits and two small subunits which form a tetramer (which has acetohydroxyacid synthase activity). The two large subunits as well the two small subunits are identical. Accordingly, acetohydroxyacid synthase activity is preferably increased in the microbial host cell by introducing a first polynucleotide encoding for the large subunit of the acetohydroxyacid synthase and a second polynucleotide encoding for the small subunit of the acetohydroxyacid synthase into the microbial host cell and by expressing the polynucleotides. In the microbial cell, two large subunits and two small units preferably form a tetramer. It is to be understood that said tetramer shall have acetohydroxyacid synthase activity. The first and the second polynucleotide are preferably present in the same construct and are preferably expressed in a bicistronic manner under control of a single promoter.

AHAS I or Variants Thereof

In an embodiment of the present invention, said first polynucleotide i) comprises a nucleic acid sequence having at least 40% sequence identity to the nucleic acid sequence as shown in SEQ ID NO: 23, and/or ii) encodes large subunit of an acetohydroxyacid synthase, said large subunit comprising an amino acid sequence having at least 40% sequence identity to the amino acid sequence shown in SEQ ID NO: 24, and said second polynucleotide i) comprises a nucleic acid sequence having at least 40% sequence identity to the nucleic acid sequence as shown in SEQ ID NO: 25, and/or ii) encodes a small subunit of an acetohydroxyacid synthase, said small subunit comprising an amino acid sequence having at least 40% sequence identity to the amino acid sequence shown in SEQ ID NO: 26.

SEQ ID NO: 24 is the amino acid sequence of the large subunit of acetohydroxyacid synthase isoform I from *E. coli*, whereas SEQ ID NO: 26 is the amino acid sequence of the small subunit of said isoform.

AHAS II or Variants Thereof

In another embodiment of the present invention, said first polynucleotide i) comprises a nucleic acid sequence having at least 40% sequence identity to the nucleic acid sequence as shown in SEQ ID NO: 5, 27 or 31, ii) encodes large subunit of an acetohydroxyacid synthase, said large subunit comprising an amino acid sequence having at least 40% sequence identity to the amino acid sequence shown in SEQ ID NO: 6, 28 or 32 and said second polynucleotide i) comprises a nucleic acid sequence having at least 40% sequence identity to the nucleic acid sequence as shown in SEQ ID NO: 7, 29, or 33 and/or ii) encodes the small subunit of an acetohydroxyacid synthase, said small subunit comprising an amino acid sequence having at least 40% sequence identity to the amino acid sequence shown in SEQ ID NO: 8, 30 or 34.

SEQ ID NO: 6 is the amino acid sequence of the large subunit of acetohydroxyacid synthase isoform II from *E. coli*, whereas SEQ ID NO: 8 is the amino acid sequence of the small subunit of said isoform. In a preferred embodiment, the AHAS isoform of *E. coli* is used (or a variant thereof).

SEQ ID NO: 28 is the amino acid sequence of the large subunit of acetohydroxyacid synthase isoform III from *Shigella boydii*, whereas SEQ ID NO: 30 is the amino acid sequence of the small subunit of said isoform.

SEQ ID NO: 32 is the amino acid sequence of the large subunit of acetohydroxyacid synthase isoform III from *Serratia marcescens*, whereas SEQ ID NO: 34 is the amino acid sequence of the small subunit of said isoform.

AHAS III of Variants Thereof

In another embodiment of the present invention, said first polynucleotide i) comprises a nucleic acid sequence having at least 40% sequence identity to the nucleic acid sequence as shown in SEQ ID NO: 13, 35, 39, or 43 and/or ii) encodes large subunit of an acetohydroxyacid synthase, said large subunit comprising an amino acid sequence having at least 40% sequence identity to the amino acid sequence shown in SEQ ID NO: 14, 36, 40, or 44 and said second polynucleotide i) comprises a nucleic acid sequence having at least 40% sequence identity to the nucleic acid sequence as shown in SEQ ID NO: 15, 37, 41, or 45 and/or ii) encodes a small subunit of an acetohydroxyacid synthase, said small subunit comprising an amino acid sequence having at least 40% sequence identity to the amino acid sequence shown in SEQ ID NO: 16, 38, 42, or 46.

SEQ ID NO: 14 is the amino acid sequence of the large subunit of acetohydroxyacid synthase isoform III from *E. coli*, whereas SEQ ID NO: 16 is the amino acid sequence of the small subunit of said isoform. In a preferred embodiment, the AHAS isoform of *E. coli* is used (or a variant thereof).

SEQ ID NO: 36 is the amino acid sequence of the large subunit of acetohydroxyacid synthase isoform III from *Shigella boydii*, whereas SEQ ID NO: 38 is the amino acid sequence of the small subunit of said isoform.

SEQ ID NO: 40 is the amino acid sequence of the large subunit of acetohydroxyacid synthase isoform III from *Serratia marcescens*, whereas SEQ ID NO: 42 is the amino acid sequence of the small subunit of said isoform.

SEQ ID NO: 44 is the amino acid sequence of the large subunit of acetohydroxyacid synthase isoform III from *Bacillus subtilis*, whereas SEQ ID NO: 46 is the amino acid sequence of the small subunit of said isoform.

As set forth above, it is envisaged that both the activity of an aspartate kinase and of a homoserine dehydrogenase are modulated in the microbial host cell (as compared to the unmodified microbial host cell). In a preferred embodiment, the increase of these two activities is by introducing and expressing a polynucleotide encoding a polypeptide having aspartate kinase and homoserine dehydrogenase activity. Accordingly, said polypeptide is a bifunctional polypeptide. Preferably, said polynucleotide encoding a polypeptide having aspartate kinase and homoserine dehydrogenase activity:

i) comprises a nucleic acid sequence having at least 40% sequence identity to the nucleic acid sequence as shown in SEQ ID NO: 17, and/or ii) encodes a polypeptide comprising an amino acid sequence having at least 40% sequence identity to the amino acid sequence shown in SEQ ID NO: 18.

The term "polynucleotide" as used herein refers to a linear or circular nucleic acid molecule. It encompasses DNA as well as RNA molecules. The polynucleotide of the present invention shall be provided, preferably, either as an isolated polynucleotide (i.e. isolated from its natural context) or in genetically modified form. The term encompasses single as well as double stranded polynucleotides. Moreover, the term comprises chemically modified polynucleotides including naturally occurring modified polynucleotides such as glycosylated or methylated polynucleotides or artificial modified polynucleotides, such as biotinylated polynucleotides. The polynucleotide of the present invention is characterized in that it shall encode a polypeptide as referred to above. The polynucleotide, preferably, has a specific nucleotide sequence as mentioned above. Moreover, due to the degeneracy of the genetic code, polynucleotides are encompassed which encode a specific amino acid sequence as recited above.

Moreover, the term "polynucleotide" as used in accordance with the present invention further encompasses variants of the aforementioned specific polynucleotides. Said variants may represent orthologs, paralogs or other homologs of the polynucleotide of the present invention. The polynucleotide variants, preferably, comprise a nucleic acid sequence characterized in that the sequence can be derived from the aforementioned specific nucleic acid sequences by at least one nucleotide substitution, addition and/or deletion whereby the variant nucleic acid sequence shall still encode a polypeptide having the activity as specified above.

In a preferred embodiment of the present invention, the polynucleotide as set forth herein above shall have at least 40% sequence identity to the nucleic acid sequence as shown in SEQ ID NO: 3, 5, 7, 11, 13, 15, 17, 23, 25, 27, 29, 31, 33, 35, 37, 39, 41, 43 or 45. Further, it is envisaged that the polynucleotide encodes a polypeptide comprising an amino acid sequence having at least 40% sequence identity to the amino acid sequence shown in SEQ ID NO: 4, 6, 8, 12, 14, 16, 18, 24, 26, 28, 30, 32, 34, 36, 38, 40, 42, 44 or 46 The term "at least 40%" as used herein means 40% or more than 40%. In particular, the term means, at least 50%, at least 60%, at least 70%, at least 80%, at least 85%, at least 90%, at least 95%, at least 98%, or at least 99% sequence identity (in increasing order of preference). Moreover, the term encompasses the exact sequence, i.e., 100% sequence identity. Thus, the polynucleotide may have or comprise the nucleic acid sequence as shown in SEQ ID NO: 3, 5, 7, 11, 13, 15, 17, 23, 25, 27, 29, 31, 33, 35, 37, 39, 41, 43 or 45 or may encode a polypeptide comprising an amino acid sequence as shown in SEQ ID NO: 4, 6, 8, 12, 14, 16, 18, 24, 26, 28, 30, 32, 34, 36, 38, 40, 42, 44 or 46.

Sequence identity between amino acid sequences or nucleic acid sequences as used herein can be assessed by determining the number of identical nucleotides or amino acids between two nucleic acid sequences or amino acid sequences wherein the sequences are aligned so that the highest order match is obtained. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. It can be calculated using published techniques or methods codified in computer programs such as, for example, BLASTP, BLASTN or FASTA (Altschul 1990, J Mol Biol 215, 403). The percent identity values are, preferably, calculated over a comparison window. A comparison window, preferably, is the length of the entire sequence of the shorter sequence to be aligned or at least half of said sequence. To carry out the sequence alignments, the program PileUp (Higgins 1989, CABIOS 5, 151) or the programs Gap and BestFit (Needleman 1970, J Mol Biol 48:443; Smith 1981, Adv Appl Math 2:482), which are part of the GCG software packet (Genetics Computer Group 1991, 575 Science Drive, Madison, Wisconsin, USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. Preferably, the degree of sequence identity is calculated over the entire length.

In an embodiment, the algorithm of Needleman and Wunsch (see above) is used for the comparison of sequences. The algorithm is incorporated in the sequence alignment software packages GAP Version 10 and wNEEDLE. E.g., wNEEDLE reads two sequences to be aligned, and finds the optimum alignment along their entire length. When amino acid sequences are compared, a default Gap open penalty of 10, a Gap extend penalty of 0.5, and the EBLOSUM62 comparison matrix are used. When DNA sequences are compared using wNEEDLE, a Gap open penalty of 10, a Gap extend penalty of 0.5, and the EDNAFULL comparison matrix are used.

Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N. Y. (1989), 6.3.1-6.3.6. Accordingly, it is envisaged that the polynucleotide as set forth above shall be capable of hybridizing to a polynucleotide having a sequence as shown in SEQ ID NO: 3, 5, 7, 11, 13, 15, 17, 23, 25, 27, 29, 31, 33, 35, 37, 39, 41, 43 or 45, in particular, the polynucleotide as set forth above shall be the complement of a polynucleotide having a sequence as shown in SEQ ID NO: 3, 5, 7, 11, 13, 15, 17, 23, 25, 27, 29, 31, 33, 35, 37, 39, 41, 43 or 45.

The term "hybridization" is well known in art and refers to a process in which substantially homologous complementary nucleotide sequences anneal to each other. The hybridization process can occur entirely in solution, i.e. both complementary nucleic acids are in solution. Hybridization can also occur with one of the complementary nucleic acids immobilized to a matrix such as Sepharose beads. In order to allow hybridization to occur, the nucleic acid molecules are thermally or chemically denatured to melt a double strand into two single strands and/or to remove hairpins or other secondary structures from single stranded nucleic acids.

In accordance with the present invention, the polynucleotide shall be capable of hybridizing under stringent conditions, in particular under high stringency hybridization conditions, to a polynucleotide having a sequence as shown in SEQ ID NO: 3, 5, 7, 11, 13, 15, 17, 23, 25, 27, 29, 31, 33, 35, 37, 39, 41, 43 or 45. The term "stringency" refers to the conditions under which hybridization takes place. The stringency of hybridization is influenced by conditions such as temperature, salt concentration, ionic strength and hybridization buffer composition. In a preferred embodiment high stringency hybridization conditions encompass hybridization at 65° C. in 1×SSC or at 42° C. in 1×SSC and 50% formamide, followed by washing at 65° C. in 0.3×SSC. Further, it is envisaged that the hybridization is followed by washing at 65° C. in 0.1×SSC. 1×SSC is 0.15M NaCl and 15 mM sodium citrate; the hybridization solution and wash solutions may additionally include 5×Denhardt's reagent, 0.5-1.0% SDS, 100 μg/ml denatured, fragmented salmon sperm DNA, and 0.5% sodium pyrophosphate.

In step (b) of the method of the present invention, the polypeptide of interest is expressed in said microbial host cell. Preferably, said step is carried out under conditions which allow for the expression of the said polypeptide. Suitable cultivation conditions can be determined by the skilled person without further ado. Preferably, the step is carried out under standard conditions. Thus, the host cell is incubated under standard conditions, e.g. under standard conditions described in Example 9.

In an embodiment, the expression is carried out under large-scale conditions in a bioreactor. The term "bioreactor" as used herein refers to a system in which conditions are closely controlled. In an embodiment, said bioreactor is a stirred tank bioreactor. Preferably, the bioreactor is made of a non-corrosive material such as stainless steel. The bioreactor can be of any size. In some embodiments, the bioreactor has a volume of at least 10, at least 100, 500, at least 1000, at least 2500, or at least 5000 liters or any intermediate volume.

In accordance with the present invention, the polynucleotide encoding the polypeptide of interest is operably linked to a promoter. The same applies to the polynucleotide encoding the polypeptide having the enzymatic activity as referred to herein. However, is preferred that the aforementioned polynucleotides are linked to different promoters.

The promoter shall allow for the expression of the polynucleotide. Preferably, the promoter is heterologous with respect to the sequence controlled by it. Thus, the promoter shall be heterologous to the polynucleotide encoding the polypeptide having the enzymatic activity and to the polynucleotide encoding the polypeptide of interest, respectively. Preferably, the promoter is a constitutive or inducible promoter. Constitutive and inducible promoters which allow for the expression in a microbial host cell are well known in the art.

A "constitutive promoter" refers to a promoter that is transcriptionally active during most, but not necessarily all, phases of growth and under most environmental conditions.

An "inducible promoter" refers to a promoter that has increased transcription initiation in response to a stimulus.

In accordance with the present invention, it is particularly contemplated that the promoter is an inducible promoter. Thus, the polynucleotide encoding the polypeptide of interest and/or the polynucleotide encoding the polypeptide having said enzymatic activity shall be operably linked to an inducible promoter. In this case, the enzymatic activity is only increased temporarily (i.e. after induction of the promoters).

In an embodiment, the inducible promoter is the arabinose-inducible araBAD promoter. The promoter is well known in the art. The arabinose-inducible araBAD promoter (PBAD) together with its regulator protein AraC has been described as expression system for high-level recombinant protein production as well as for metabolic engineering purposes since expression is tunable over a broad range of arabinose concentrations (Guzman et al., 1995, Tight regulation, modulation, and high-level expression by vectors containing the arabinose PBAD promoter. Journal of bacteriology, 177(14), 4121-4130). The AraC-PBAD promoter system was also shown to be regulated by catabolite repression (Schleif, R., 2000, Regulation of the L-arabinose operon of *Escherichia coli*. Trends in Genetics, 16(12), 559-565; Megerle et al, 2008, Timing and dynamics of single cell gene expression in the arabinose utilization system. Biophysical journal, 95(4), 2103-2115). Moreover, the applicability of the AraC-PBAD expression system was reported to be dependent on the *E. coli* strain. Cloning vectors usually contain native sequences of araBAD promoter and araC gene from the native araBAD regulatory system.

The sequence of the araBAD promoter is shown in SEQ ID NO: 19. Accordingly, the araBAD promoter preferably comprises a nucleic acid sequence as shown in SEQ ID NO: 19 or is at least 70%, at least 80% or is at least 90% identical thereto.

The nucleic acid sequence of the polynucleotide araC is shown in SEQ ID NO: 20. This gene encodes the AraC polypeptide. If the araBAD promoter is used, a polynucleotide expressing the AraC polypeptide has to be introduced into the microbial host cell to activate the promoter.

Further inducible promoters are the rhaBAD promoter, variants of the lac promoter (such as the lacUV5, Ptac, Ptrc and T7lac promoter), the XylSPm promoter, and tet promoter.

The polypeptide having an enzymatic activity as referred to herein and/or the polypeptide of interest may comprise additional sequences. For example, the polypeptide(s) may further comprise a purification tag. The tag shall be operably linked to the polypeptide.

The tag shall allow the purification of the polypeptide. Such tags are well known in the art. The term "purification tag" as used herein preferably refers to an additional amino acid sequence (a peptide of the polypeptide) which allows for purification of the polypeptide. In an embodiment, the purification tag is a peptide or polypeptide which is not naturally linked to the polypeptide as referred to herein. Thus, the purification tag shall be heterologous with respect to the polypeptide.

Preferably, the purification tag is selected from the group consisting of a polyhistidine tag, a polyarginine tag, glutathione-S-transferase (GST), maltose binding protein (MBP), influenza virus HA tag, thioredoxin, staphylococcal protein A tag, the FLAG™ epitope, and the c-myc epitope. In a preferred embodiment, the purification tag is a polyhistidine tag. Preferably, said polyhistidine tag comprises at least 6 consecutive histidine residues.

In a preferred embodiment of the methods of the present invention, the method further comprises the isolation of the polypeptide of interest from the cell, and the purification of said polypeptide. The isolation of the polypeptide can be achieved by well-known means such as via the use of a suitable purification tag.

In an embodiment, the purification comprises the enrichment of polypeptides which do not comprise non-canonical branched-chain amino acids. This can be achieved by well-known methods which are e.g. described in Min, C. K., et al., 2012, Insulin related compounds and identification. Journal of Chromatography B, 908, 105-112; Harris, R. P., et al., 2014, Amino acid misincorporation in recombinant biopharmaceutical products. Current opinion in biotechnology, 30, 45-50; Cvetesic, N., et al., 2016, Proteome-wide measurement of non-canonical bacterial mistranslation by quantitative mass spectrometry of protein modifications. Scientific reports, 6, 2863. For example, the enrichment is achieved by chromatography.

The microbial host cell has been defined above. As set forth above, the microbial host cell is preferably an *E. coli* cell. As it is known by the skilled person, *E. coli* cells naturally expresses polypeptides having ketol-acid reductoisomerase (NADP(+) activity (EC 1.1.1.86), acetohydroxyacid synthase activity (EC 2.2.1.6), aspartate kinase activity (EC 2.7.2.4), homoserine dehydrogenase activity (EC 1.1.1.3), or L-threonine dehydratase activity (EC 4.3.1.19).

the ilvC gene encodes for a polypeptide having ketol-acid reductoisomerase (NADP(+)) activity the ilvIH operon encodes for a polypeptide having acetohydroxyacid synthase activity (acetohydroxyacid synthase isozyme III), the ilvBN operon encodes for a polypeptide having acetohydroxyacid synthase activity (acetohydroxyacid synthase isozyme I), the ilvGM operon encodes for a polypeptide having acetohydroxyacid synthase activity (acetohydroxyacid synthase isozyme II), the thrA gene encodes for a bifunctional polypeptide having aspartokinase and homoserine dehydrogenase activity, and the ilvA gene encodes for a polypeptide having L-threonine dehydratase activity.

Accordingly, the microbial host cell that has been modified may have endogenous enzymatic activities, i.e. activities which are naturally present in in the microbial host cell. However, it is in particular envisaged that the microbial host does not express an endogenous polynucleotide encoding polypeptide having the enzymatic activity as referred to herein. Thus, the endogenous enzymatic activity may have been knocked-out. Accordingly, it is envisaged that the endogenous polynucleotide (and thus the endogenous enzymatic activity) has been knocked-out. Thus, the ilvC gene, the ilvIH operon, the ilvBN operon, the thrA gene, the ilvGM operon, or the ilvA gene may have been knocked-out. This can be achieved by methods well known in the art and is described in the Examples section. Further, such knock-outs are already known and can be assessed e.g. from the *E. coli* Genetic Stock Center (CGSC) of Yale University. E.g., *E. coli* K12 BW25113 has a two-base insertion event between base pairs 1250 and 1253 of ilvG genetic sequence, resulting in a frameshift mutation. As a consequence, a stop codon is formed resulting in a premature termination of ilvG gene expression (ilvG-). A functional AHASII is then not expressed and distal gene expression of ilVEDA operon is impaired (Lawther et al., 1981, Molecular basis of valine resistance in *Escherichia coli* K-12, PNAS 78 (2) 922-925; Parekh, B. S. and Hatfield, G. W., 1997. Growth rate-related regulation of the ilvGMEDA operon of *Escherichia coli* K-12 is a consequence of the polar frameshift mutation in the ilvG gene of this strain. Journal of bacteriology, 179(6) 2086-2088.). In specific embodiments disclosed herein, knock-outs for ΔthrA, ΔilvA, and ΔilvC were acquired from the *E. coli* Genetic Stock Center (CGSC) of Yale University (see Examples section).

In an embodiment, the endogenous polynucleotide encoding the polypeptide having said enzymatic activity has been deleted. Alternatively, it may have been mutated, thereby deactivating the endogenous enzymatic activity. The endogenous polynucleotide is the naturally occurring polynucleotide which encodes for a polypeptide having an enzymatic activity as referred to herein.

For example, the L-threonine dehydratase activity can be increased in a microbial host cell by introducing and expressing a polynucleotide (i.e. a recombinant polynucleotide) encoding for a polypeptide having L-threonine dehydratase activity. In an embodiment, said microbial host cell expresses an endogenous polynucleotide encoding a polypeptide having L-threonine dehydratase activity (i.e. in addition to the recombinant polynucleotide). In another, more preferred embodiment, the endogenous polynucleotide encoding for the polypeptide having L-threonine dehydratase activity (and thus the ilvA gene) has been knocked-out in said microbial cell. Accordingly, said microbial cell does not express an endogenous polypeptide having L-threonine dehydratase activity. Only a recombinant polypeptide having said activity is expressed.

The knock-out of the endogenous gene (i.e. the endogenous enzymatic activity) in connection with the use of inducible promoters as described above allows for an improved regulation of the enzymatic activity in the microbial host cell.

In a preferred embodiment, the produced polypeptide of interest shows lower misincorporation of non-canonical branched-chain amino acids (ncBCAAs) as compared to a polypeptide which has been produced by expression in an unmodified microbial host cell. Accordingly, the misincorporation of ncBCAAs is reduced.

Preferably, the non-canonical branched-chain amino acid is selected from norvaline, norleucine and beta-methylnorleucine. Accordingly, the polypeptide of interest preferably shows lower norvaline, norleucine and beta-methylnorleucine misincorporation as compared to a polypeptide which has been produced by expression in an unmodified microbial host cell.

In some embodiments, misincorporation of non-canonical branched-chain amino acids is reduced in the intracellular soluble protein fraction. In some embodiments, misincorporation of non-canonical branched-chain amino acids is reduced in the inclusion body fraction.

Norvaline is an amino acid with the formula $CH_3(CH_2)_2CH(NH_2)CO_2H$. The compound is an isomer of the more common amino acid valine. The IUPAC name is 2-Aminopentanoic acid. Norvaline can be misincorporated into recombinant proteins in place of leucine residues. Accordingly, the term "norvaline misincorporation" refers to the incorporation of a norvaline residue in the polypeptide of interest for which a leucine residue is encoded by the corresponding nucleic acid encoding the polypeptide of interest.

Norleucine is an amino acid with the formula $CH_3(CH_2)_3CH(NH_2)CO_2H$. Norleucine is an isomer of the more common amino acid leucine. The IUPAC name is 2-aminohexanoic acid. Norleucine can be misincorporated into recombinant proteins in place of methionine residues. Accordingly, the term "norleucine misincorporation" refers to the incorporation of a norleucine residue in the polypeptide of interest for which a methionine residue is encoded by the corresponding nucleic acid encoding the polypeptide of interest.

Beta-methylnorleucine is an amino acid. Synonyms for this amino acid are beta-methylnorleucine; (2S,3S)-2-Amino-3-methylhexanoicacid and [2S,3S, (+)]-2-Amino-3-methylhexanoic acid. Beta-methylnorleucine can be misincorporated into recombinant proteins in place of isoleucine residues. Accordingly, the term "beta-methylnorleucine misincorporation" refers to the incorporation of a beta-methylnorleucine residue in the polypeptide of interest for which an isoleucine residue is encoded by the corresponding nucleic acid encoding the polypeptide of interest.

Thus, misincorporation of the ncBCAAs as referred to above may occur if the polypeptide of interest comprises at least one leucine residue, at least one methionine residues, and/or at least one isoleucine residue. Accordingly, it is envisaged that the polypeptide of interest comprises at least one leucine residue, at least one methionine residues, and/or at least one isoleucine residue.

In an embodiment of the present invention, the misincorporation of norvaline is reduced.

In an embodiment of the present invention, the misincorporation of norleucine is reduced.

In an embodiment of the present invention, the misincorporation of beta-methylnorleucine is reduced.

In an embodiment of the present invention, the misincorporation of norvaline and norleucine reduced.

In an embodiment of the present invention, the misincorporation of norleucine and beta-methylnorleucine is reduced.

In an embodiment of the present invention, the misincorporation of norvaline and beta-methylnorleucine is reduced.

In an embodiment of the present invention, the misincorporation of norvaline, norleucine and beta-methylnorleucine is reduced.

In accordance with the present invention, the percent reduction of the ncBCAA content, in particular of the norvaline, norleucine and/or beta-methylnorleucine content, is preferably at 5%, more preferably at least 10%, even more preferably at least 15%, and even more preferably at least 20% (as compared to the content in a polypeptide which has been produced by expression in an unmodified microbial host cell, i.e. the control cell). Thus, the misincorporation of ncBCAAs is preferably reduced by at least 5%, at least 10%, at least 15%, or at least 20%. The percent reduction in the content of ncBCAAs or in the content of norvaline, norleucine and/or beta-methylnorleucine is preferably calculated as a reduction in percentage of polypeptides of interest containing ncBCAAs or norvaline, norleucine and/or beta-methylnorleucine.

The definitions and explanations provided herein above apply mutatis mutandis to the following embodiments of the present invention.

The present invention further relates to a method for reducing misincorporation of at least one non-canonical branched-chain amino acid into a recombinant polypeptide of interest expressed in a microbial host cell, said method comprising

- (a) modulating an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase (EC 4.3.1.19) in the microbial host cell,
- (b) introducing a polynucleotide encoding the polypeptide of interest into said microbial host cell, and
- (c) expressing said polypeptide of interest in said microbial host cell.

Alternatively, step (a) may comprise obtaining a microbial host cell having modulated activity of an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase (EC 4.3.1.19).

In an embodiment, the enzymatic activity as set forth above shall be modulated (increased or decreased) in the microbial host cell as compared to an unmodified microbial host cell. Methods of modulating the enzymatic activity is described above. Preferably, said enzymatic activity is modulated (e.g. increased) by introducing and expressing a polynucleotide encoding a polypeptide having said enzymatic activity in said microbial host cell. Preferred sequences for the polynucleotide/polypeptide are described above.

Further envisaged by the present invention is a microbial host cell comprising

- (a) a recombinant polynucleotide encoding a polypeptide of interest, and
- (b) a recombinant polynucleotide encoding a polypeptide having an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase (EC 4.3.1.19).

Moreover, the present invention relates to the use of a polypeptide having an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), L-threonine dehydratase (EC 4.3.1.19), or of a polynucleotide encoding said polypeptide for reducing misincorporation of at least one non-canonical branched-chain amino acid into a recombinant polypeptide of interest produced in a microbial host cell.

Finally, the present invention concerns the use of a microbial host cell for producing a recombinant polypeptide of interest, wherein the microbial host cell has been modified such that an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase (EC 4.3.1.19) is modulated in said microbial host cell as compared to the enzymatic activity in an unmodified microbial host cell.

In the following, embodiments of the present invention are summarized. The definitions and explanations provided above apply mutatis mutandis to embodiments.

LIST OF EMBODIMENTS

1. A method for producing a recombinant polypeptide of interest in a microbial host cell, comprising the steps of
   - (a) introducing a polynucleotide encoding the polypeptide of interest into a microbial host cell which has been modified such that an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase (EC 4.3.1.19) is modulated in said microbial host cell as compared to the enzymatic activity in an unmodified microbial host cell, and
   - (b) expressing said polypeptide of interest in said microbial host cell.
2. The method of embodiment 1, wherein the produced polypeptide of interest shows lower misincorporation of non-canonical branched-chain amino acids as compared to a polypeptide which has been produced by expression in an unmodified microbial host cell.
3. The method of embodiments 1 and 2, wherein the amount of the produced polypeptide is increased as compared to the amount of said polypeptide produced in an unmodified microbial host cell.
4. The method of any one of embodiments 1 to 3, wherein the method further comprises the isolation of the polypeptide from the cell, and the purification of the polypeptide.
5. The method of embodiment 4, wherein the purification comprises the enrichment of polypeptides which do not comprise non-canonical branched-chain amino acids.
6. The method of embodiments 1 and 5, wherein said enzymatic activity is increased by introducing and expressing a polynucleotide encoding a polypeptide having said enzymatic activity in said microbial host cell.
7. The method of embodiment 6, wherein,
   - (a) the polynucleotide encodes a polypeptide having ketol-acid reductoisomerase (NADP(+)) activity (EC 1.1.1.86), and wherein
     - i) the polynucleotide comprises a nucleic acid sequence having at least 40% sequence identity to the nucleic acid sequence as shown in SEQ ID NO: 3, and/or
     - ii) the polynucleotide encodes a polypeptide comprising an amino acid sequence having at least 40% sequence identity to the amino acid sequence shown in SEQ ID NO: 4, or (b) the polynucleotide encodes a polypeptide having L-threonine dehydratase activity (EC 4.3.1.19), and wherein i) the polynucleotide comprises a nucleic acid sequence having at least 40% sequence identity to the nucleic acid sequence as shown in SEQ ID NO: 11, and/or ii) the polynucleotide encodes a polypeptide comprising an amino acid sequence having at least 40% sequence identity to the amino acid sequence shown in SEQ ID NO: 12.

8. The method of any one of embodiments 6 and 7, wherein said microbial host cell does not express an endogenous polypeptide having said enzymatic activity.

9. The method of any one of embodiments 1 to 8, wherein the polypeptide of interest is a therapeutic peptide or polypeptide.

10. The method of any one of embodiments 1 to 9, wherein the polynucleotide encoding the polypeptide of interest and/or the polynucleotide encoding the polypeptide having said enzymatic activity is operably linked to an inducible promoter.

11. The method of any one of embodiments 1 to 10, wherein said microbial host cell is an *Escherichia coli* cell.

12. A method for reducing misincorporation of at least one non-canonical branched-chain amino acid into a recombinant polypeptide of interest expressed in a microbial host cell, said method comprising (d) modulating an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase (EC 4.3.1.19) in the microbial host cell, (a) introducing a polynucleotide encoding the polypeptide of interest into said microbial host cell, and (b) expressing said polypeptide of interest in said microbial host cell.

13. The method of embodiment 12, wherein the at least one non-canonical branched-chain amino acid is selected from norvaline, norleucine and beta-methylnorleucine.

14. A microbial host cell comprising (a) a recombinant polynucleotide encoding a polypeptide of interest, and (c) a recombinant polynucleotide encoding a polypeptide having an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase (EC 4.3.1.19).

15. Use of a polypeptide having an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase (EC 4.3.1.19), or of a polynucleotide encoding said polypeptide for reducing misincorporation of at least one non-canonical branched-chain amino acid into a recombinant polypeptide of interest produced in a microbial host cell.

16. Use of a microbial host cell for producing a recombinant polypeptide of interest, wherein the microbial host cell has been modified such that an enzymatic activity selected from the group consisting of ketol-acid reductoisomerase (NADP(+)) activity (EC 1.1.1.86), acetohydroxyacid synthase activity (EC 2.2.1.6), aspartate kinase activity (EC 2.7.2.4), homoserine dehydrogenase activity (EC 1.1.1.3), and L-threonine dehydratase (EC 4.3.1.19) is modulated in said microbial host cell as compared to the enzymatic activity in an unmodified microbial host cell.

17. The method according to any one of embodiments 1 to 13, the microbial cell of embodiment 14, or the use of embodiments 15 or 16, wherein the enzymatic activity is modulated.

18. The method according to any one of embodiments 1 to 13 and 17, the microbial cell of embodiment 14 or 17, or the use of embodiments 15, 16 or 17, wherein the polypeptide of interest is a proinsulin.

FIGURES

FIG. 1: Plasmid map of pSW3_lacI$^+$, expressing mini-proinsulin. Plasmid pSW3_lacI$^+$ confers resistance to ampicillin and expresses an 11 kDa recombinant protein (mini-proinsulin) under the control of an IPTG inducible promoter. Plasmid also co-expresses the repressor LacI, which is under the control of a lacI$^+$ promoter variant. Generated with Snapgene®.

Figure 2:
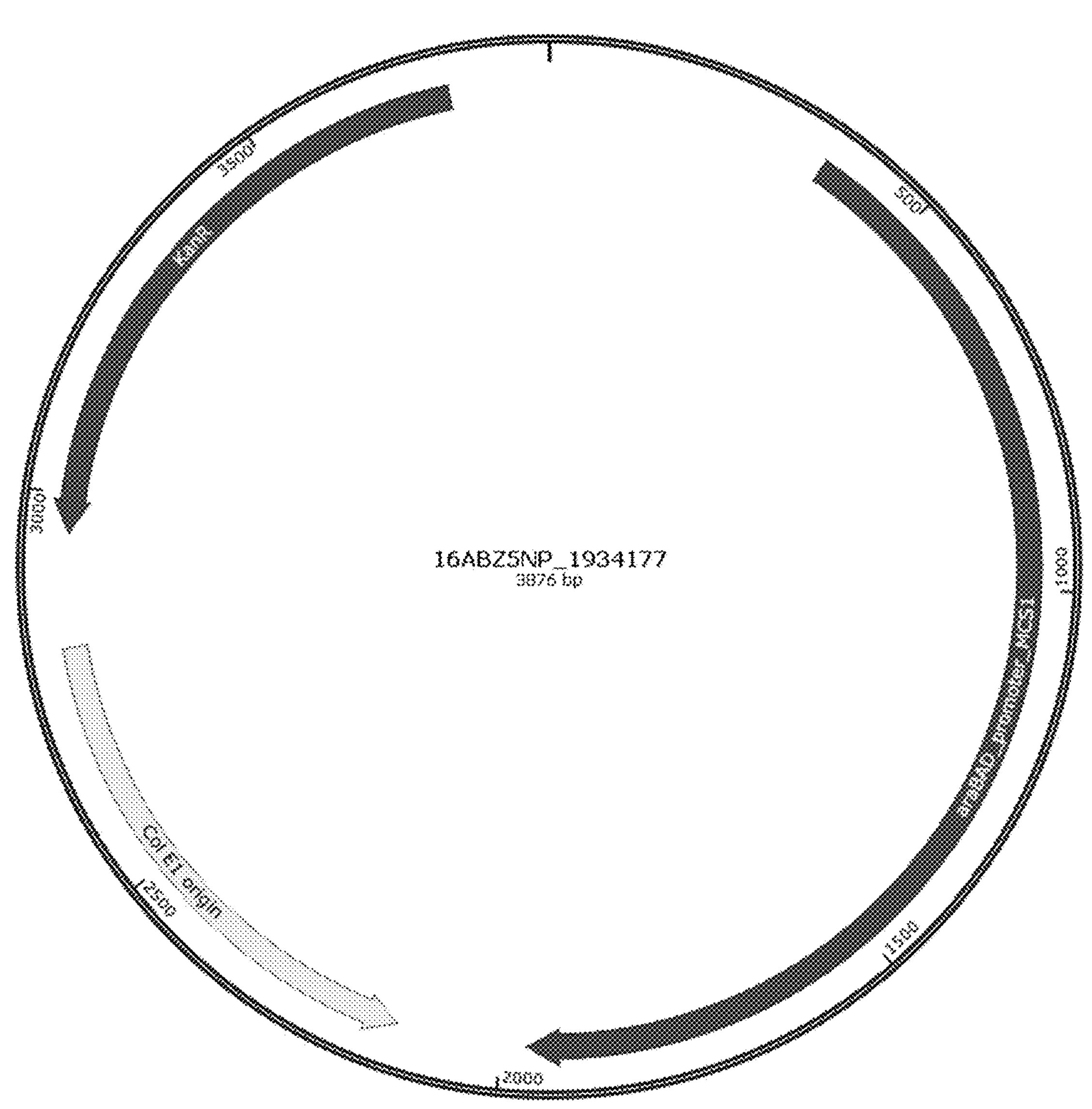

FIG. 2: Plasmid map of 16ABZ5NP_1934177, containing fragment 1. Generated with Snapgene®.

Figure 3:
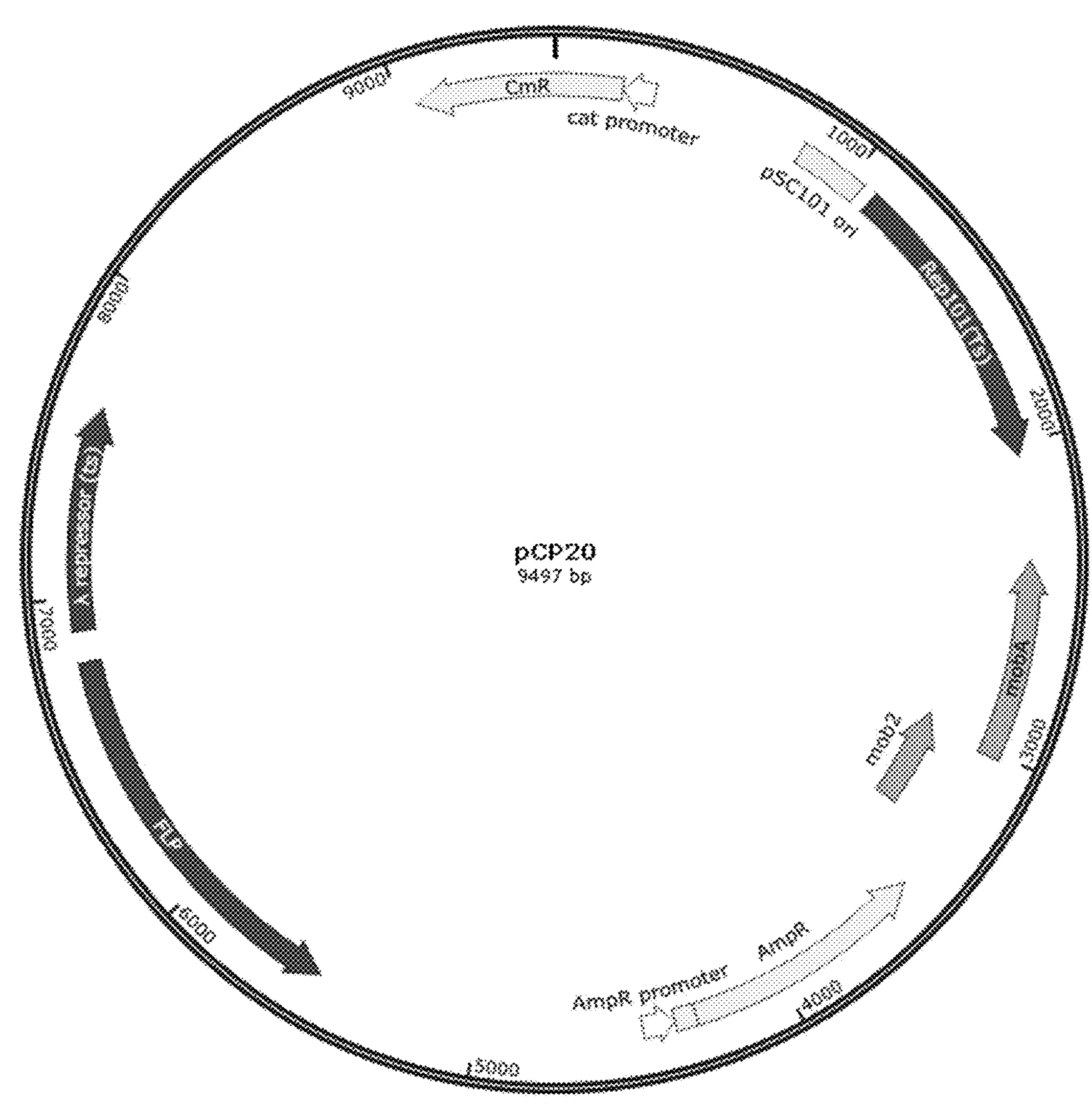

FIG. 3: Plasmid map of pCP20. Generated with Snapgene®.

Figure 4:
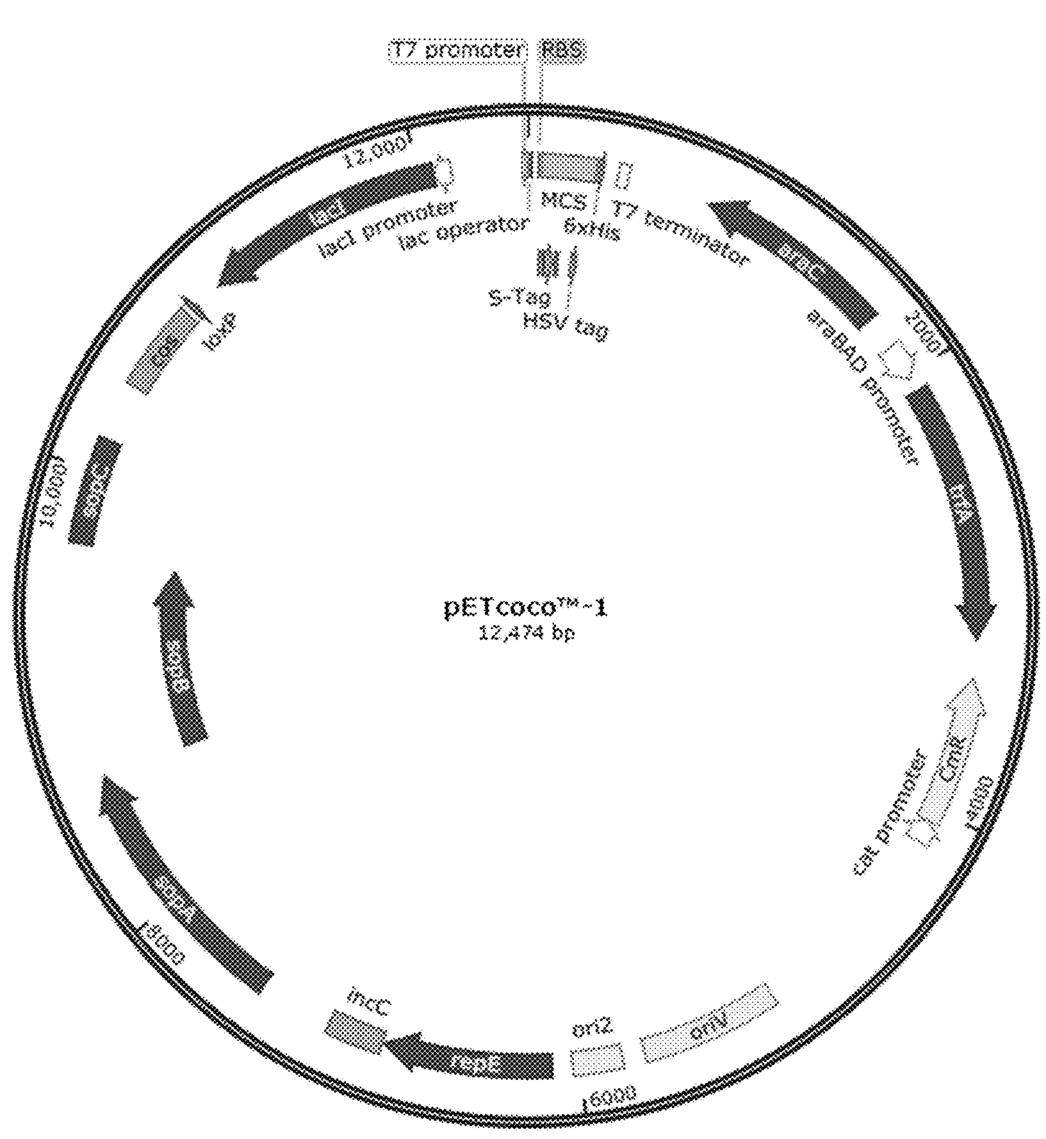

FIG. 4: Plasmid map of pETcoco1, including ori2 and its elements (repE, sopA, sopB, sopC). Generated with Snapgene®.

Figure 5:
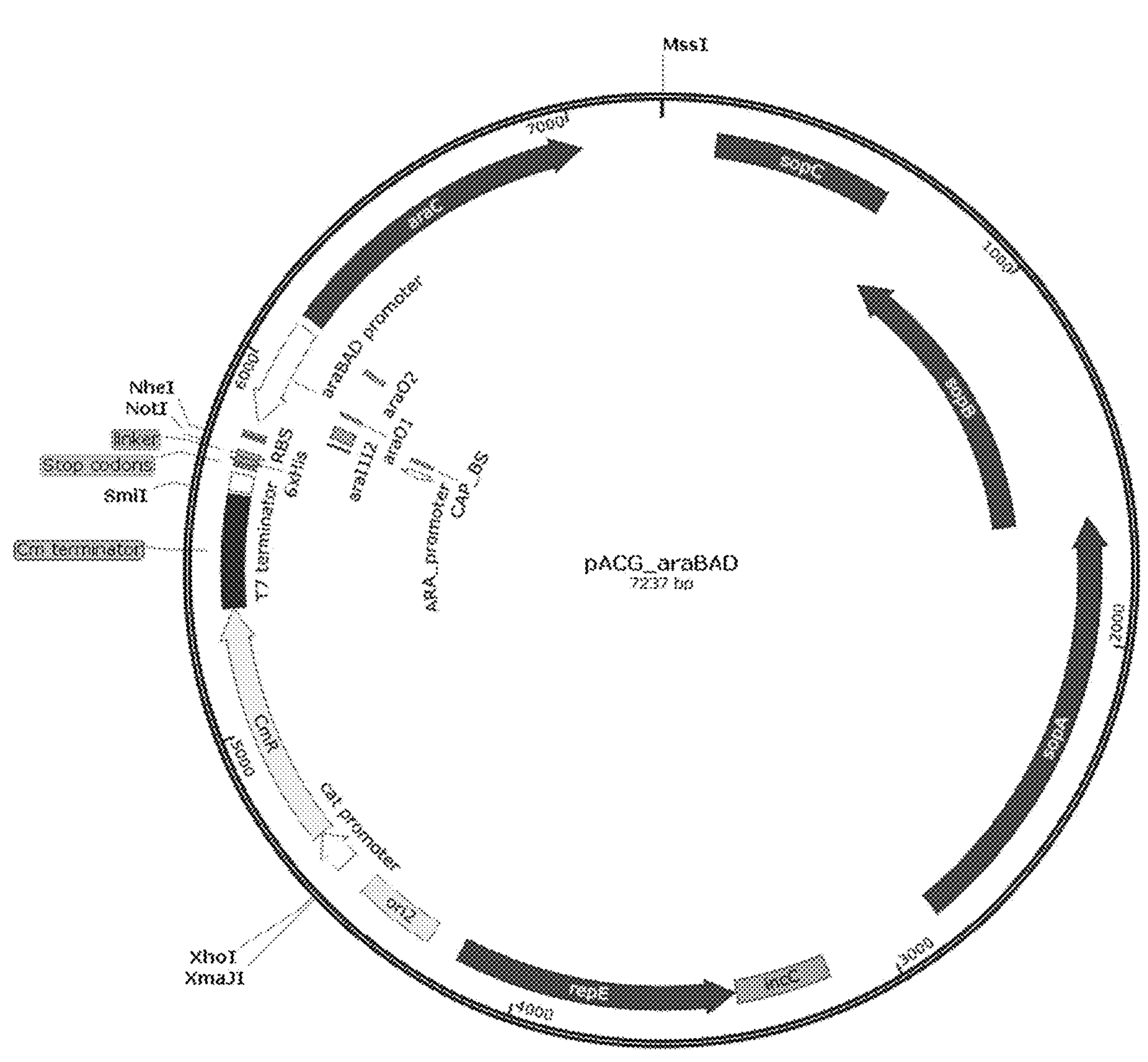

FIG. 5: Plasmid map of the arabinose-tunable plasmid pACG_araBAD. It includes ori2 and its elements (repE, sopA, sopB, sopC) which ensure 1 copy plasmid per cell. Plasmid confers resistance to chloramphenicol. Exogenous genes can be cloned by restriction cloning with enzymes NheI and NotI. Cloned genes are under the control of an arabinose promoter. AraC is necessary for the activation of the arabinose promoter and is also present in the plasmid. Additional unique restriction sites (SmiI, XhoI, XmaJI, MssI) are present in order to allow exchange of the origin of replication, antibiotic resistance marker and promoter region. Generated with Snapgene®.

Figure 6:
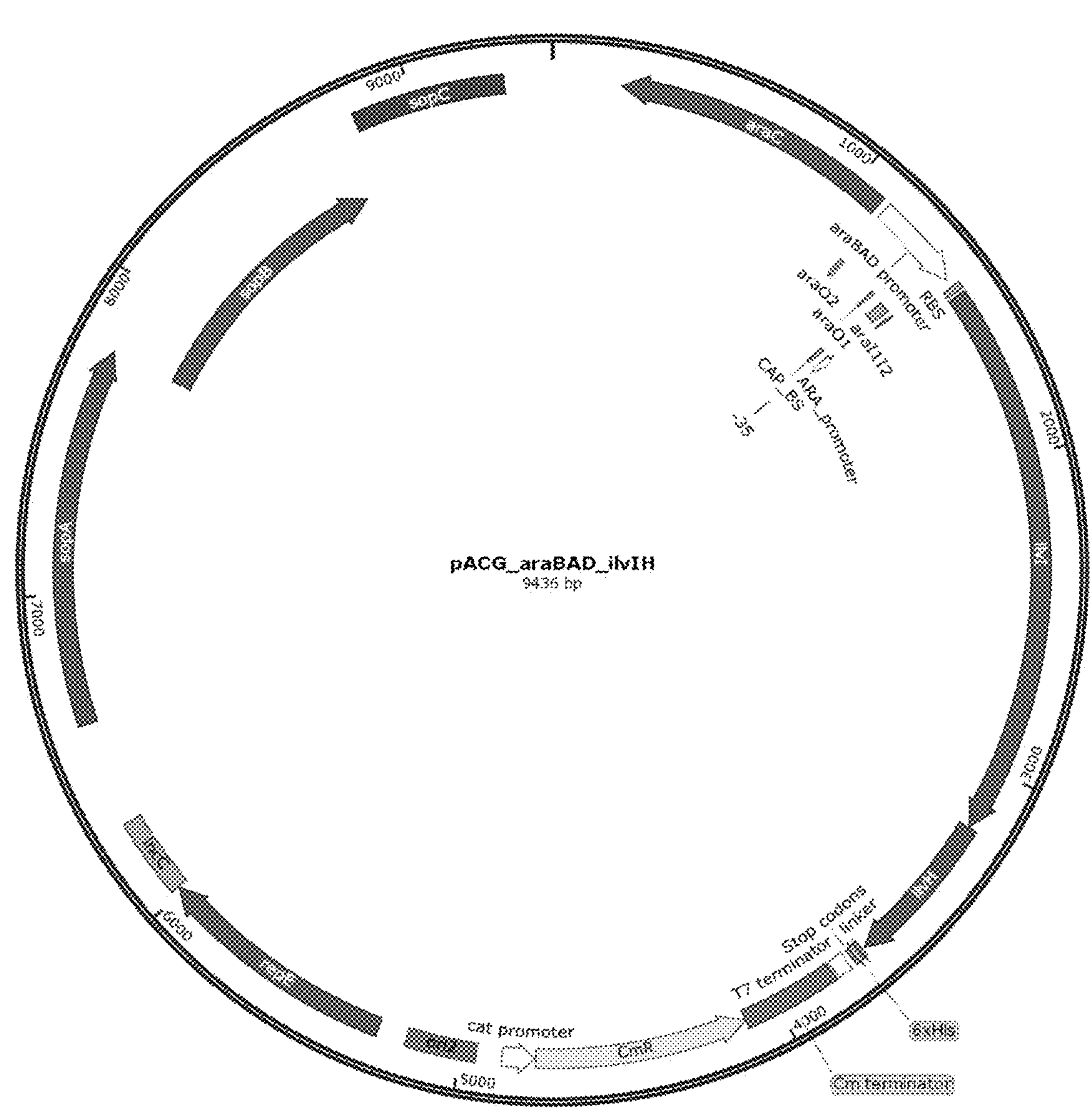

FIG. 6: Plasmid map of the arabinose-tunable plasmid pACG_araBAD_ilvIH. This plasmid results upon restriction cloning of gene ilvIH into the original pACG_araBAD plasmid with enzymes NheI and NotI. This plasmid allows regulation of ilvIH gene expression by addition of arabinose into the medium. Generated with Snapgene®.

Figure 7:
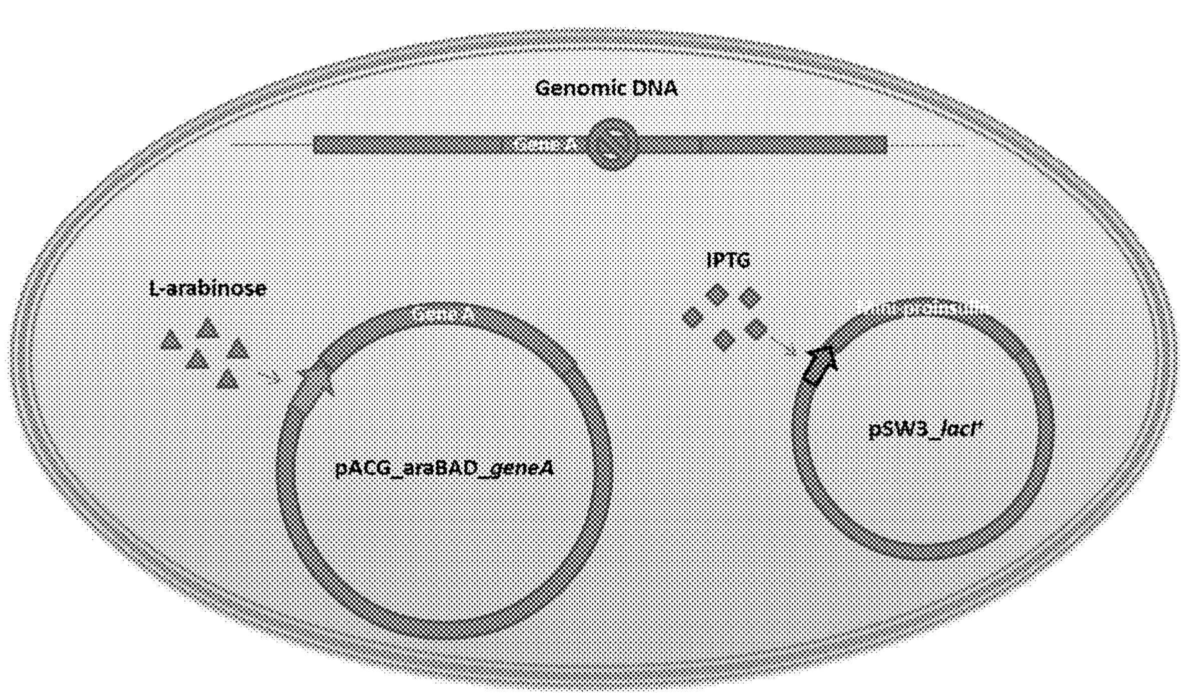

FIG. 7: Genetic modifications performed to wild type *E. coli* in this work. Genomic DNA contains a knock out of a certain gene (gene A). Expression of that gene can then be regulated by L-arabinose thanks to the presence of a tunable expression plasmid, containing such gene (pACG_araBAD_geneA). In addition, plasmid pSW3_lacI$^+$ expresses mini-proinsulin, which allows testing ncBCAA misincorporation.

Figure 8:
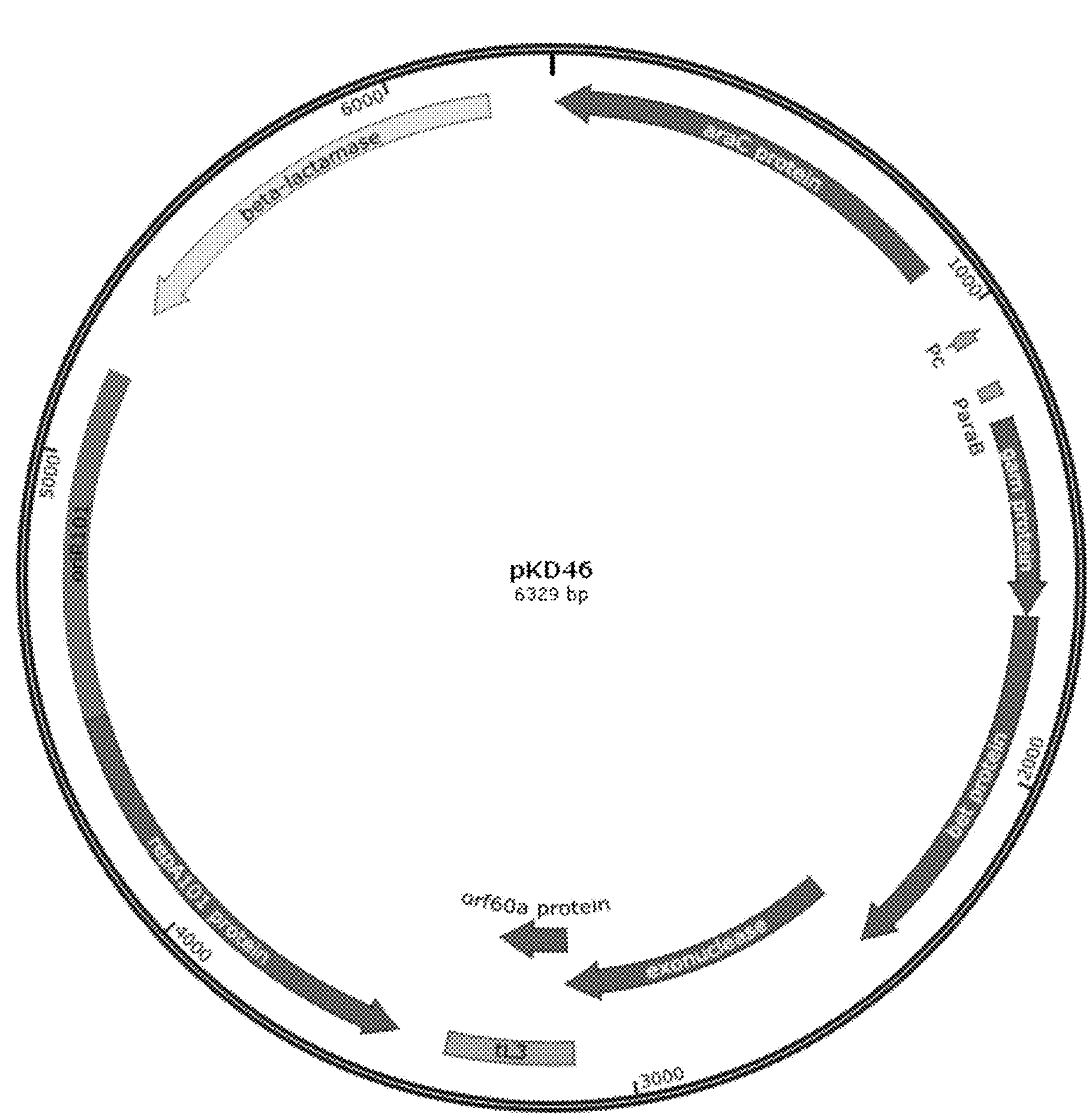

FIG. 8: Plasmid map of pKD46. Generated with Snapgene®.

Figure 9:
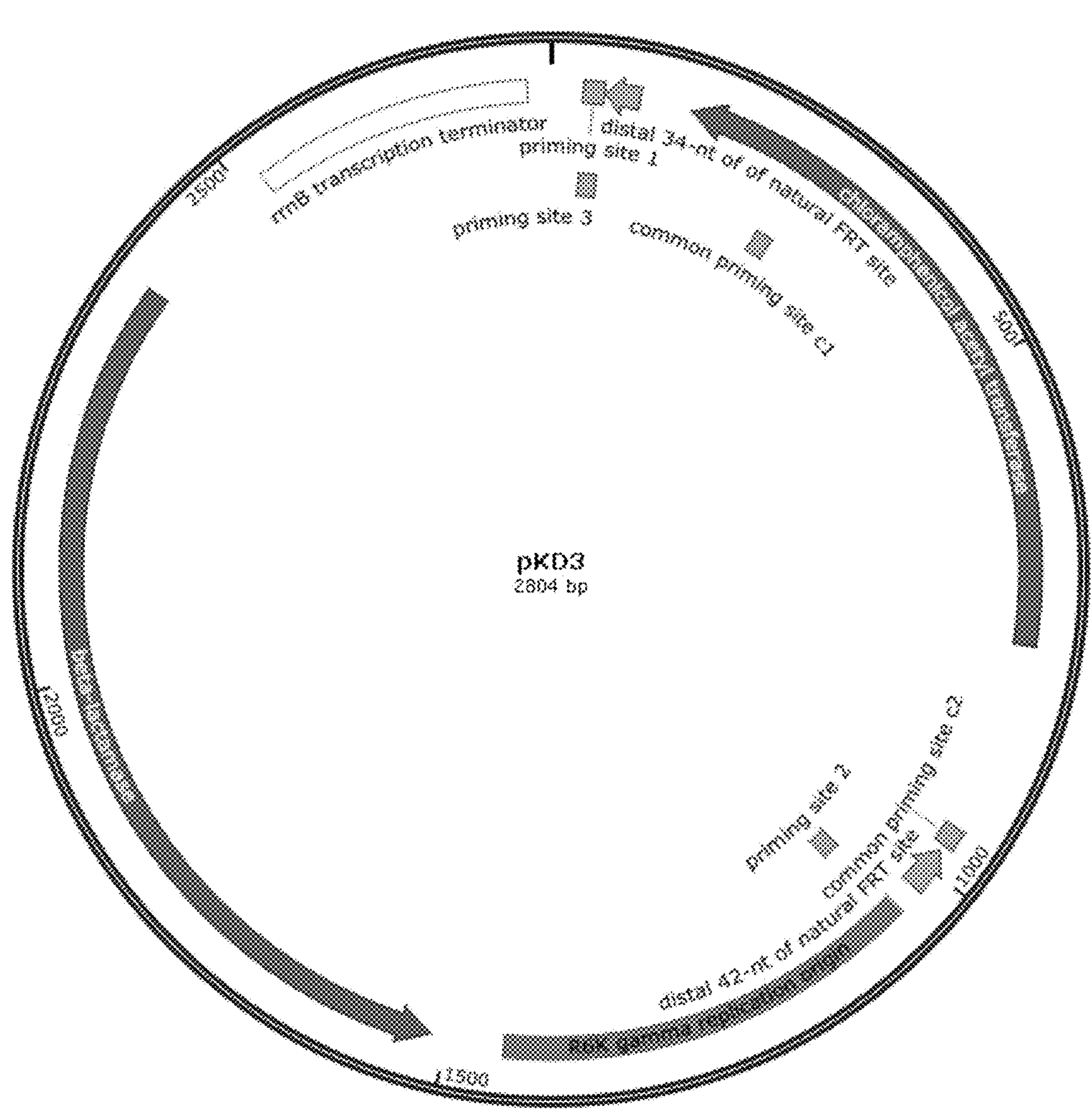

FIG. 9: Plasmid map of pKD3. Generated with Snapgene®.

Figure 10:
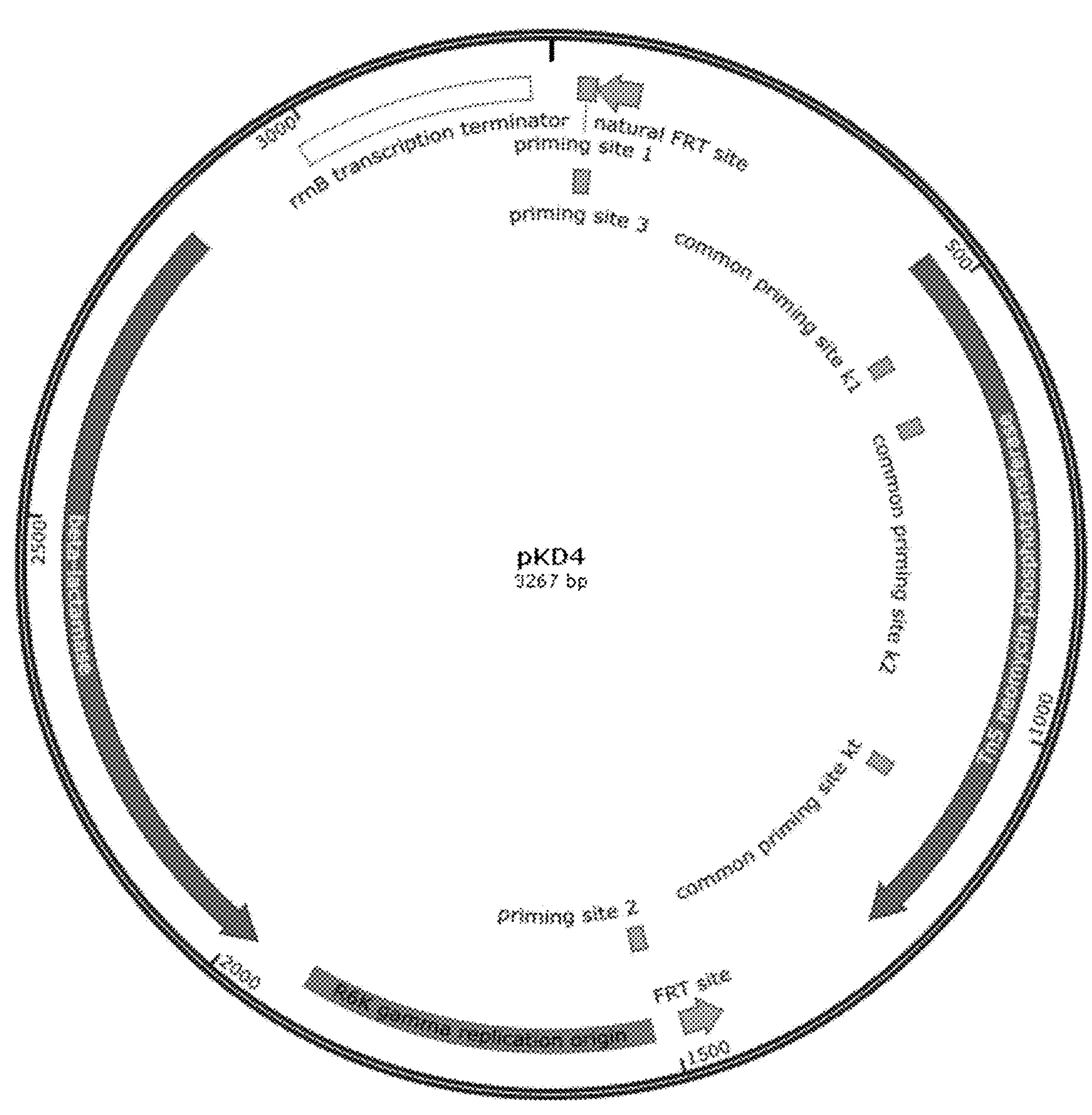

FIG. 10: Plasmid map of pKD4. Generated with Snapgene®.

Figure 11:
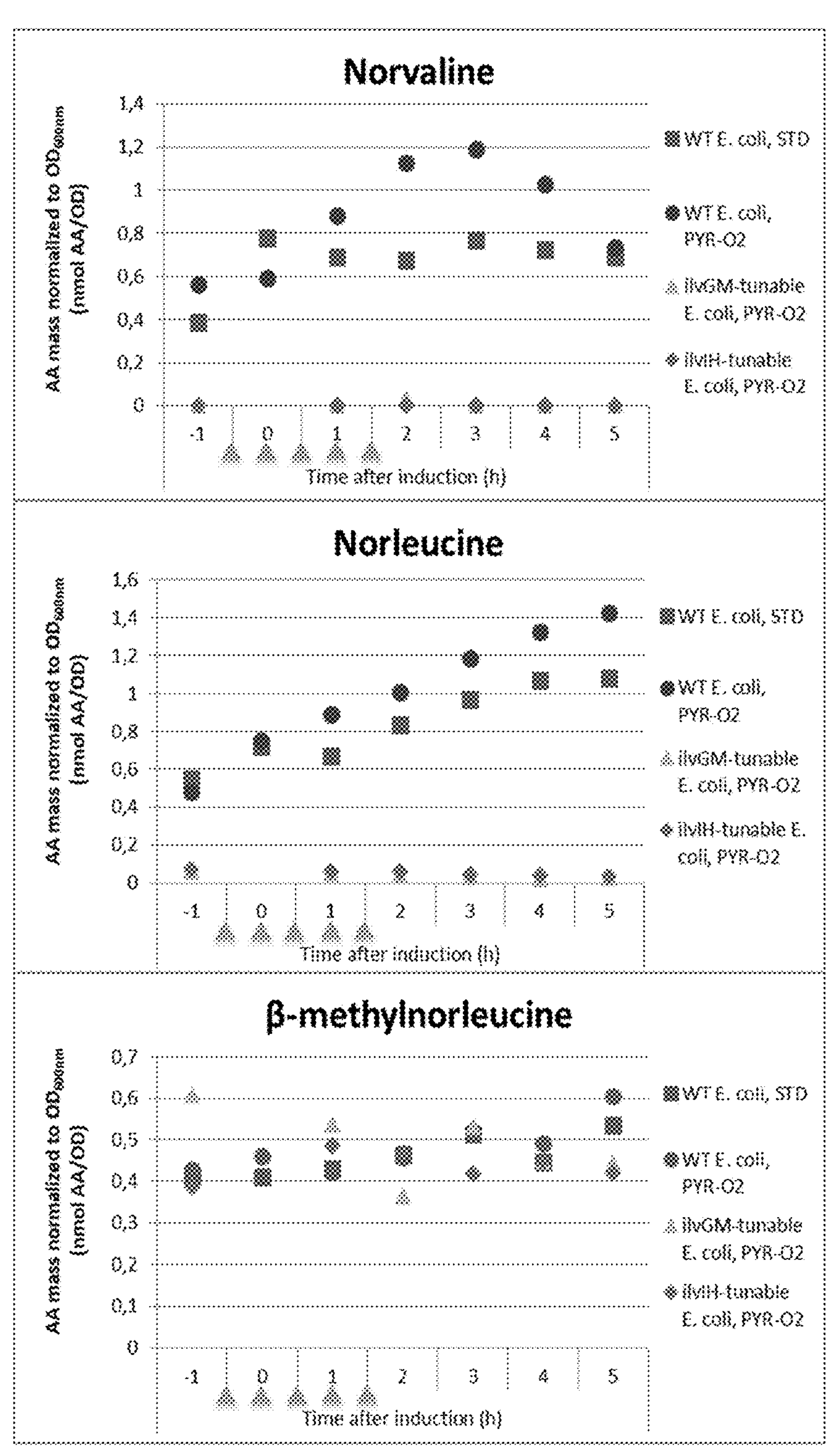

FIG. 11: Molar concentrations of norvaline (A), norleucine (B) and β-methylnorleucine (C) normalized to $OD_{600\ nm}$ present in the intracellular soluble protein fraction calculated over time after induction of different *E. coli* cultivations in a 15 L reactor under standard conditions (STD) and under conditions triggering ncBCAA accumulation, i.e. pyruvate pulsing and oxygen limitation (PYR-O2). Indicated in the legend, "WT *E. coli*" refers to the wild type strain *E. coli* K-12 BW25113 pSW3_lacI$^+$, "ilvGM-tunable *E. coli*" alludes to strain *E. coli* K-12 BW25113 pSW3_lacI$^+$ pACG_araBAD_ilvGM and "ilvIH-tunable *E. coli*" corresponds with strain *E. coli* K-12 BW25113 ΔilvIH pSW3_lacI+ pACG_araBAD_ilvIH. Arrows indicate time points where 1 g/L pyrvate pulse combined with 5 min $O_2$ limitation was applied.

Figure 12:
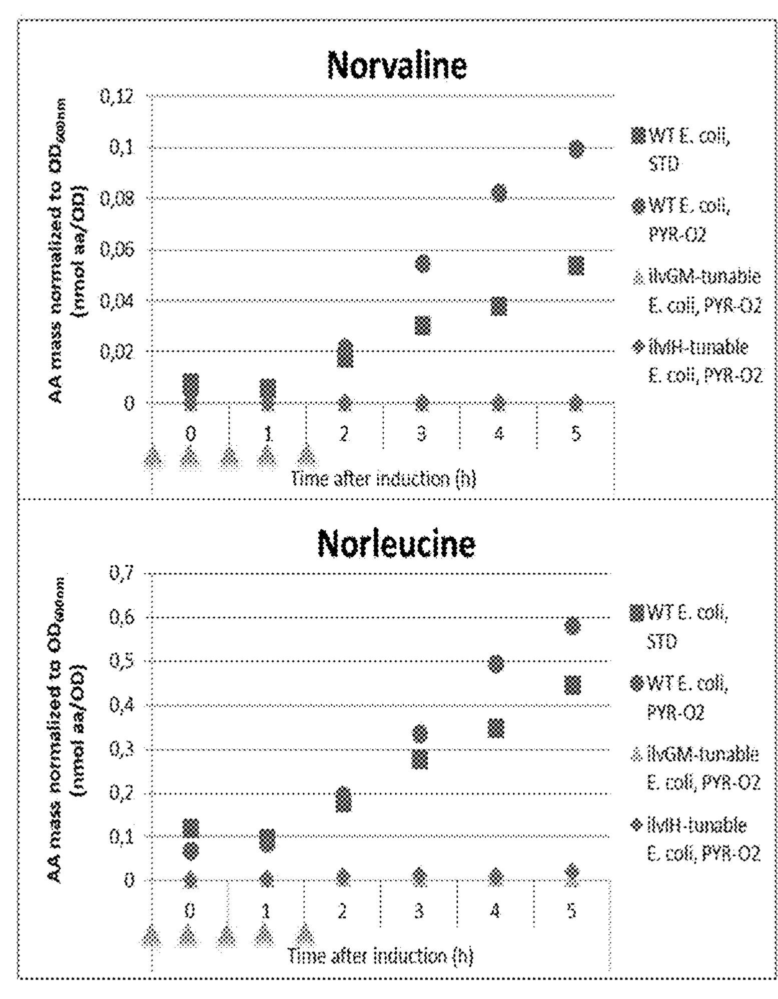

FIG. 12: Molar concentrations of norvaline (A) and norleucine (B) normalized to $OD_{600\ nm}$ present in the inclusion body fraction calculated over time after induction of different *E. coli* cultivations in a 15 L reactor under standard conditions (STD) and under cultivation conditions triggering ncBCAA accumulation, i.e. pyruvate pulsing and oxygen limitation (PYR-O2). Indicated in the legend, "WT *E. coli*" refers to the wild type strain *E. coli* K-12 BW25113 pSW3_lacI$^+$, "ilvGM-tunable *E. coli*" alludes to strain *E. coli* K-12 BW25113 pSW3_lacI$^+$ pACG_araBAD_ilvGM and "ilvIH-tunable *E. coli*" corresponds with strain *E. coli* K-12 BW25113 ΔilvIH pSW3_lacI+pACG_araBAD_ilvIH. Arrows indicate time points where 1 g/L pyruvate pulse combined with 5 min $O_2$ limitation was applied.

All references referred to above are herewith incorporated by reference with respect to their entire disclosure content as well as their specific disclosure content explicitly referred to in the above description.

The following examples merely illustrate the invention. They should not be construed as limiting the scope of protection in any way.

EXAMPLES

Example 1: Transformation of K12 BW25113 ΔthrA, ΔilvA, ΔilvC, ΔilvIH and ΔilvBN Mutants with Plasmid pSW3_lacI$^+$ ΔthrA, ΔilvA, ΔilvC Knock-outs Strain *E. coli* K12 BW25113 as well as single knock-out mutants *E. coli* K12 BW25113 ΔthrA, ΔilvA and ΔilvC were acquired from the *E. coli* Genetic Stock Center (CGSC) of Yale University. Those mutant strains belong to the so-called KEIO collection (Baba, T., Ara, T., Hasegawa, M., Takai, Y., Okumura, Y., Baba, M., . . . & Mori, H. (2006). Construction of *Escherichia coli* K-12 in-frame, single-gene knockout mutants: the Keio collection. Molecular systems biology, 2(1)). These strains contain plasmid pKD46 (FIG. 8) and a kanamycin resistance marker substituting target gene. CGSC identification for each acquired strain is indicated as follows:

| Strain | CGSC identification number |
|---|---|
| *E. coli* K12 BW25113 | 7636 |
| *E. coli* K12 BW25113 ΔthrA | JW0001-1 |
| *E. coli* K12 BW25113 ΔilvA | JW3745-2 |
| *E. coli* K12 BW25113 ΔilvC | JW3747-2 |

Plasmid pKD46 was curated from the acquired *E. coli* K12 BW25113 single knock-out mutants and the respective electrocompetent cells were transformed with pCP20 (FIG. 3), a temperature-sensitive plasmid encoding a flipase. Plasmid pCP20 was curated and removal of the antibiotic resistance marker from the mutants was tested by sequencing. The final respective electrocompetent *E. coli* K12 BW25113 mutants were transformed with pSW3_lacI$^+$ (FIG. 1), a high copy plasmid encoding mini-proinsulin.

ΔilvIH and ΔilvBN Knock-outs

The knock-out strains *E. coli* K12 BW25113 ΔilvIH and ΔilvBN were not acquired but manually generated. Procedure to generate *E. coli* knock-out mutants described at "Datsenko, K. A., & Wanner, B. L. (2000). One-step inactivation of chromosomal genes in *Escherichia coli* K-12 using PCR products. Proceedings of the National Academy of Sciences, 97(12), 6640-6645" was used as a reference. Electrocompetent *E. coli* K12 BW25113 cells were transformed with pKD46, a temperature-sensitive recombination helper plasmid. Knock-out mutants for the operons ilvIH and ilvBN were then generated by transformation of electrocompetent *E. coli* K12 BW25113 cells containing pKD46 with the respective deletion cassette, previously obtained by PCR from pKD3 (FIG. 9) or pKD4 (FIG. 10). PCR-based verification was carried out to test proper integration of the deletion cassette into the genome. Plasmid pKD46 was curated and the respective electrocompetent *E. coli* K12 BW25113 mutants were transformed with pCP20 (FIG. 3), a temperature-sensitive plasmid encoding a flipase. Plasmid pCP20 was curated and removal of the antibiotic resistance marker from the mutants was tested by sequencing. The final respective electrocompetent *E. coli* K12 BW25113 mutants were transformed with pSW3_lacI$^+$ (FIG. 1), a high copy plasmid encoding mini-proinsulin.

Example 2: Design and Generation of an araC-PBAD Tunable Expression Vector (pACG_araBAD)

An arabinose-based tunable expression plasmid, allowing regulation of genes of study, previously knocked-out, was obtained by the junction of 3 different DNA segments: Fragment 1 contains the araC-PBAD promoter region (Guzman et al., 1995, Tight regulation, modulation, and high-level expression by vectors containing the arabinose PBAD promoter. Journal of bacteriology, 177(14), 4121-4130), UTRs, T7 terminator, a cloning site allowing gene cloning with rare-cutting restriction enzymes NheI and NotI and a C-terminal 6×his-tag sequence allowing expression of fusion proteins. Fragment 2 contains a chloramphenicol resistance cassette while fragment 3 includes the ori2 origin of replication and genes sopA, sopB, sopC and repE.

Fragment 1 was chemically synthesized and subsequently cloned in plasmid 16ABZ5NP_1934177 (FIG. 2). Fragment 1 was then amplified by PCR from plasmid 16ABZ5NP_1934177. Fragments 2 and 3 were directly amplified by PCR from plasmids pCP20 (FIG. 3) and pETcoco1 (FIG. 4), respectively. The three DNA segments were joined together according to the In-Fusion cloning strategy (Takara Bio USA; Ref.: 639649) to generate plasmid pACG_araBAD (FIG. 5).

Example 3: Cloning of the Target Genes into the Tunable Expression Vectors

Genes of study (ilvA, ilvC, ilvIH, ilvBN, and thrA) were amplified by PCR from the *E. coli* K12 BW25113 genomic DNA and they were subsequently cloned into the previously generated tunable expression plasmid (FIG. 5) by using restriction enzymes NheI and NotI. ilvGM was amplified from an *E. coli* strain where ilvG was not mutated. As example, plasmid map of the resulting arabinose-tunable plasmid pACG_araBAD_ilvIH is shown in FIG. 6.

Example 4: Transformation of the Tunable Expression Vectors with Cloned Genes into the Respective Mutant Containing pSW3_lacI$^+$ The final respective electrocompetent *E. coli* K12 BW25113 mutants containing pSW3_lacI$^+$ were transformed with the tunable expression plasmid expressing the corresponding gene of study.

After all genetic modifications, the generated *E. coli* mutant strains look like as described in FIG. 7. A total of 6 *E. coli* mutant strains were then generated:

- *E. coli* K12 BW25113 ΔilvC expressing pSW3_lacI$^+$ and pACG_araBAD_ilvC
- *E. coli* K12 BW25113 ΔilvIH expressing pSW3_lacI$^+$ and pACG_araBAD_ilvIH
- *E. coli* K12 BW25113 ΔilvBN expressing pSW3_lacI$^+$ and pACG_araBAD_ilvBN
- *E. coli* K12 BW25113 ΔthrA expressing pSW3_lacI$^+$ and pACG_araBAD_thrA
- *E. coli* K12 BW25113 ΔilvA expressing pSW3_lacI$^+$ and pACG_araBAD_ilvA
- *E. coli* K12 BW25113 expressing pSW3_lacI$^+$ and pACG_araBAD_ilvGM Example 5: Evaluation of L-Arabinose Induction Effect on Cell Growth of Mutant *E. coli* Strains The aim of this experiment was to evaluate the effect of addition of different concentrations of L-arabinose on the expression of genes under the control of the araBAD promoter and, as a consequence, the effect on cell growth of the generated mutant *E. coli* strains.

*E. coli* cells were grown in a defined mineral salt medium containing (per L): 0.67 g $Na_2SO_4$, 0.82 g $(NH_4)_2SO_4$, 0.17 g $NH_4Cl$, 4.87 g $K_2HPO_4$, 1.2 g $NaH_2PO_4 \times 2H_2O$ and 0.33 g $(NH_4)_2$—H-citrate. The medium was supplemented with 0.67 ml/L trace elements solution and 0.67 ml/L $MgSO_4$ solution (1.0 M). The trace element solution comprised (per L): 0.5 g $CaCl_2)\times 2H_2O$, 0.18 g $ZnSO_4 \times 7H_2O$, 0.1 g $MnSO_4 \times H_2O$, 16.7 g $FeCl_3 \times 6H_2O$, 0.16 g $CuSO_4 \times 5H_2O$, 0.18 g $CoCl_2 \times 6H_2O$. Additionally, a 0.1 M Na-Phosphate buffer was used for further buffering of the medium.

In order to generate the cultivation, 50 μL of a cryostock containing the corresponding *E. coli* strain were used to inoculate 5 mL of supplemented defined mineral salt medium containing 5 g/L glucose, 100 g/mL ampicillin, 25 μg/mL chloramphenicol (only for mutant *E. coli* strains) and a given concentration of L-arabinose. The cultivation was incubated at 37° C. and 220 rpm in an orbital shaker for 15 h. At the end of the process, $OD_{600\ nm}$ was measured for each cultivation. Following table summarizes results obtained:

| Tested strain | L-arabinose concentration (%) | $OD_{600nm}$ |
|---|---|---|
| *E. coli* K12 BW25113 ΔilvC | 0 | 0.21 |
| pSW3_lacI$^+$ | 0.05 | 0.32 |
| pACG_araBAD_ilvC | 0.1 | 0.64 |
| | 0.4 | 2.34 |
| | 1.6 | 2.42 |
| *E. coli* K12 BW25113 ΔthrA | 0 | 0.16 |
| pSW3_lacI$^+$ | 0.05 | 0.17 |
| pACG_araBAD_thrA | 0.2 | 0.37 |
| | 0.4 | 2.88 |
| | 0.8 | 2.79 |
| | 1.6 | 2.69 |
| *E. coli* K12 BW25113 ΔilvA | 0 | 0.14 |
| pSW3_lacI$^+$ | 0.025 | 0.78 |
| pACG_araBAD_ilvA | 0.05 | 2.95 |
| | 0.2 | 2.83 |
| | 0.8 | 2.62 |
| | 1.6 | 2.61 |
| *E. coli* K12 BW25113 ΔilvIH | 0 | 2.84 |
| pSW3_lacI$^+$ | 0.025 | 3.03 |
| pACG_araBAD_ilvIH | 0.05 | 3.08 |
| | 0.2 | 3.03 |
| | 0.8 | 2.43 |
| | 1.6 | 2.77 |
| *E. coli* K12 BW25113 ΔilvBN | 0 | 2.66 |
| pSW3_lacI$^+$ | 0.025 | 2.66 |
| pACG_araBAD_ilvBN | 0.05 | 2.65 |
| | 0.2 | 2.96 |
| | 0.8 | 2.80 |
| | 1.6 | 2.66 |
| *E. coli* K12 BW25113 | 0 | 3.10 |
| pSW3_lacI$^+$ | 0.025 | 3.05 |
| pACG_araBAD_ilvGM | 0.05 | 3.17 |
| | 0.2 | 3.01 |
| | 0.8 | 2.65 |
| | 1.6 | 2.93 |
| *E. coli* K12 BW25113 | 0 | 3.10 |
| pSW3_lacI$^+$ | | |

Example 6: Cultivation Conditions for Evaluation of L-Arabinose Induction Effect on ncBCAA Production in Mutant *E. coli* Strains at Mini-Bioreactor Level Cultivation Medium

*E. coli* cells were grown in a defined mineral salt medium containing (per L): 0.67 g $Na_2SO_4$, 0.82 g $(NH_4)_2SO_4$, 0.17 g $NH_4Cl$, 4.87 g $K_2HPO_4$, 1.2 g $NaH_2PO_4 \times 2H_2O$ and 0.33 g $(NH_4)_2$—H-citrate. The medium was supplemented with 0.67 ml/L trace elements solution and 0.67 ml/L $MgSO_4$ solution (1.0 M). The trace element solution comprised (per L): 0.5 g $CaCl_2)\times 2H_2O$, 0.18 g $ZnSO_4 \times 7H_2O$, 0.1 g $MnSO_4 \times H_2O$, 16.7 g $FeCl_3 \times 6H_2O$, 0.16 g $CuSO_4 \times 5H_2O$, 0.18 g $CoCl_2 \times 6H_2O$. Additionally, a 0.1 M Na-Phosphate buffer was used for further buffering of the medium.

Pre-cultivation

30 μL of a cryostock containing the corresponding *E. coli* strain were used to inoculate 30 mL of supplemented defined mineral salt medium containing 5 g/L glucose, 100 μg/mL ampicillin and 25 μg/mL chloramphenicol (only for mutant *E. coli* strains) in order to generate the pre-cultivation. For each mutant *E. coli* strain, medium also contained the minimum L-arabinose concentration necessary to recover the cell growth of the non-engineered strain, which was previously tested in Example 5. The pre-cultivation was incubated at 37° C. and 220 rpm in an orbital shaker, overnight.

Main Cultivation $OD_{600\ nm}$ at the end of the pre-cultivation was measured and a given volume was used to inoculate a 5 mL starting volume Pall Micro24 mini-bioreactor (Microreactor Technologies Inc.) so that initial $OD_{600\ nm}$ was 0.4. The mini-reactor medium consisted of supplemented defined mineral salt medium containing 4 g/L glucose, 100 μg/mL ampicillin, 25 μg/mL chloramphenicol (only for mutant *E. coli* strains) and 1 μL/mL Desmophen antifoam. Medium was also supplemented with different concentrations of L-arabinose. Cultivation was carried out at 37° C. and the pH was maintained at 7 by automatic control with $NH_4OH$ and $CO_2$. Stirrer speed was set to 800 rpm and DO set-point to 25%, maintaining the last by automatically increasing the oxygen flow into the mini-reactor. Batch phase lasted around 4 h. After batch phase was finished, 1 mL 400 g/L EnPump 200 solution and 50 μL 3000 U/L amylase solution were manually added into the mini-reactor, hence starting the fed-batch phase. EnPump 200 is a glucose polymer and when amylase is present, it constantly hydrolyses the polymer, thus delivering free glucose molecules over time, ensuring then a glucose-limited fermentation. 30 min after beginning of the fed batch phase, recombinant protein expression was induced by manual addition of an IPTG pulse to a final concentration of 0.5 mM. Fed-batch phase was active for 3.5 h.

Example 7: Amino Acid Analysis

Intracellular soluble protein fraction and inclusion body fraction were isolated from cell extracts according to protocol provided in "BugBuster Protein Extraction Reagent" kit (Merck, Cat. Nr.: 70584-4). 250 μL of the isolated intracellular soluble protein fraction were mixed with 750 μL 5M HCl. Isolated inclusion body pellets were resuspended with 200 μL $dH_2O$ and 100 μL of the resulting inclusion body suspension were mixed with 900 μL 5M HCl. Resulting solutions were introduced in crystal vials with screw caps and vials were incubated closed for 24 h at 80° C. for acid hydrolysis. Afterwards, vials were left opened in a heating block for 16-24 h at 65° C. while rotating until all liquid was evaporated. Amino acid isolation from dried hydrolyzed samples was performed according to protocol provided in "EZ:faast™ for free (physiological) amino acid analysis by GC-FID" kit (Phenomenex, Cat. Nr.:KG0-7165). After isolation process, around 120 μL of the resulting upper layer were introduced into GC vials and 2 μL were then injected into the GC analyzer. The GC was run according to following oven conditions: equilibration time of 0.5 min, 110° C. for 1 min, 30° C./min heating up to 320° C. and then 320° C. for 1 min. Nitrogen was used as a carrier gas with a constant flow rate of 1.5 mL/min. Injection was carried out with a 1:15 split ratio at 250° C.

Example 8: Evaluation of L-Arabinose Induction Effect on ncBCAA Production in Mutant *E. coli* Strains at Mini-Bioreactor Level Following tables summarize experimental results for each tested protein fraction, ncBCAA and mutant strain under different concentrations of L-arabinose. Bold data presented in tables correspond to the concentration of a given ncBCAA in the *E. coli* BW25113 pSW3_lacI⁺ control strain. Data in percentage format shown in tables correspond to the variation percentage of the ncBCAA concentration obtained in the mutant strain under a given concentration of L-arabinose with respect to ncBCAA concentration obtained for the *E. coli* BW25113 pSW3_lacI⁺ control strain.

Inclusion Body Fraction

A) Norvaline

| *E. coli* BW25113 pSW3_lacI⁺ 0.026 (nmol aa/$OD_{600nm}$) | *E. coli* BW25113 ΔilvC pSW3_lacI⁺ pACG_araBAD_ilvC |
|---|---|
| 0.4% L-ara | 6.8% |
| 0.8% L-ara | −1.2% |
| 1.6% L-ara | −21.5% |

| *E. coli* BW25113 pSW3_lacI⁺ 0.036 (nmol aa/$OD_{600nm}$) | *E. coli* BW25113 ΔthrA pSW3_lacI⁺ pACG_araBAD_thrA |
|---|---|
| 0.4% L-ara | −36.4% |
| 0.8% L-ara | −44.9% |
| 1.6% L-ara | −40.6% |

| *E. coli* BW25113 pSW3_lacI⁺ 0.023 (nmol aa/$OD_{600nm}$) | *E. coli* BW25113 ΔilvIH pSW3_lacI⁺ pACG_araBAD_ilvIH | *E. coli* BW25113 ΔilvA pSW3_lacI⁺ pACG_araBAD_ilvA | *E. coli* BW25113 ΔilvBN pSW3_lacI⁺ pACG_araBAD_ilvBN | *E. coli* BW25113 pSW3_lacI⁺ pACG_araBAD_ilvGM |
|---|---|---|---|---|
| 0.05% L-ara | −12.3% | −7.6% | 2.7% | −61.8% |
| 0.2% L-ara | — | 4.5% | 48.3% | −56.0% |
| 0.8% L-ara | −40.7% | −17.1% | 62.9% | −58.4% |

For strains *E. coli* BW25113 ΔilvC pSW3_lacI⁺ pACG_araBAD_ilvC and *E. coli* BW25113 ΔilvIH pSW3_lacI⁺ pACG_araBAD_ilvIH, norvaline concentration significantly decreases when adding increasing concentrations of L-arabinose into the medium. The opposite behavior is observed for strain *E. coli* BW25113 ΔilvBN pSW3_lacI⁺ pACG_araBAD_ilvBN. For strains *E. coli* BW25113 ΔthrA pSW3_lacI⁺ pACG_araBAD_thrA and *E. coli* BW25113 pSW3_lacI⁺ pACG_araBAD_ilvGM, norvaline concentration shows a significant reduction but effect of increasing L-arabinose concentrations does not show a clear trend on variation of norvaline concentration. For strain *E. coli* BW25113 ΔilvA pSW3_lacI⁺ pACG_araBAD_ilvA no significant reduction of norvaline concentration was reported and effect of increasing L-arabinose concentrations does not seem to show a clear trend on variation of norvaline concentration.

B) Norleucine

| *E. coli* BW25113 pSW3_lacI+ 0.091 (nmol aa/$OD_{600nm}$) | *E. coli* BW25113 ΔilvC pSW3_lacI+ pACG_araBAD_ilvC |
|---|---|
| 0.4% L-ara | 71.9% |
| 0.8% L-ara | 8.7% |
| 1.6% L-ara | −24.3% |
| *E. coli*BW25113 pSW3_lacI+ 0.237 (nmol aa/$OD_{600nm}$) | *E. coli*BW25113 ΔthrA pSW3_lacI+ pACG_araBAD_thrA |
| 0.4% L-ara | −57.2% |
| 0.8% L-ara | −58.4% |
| 1.6% L-ara | −60.3% |

| *E. coli* BW25113 psW3_lacI+ 0.060 (nmol aa/$OD_{600nm}$) | *E. coli* BW25113 ΔilvIH pSW3_lacI+ pACG_araBAD_ ilvIH | *E. coli* BW25113 ΔilvA pSW3_lacI+ pACG_araBAD_ ilvA | *E. coli* BW25113 ΔilvBN pSW3_lacI+ pACG_araBAD_ ilvBN | *E. coli* BW25113 pSW3_lacI+ pACG_araBAD_ ilvGM |
|---|---|---|---|---|
| 0.05% L-ara | −4.2% | −22.3% | 67.4% | −100.0% |
| 0.2% L-ara | — | 16.9% | 132.2% | −88.5% |
| 0.8% L-ara | −70.8% | −10.5% | 245.9% | −100.0% |

For strains *E. coli* BW25113 ΔilvC pSW3_lacI+ pACG_araBAD_ilvC and *E. coli* BW25113 ΔilvIH pSW3_lacI+ pACG_araBAD_ilvIH, norleucine concentration significantly decreases when adding increasing concentrations of L-arabinose into the medium. The opposite behavior is observed for strain *E. coli* BW25113 ΔilvBN pSW3_lacI+ pACG_araBAD_ilvBN. For strains *E. coli* BW25113 ΔthrA pSW3_lacI+ pACG_araBAD_thrA and *E. coli* BW25113 pSW3_lacI+ pACG_araBAD_ilvGM, norleucine concentration shows a significant reduction but effect of increasing L-arabinose concentrations does not seem to show a clear trend on variation of norleucine concentration. For strain *E. coli* BW25113 ΔilvA pSW3_lacI+ pACG_araBAD_ilvA no significant reduction of norleucine concentration was reported and effect of increasing L-arabinose concentrations does not seem to have a clear effect on variation of norleucine concentration.

Intracellular Soluble Protein Fraction

A) Norvaline

| *E. coli* BW25113 pSW3_lacI+ 0.300 (nmol aa/$OD_{600nm}$) | *E. coli* BW25113 ΔilvC pSW3_lacI+ pACG_araBAD_ilvC |
|---|---|
| 0.4% L-ara | −22.0% |
| 0.8% L-ara | −36.0% |
| 1.6% L-ara | −39.5% |

| *E. coli* BW25113 pSW3_lacI+ 0.253 (nmol aa/$OD_{600nm}$) | *E. coli* BW25113 ΔthrA pSW3_lacI+ pACG_araBAD_thrA |
|---|---|
| 0.4% L-ara | −41.3% |
| 0.8% L-ara | −44.3% |
| 1.6% L-ara | −41.6% |

| *E. coli* BW25113 psW3_lacI+ 0.529 (nmol aa/$OD_{600nm}$) | *E. coli* BW25113 ΔilvIH pSW3_lacI+ pACG_araBAD_ ilvIH | *E. coli* BW25113 ΔilvA pSW3_lacI+ pACG_araBAD_ ilvA | *E. coli* BW25113 ΔilvBN pSW3_lacI+ pACG_araBAD_ ilvBN | *E. coli* BW25113 pSW3_lacI+ pACG_araBAD_ ilvGM |
|---|---|---|---|---|
| 0.05% L-ara | −53.1% | −19.5% | −2.2% | −71.9% |
| 0.2% L-ara | — | −23.9% | 23.5% | −73.0% |
| 0.8% L-ara | −63.6% | −20.8% | 211.4% | −75.9% |

For strains *E. coli* BW25113 ΔilvC pSW3_lacI+ pACG_araBAD_ilvC and *E. coli* BW25113 ΔilvIH pSW3_lacI+ pACG_araBAD_ilvIH, norvaline concentration decreases when adding increasing concentrations of L-arabinose into the medium. The opposite behavior is observed for strain *E. coli* BW25113 ΔilvBN pSW3_lacI+ pACG_araBAD_ilvBN. For strains *E. coli* BW25113 ΔthrA pSW3_lacI+ pACG_araBAD_thrA, *E. coli* BW25113 ΔilvA pSW3_lacI+ pACG_araBAD_ilvA and *E. coli* BW25113 pSW3_lacI+ pACG_araBAD_ilvGM, norvaline concentration shows a significant reduction but effect of increasing L-arabinose concentrations does not seem to show a clear trend on variation of norvaline concentration.

B) Norleucine

| *E. coli* BW25113 pSW3_lacI+ 0.180 (nmol aa/$OD_{600nm}$) | *E. coli* BW25113 ΔilvC pSW3_lacI+ pACG_araBAD_ilvC |
|---|---|
| 0.4% L-ara | 154.8% |
| 0.8% L-ara | 42.5% |
| 1.6% L-ara | 2.8% |

| *E. coli* BW25113 pSW3_lacI+ 0.304 (nmol aa/$OD_{600nm}$) | *E. coli* BW25113 ΔthrA pSW3_lacI+ pACG_araBAD_thrA |
|---|---|
| 0.4% L-ara | −30.1% |
| 0.8% L-ara | −26.6% |
| 1.6% L-ara | −36.4% |

| *E. coli* BW25113 pSW3_lacI+ 0.241 (nmol aa/$OD_{600nm}$) | *E. coli* BW25113 ΔilvIH pSW3_lacI+ pACG_araBAD_ilvIH | *E. coli* BW25113 ΔilvA pSW3_lacI+ pACG_araBAD_ilvA | *E. coli* BW25113 ΔilvBN pSW3_lacI+ pACG_araBAD_vilBN | *E. coli* BW25113 pSW3_lacI+ pACG_araBAD_ilvGM |
|---|---|---|---|---|
| 0.05% L-ara | −17.8% | −58.5% | 2.8% | −100.0% |
| 0.2% L-ara | — | −56.1% | 36.6% | −81.3% |
| 0.8% L-ara | −69.9% | −54.7% | 127.5% | −100.0% |

For strains *E. coli* BW25113 ΔilvC pSW3_lacI+ pACG_araBAD_ilvC and *E. coli* BW25113 ΔilvIH pSW3_lacI+ pACG_araBAD_ilvIH, norleucine concentration decreases when adding increasing concentrations of L-arabinose into the medium. The opposite behavior is observed for strain *E. coli* BW25113 ΔilvBN pSW3_lacI+ pACG_araBAD_ilvBN. For strains *E. coli* BW25113 ΔthrA pSW3_lacI+ pACG_araBAD_thrA, *E. coli* BW25113 ΔilvA pSW3_lacI+ pACG_araBAD_ilvA and *E. coli* BW25113 pSW3_lacI+ pACG_araBAD_ilvGM, norleucine concentration shows a significant reduction but L-arabinose concentration does not seem to have a clear effect on norleucine concentration.

C) β-methylnorleucine

| *E. coli* BW25113 pSW3_lacI+ 0.459 (nmol aa/$OD_{600nm}$) | *E. coli* BW25113 ΔilvC pSW3_lacI+ pACG_araBAD_ilvC |
|---|---|
| 0.4% L-ara | −5.5% |
| 0.8% L-ara | −25.2% |
| 1.6% L-ara | 8.5% |

| *E. coli* BW25113 pSW3_lacI+ 0.459 (nmol aa/$OD_{600nm}$) | *E. coli* BW25113 ΔilvC pSW3_lacI+ pACG_araBAD_ilvC |
|---|---|
| 0.4% L-ara | −5.5% |
| 0.8% L-ara | −25.2% |
| 1.6% L-ara | 8.5% |

| *E. coli* BW25113 pSW3_lacI+ 0.432 (nmol aa/$OD_{600nm}$) | *E. coli* BW25113 ΔilvIH pSW3_lacI+ pACG_araBAD_ilvIH | *E. coli* BW25113 ΔilvA pSW3_lacI+ pACG_araBAD_ilvA | *E. coli* BW25113 ΔilvBN pSW3_lacI+ pACG_araBAD_ilvBN | *E. coli* BW25113 pSW3_lacI+ pACG_araBAD_ilvGM |
|---|---|---|---|---|
| 0.05% L-ara | −26.4% | −10.3% | −42.0% | −21.3% |
| 0.2% L-ara | — | −14.1% | −23.2% | −12.8% |
| 0.8% L-ara | −12.8% | −2.2% | −14.0% | −18.5% |

For almost all tested strains and L-arabinose concentrations a slight reduction of β-methylnorleucine concentration is reported in the intracellular soluble protein fraction. However, this reduction is not really significant if compared with norvaline and norleucine, with exception of strain *E. coli* BW25113 ΔilvBN pSW3_lacI+ pACG_araBAD_ilvBN induced with 0.05% L-ara, where reduction reached about 42%. In addition, effect of increasing L-arabinose concentrations does not show a clear trend on variation of β-methylnorleucine concentration.

Example 9: Screening of Potential ilvGM- and ilvIH-Tunable *E. coli* Strains in a 15 L Reactor Under Conditions Triggering ncBCAA Formation During fermentation in large scale reactors, gradient zones of substrate, dissolved oxygen, pH and other parameters are formed due to inefficient mixing and *E. coli* cells respond to these environmental changes by modulating their metabolism (Schweder (1999). Monitoring of genes that respond to process-related stress in large-scale bioprocesses. Biotechnology and bioengineering, 65(2), 151-159). For instance, *E. coli* responds to glucose excess and oxygen limitation by shifting metabolism from oxidative respiration to mixed-acid fermentation, resulting in overflow metabolism (Enfors et al. (2001). Physiological responses to mixing in large scale bioreactors. Journal of biotechnology, 85(2), 175-185). Under these conditions, not only the mixed-acid fermentation products accumulate, but also pyruvate (Soini, J. et al. (2008). Norvaline is accumulated after a down-shift of oxygen in *Escherichia coli* W3110. Microb. Cell Fact., 7:1-14). Pyruvate excess present intracellularly increases the metabolic flux going to ncBCAA biosynthesis through the sequential keto acid chain elongation from pyruvate to α-ketocaproate over α-ketobutyrate and α-ketovalerate by the actuation of the leu operon-encoded enzymes (Apostol, I. et al. (1997). Incorporation of norvaline at leucine positions in recombinant human hemoglobin expressed in *Escherichia coli*. Journal of Biological Chemistry, 272(46), 28980-28988). This hypothesis is supported by the observations reported by Soini et al. (2011, Accumulation of amino acids deriving from pyruvate in *Escherichia coli* W3110 during fed-batch cultivation in a two-compartment scale-down bioreactor. Advances in Bioscience and Biotechnology, 2(05), 336): the combination of oxygen limitation with a constant glucose supply in a two-compartment STR-PFR scale-down bioreactor reported a significant impact on enhancing norvaline biosynthesis due to pyruvate accumulation in a recombinant *E. coli* cultivation. Furthermore, Soini et al. (2008) originally reported accumulation of pyruvate-based amino acids such the ncBCAAs norleucine and norvaline as well as alanine and valine in a standard STR fed-batch *E. coli* cultivation under glucose excess and induced oxygen limitation upon a stirrer downshift.

Concentration gradients happening in large industrial-scale bioreactors due to deficient mixing can be also simulated in small bioreactors in the laboratory. In this investigation scale-up effects are reproduced in a 15 L reactor by combining pyruvate pulsing and $O_2$ limitation. This novel cultivation strategy might represent more accurately the physiological behavior of bacterial cultivations taking place in large scale bioreactors.

According to the mini-bioreactor screening (Example 8), strains *E. coli* K-12 BW25113 pSW3_lacI+ pACG_araBAD_ilvGM (ilvGM-tunable *E. coli*) and *E. coli* K-12 BW25113 ΔlvIH pSW3_lacI+ pACG_araBAD_ilvIH (ilvIH-tunable *E. coli*) induced with 0.8% L-arabinose showed the best performance among all screened mutants in a 10 mL mini-bioreactor, since they reported the most significant reduction of ncBCAA mis-incorporation into recombinant mini-proinsulin in comparison with the control non-engineered *E. coli* strain. The aim of this experiment was to verify the performance of the aforementioned potential tunable *E. coli* strains in a 15 L reactor under cultivation conditions triggering formation of ncBCAA, i.e. pyruvate pulses and oxygen limitation, in order to confirm its advantage as strain ensuring product quality. For comparison, the control non-engineered *E. coli* host (*E. coli* K-12 BW25113 pSW3_lacI+) was also cultivated.

Cultivation of *E. coli* K-12 BW25113 pSW3_lacI+ (Control Strain) Under Standard Conditions 100 μL of a cryostock containing *E. coli* K-12 BW25113 pSW3_lacI+ were used to inoculate 500 mL of supplemented mineral salt medium containing 5 g/L glucose and 100 μg/mL ampicillin in order to generate the pre-culture. Composition of the mineral salt medium was as follows: 2 g/L $Na_2SO_4$, 2.468 g/L $(NH_4)_2SO_4$, 0.5 g/L $NH_4Cl$, 14.6 g/L $K_2HPO_4$, 3.6 g/L NaH2PO4·$2H_2O$ and 1 g/L $(NH_4)_2$—H-citrate. The mineral salt medium was then supplemented with 2 mL/L $MgSO_4$ solution (1.0 M) and 2 mL/L trace elements solution. The trace element solution comprised (per L): 0.5 g $CaCl_2$)×$2H_2O$, 0.18 g $ZnSO_4$×$7H_2O$, 0.1 g $MnSO_4 \times H_2O$, 16.7 g $FeCl_3 \times 6H_2O$, 0.16 g $CuSO_4 \times 5H_2O$, 0.18 g $CoCl_2 \times 6H_2O$. The pre-culture was incubated at 37° C. and 220 rpm in an orbital shaker for 12 h, using an initial cold-start technique. $OD_{600\ nm}$ at the end of the pre-culture was measured and a given volume was used to inoculate a 7 L starting volume reactor so that initial $OD_{600\ nm}$ was 0.4. The reactor medium consisted of supplemented mineral salt medium containing 5 g/L glucose, 2 mL antifoam (Antifoam 2014, Sigma) and 100 µg/mL ampicillin. Cultivation was carried out at 37° C. and the pH was maintained at 7 by automatic control with 25% $NH_4OH$. Airflow was set to 7 vvm and DO set-point to 20%, maintaining the last by using a cascade control altering stirrer speed (initial stirrer speed was set to 800 rpm). Batch phase lasted effectively 4 h, with an intermediate 13 h cold phase at 15° C. At the end of the batch phase, exponential feeding was started, according to following equation:

$$F(t) = \frac{q_s}{S} \cdot (X \cdot V) \cdot e^{\mu_{set} \cdot t}$$

where F (t) represents the feed flow rate over time ($L\ h^{-1}$), $q_s$ the set-point of the specific substrate uptake rate ($0.514\ gS\ gX^{-1}\ h^{-1}$), S the concentration of glucose in the feed solution (442 g/L), X the biomass concentration over time (g/L), V the volume of the reactor over time (L), $\mu_{set}$ the set-point of the specific cell growth rate ($0.3\ h^{-1}$) and t the time during the fed-batch phase. The feed solution consisted of TUB mineral salt medium supplemented with 4 mL/L trace elements solution, 2 mL/L $MgSO_4$ solution (1.0 M), 100 µg/mL ampicillin and 442 g/L glucose.

Exponential fed-batch phase was carried out for 3 hours and afterwards expression of recombinant mini-proinsulin was induced by automatic addition of IPTG to a final concentration of 0.5 mM. Induction time was 30 minutes. During the induction phase no feed was added into the reactor. After induction, a constant feeding phase was started, so that the constant flow rate was equal to the last flow rate achieved in the exponential feeding phase. Constant feed fed-batch phase was active for 5-6 h.

Cultivation of *E. coli* K-12 BW25113 pSW3_lacI$^+$ (Control Strain) Under Conditions Triggering ncBCAA Formation Cultivation was performed as described for the standard cultivation in previous section. However, after the exponential fed-batch phase, 1 g/L pyruvate pulse was automatically added into the reactor. Pyruvate solution was constantly pumped for 5 minutes. During that time period no feed was added, airflow rate was temporary set to 0 and DO cascade control was disconnected. After the first pyruvate pulse, expression of recombinant mini-proinsulin was induced by automatic addition of IPTG to a final concentration of 0.5 mM. Induction time was 30 minutes. During the induction phase no feed was added into the reactor and airflow and DO cascade control were re-established. After induction, sequential 1 g/L pyruvate pulses were performed each 30 min as described above for a total of 4 pulses. Between pulses, constant feeding phase was activated, so that the constant flow rate was equal to the last flow rate achieved in the exponential feeding phase, and airflow and DO cascade control were re-established. Constant feed fed-batch phase was active for 5-6 h.

Cultivation of ilvGM-Tunable *E. coli* Under Conditions Triggering ncBCAA Formation Cultivation operation was as described in previous section and only minor changes were done in order to adapt the cultivation process to ilvGM-tunable *E. coli* strain. Both pre-culture and reactor medium contained additionally 25 µg/mL chloramphenicol. The reactor medium additionally contained 0.8% L-arabinose, necessary to induce expression of gene ilvGM hosted in plasmid pACG_araBAD_ilvGM. The feeding solution was also additionally supplemented with 25 µg/mL chloramphenicol and 0.8% L-arabinose.

Cultivation of ilvIH-Tunable *E. coli* Under Conditions Triggering ncBCAA Formation Cultivation operation was as described in previous section.

Example 10: Analysis of ncBCAA

Concentrations of ncBCAA present in the intracellular soluble protein fraction and in the inclusion body fraction over cultivation time for each tested strain in Example 9 are shown in FIG. 11 and FIG. 12, respectively.

The cultivation of the control *E. coli* strain subjected to pyruvate pulses combined with $O_2$ limitation ("WT *E. coli*, PYR-O2") reported a progressive accumulation of norleucine and β-methylnorleucine in the intracellular soluble protein fraction over time after induction, being that more significant for norleucine. Furthermore, norvaline concentration also increased progressively under aforementioned cultivation conditions, but only until 3 h after induction. From that time point on, norvaline concentration progressively dropped until reaching initial values at 5 h after induction. This might suggest that, after 2 h from last pyruvate pulse combined with $O_2$ limitation, its associated effect triggering norvaline accumulation is not active anymore (FIG. 11). As expected, the aforementioned strain reported a higher level of norvaline and norleucine than the control *E. coli* strain cultivated under standard conditions ("WT *E. coli*, STD"). Such concentration difference could not be observed for β-methylnorleucine.

Both tested potential mutants in cultivations "ilvGM-tunable *E. coli*, PYR-O2" and "ilvIH-tunable *E. coli*, PYR-O2" reported a dramatic reduction of norvaline and norleucine concentrations in the intracellular soluble protein fraction, being such decrease higher for norleucine in "ilvGM-tunable *E. coli*, PYR-O2". However, β-methylnorleucine concentrations did not significantly vary with respect to the control cultivation. It is noteworthy to highlight that, for most samples, norvaline could not be properly detected since concentrations were under the limit of detection of the GC-FID equipment (FIG. 11).

The cultivation of the control *E. coli* strain subjected to pyruvate pulses combined with $O_2$ limitation ("WT *E. coli*, PYR-O2") reported a progressive accumulation of norvaline and norleucine in the inclusion body fraction over time after induction. As expected, the aforementioned strain reported a higher level of norvaline and norleucine than the control *E. coli* strain cultivated under standard conditions ("WT *E. coli*, STD"). Again, and similar to reported in the intracellular soluble fraction, both tested potential mutants in cultivations "ilvGM-tunable *E. coli*, PYR-O2" and "ilvIH-tunable *E. coli*, PYR-O2" reported a dramatic reduction of norvaline and norleucine concentrations in the inclusion body fraction, being this decrease even higher for norleucine in "ilvGM-tunable *E. coli*, PYR-O2". Norvaline could not be detected in any case for both tested mutants. β-methylnorleucine could not be detected in any tested samples (FIG. 12).

The invention claimed is:

1. A method for producing a recombinant polypeptide of interest in a microbial host cell, the method comprising:

(a) selecting a microbial host cell with genomic DNA having a knock-out of a gene encoding an enzyme selected from the group consisting of acetohydroxyacid synthase (AHAS) isoform III, ketol-acid reductoisomerase (NADP(+)), aspartate kinase, and homoserine dehydrogenase, (b) modifying said microbial host cell by introducing a first plasmid expressing a polynucleotide encoding said enzyme such that enzymatic activity of said enzyme is increased in said microbial host cell as compared to enzymatic activity of said enzyme in the microbial host cell with genomic DNA having a knock-out of a gene encoding said enzyme, (c) introducing a second plasmid comprising a polynucleotide encoding the recombinant polypeptide of interest into said microbial host cell of (b), (d) expressing said recombinant polypeptide of interest in said microbial host cell, and wherein the recombinant polypeptide of interest expressed by said microbial host cell has lower misincorporation of non-canonical branched-chain amino acids selected from norvaline and norleucine as compared to a same recombinant polypeptide of interest expressed by an otherwise identical microbial host cell that has not been modified with said first plasmid.

2. The method of claim 1, wherein the method further comprises isolation of the recombinant polypeptide of interest from the microbial host cell, and purification of the recombinant polypeptide.

3. The method of claim 2, wherein the purification comprises enrichment of recombinant polypeptides of interest which do not comprise non-canonical branched-chain amino acids.

4. The method of claim 1, wherein the polynucleotide encoding the recombinant polypeptide of interest and/or the polynucleotide encoding the enzyme is operably linked to an inducible promoter.

5. The method of claim 1, wherein said microbial host cell is an *Escherichia coli* cell.

6. The method of claim 1, wherein the recombinant polypeptide of interest is an insulin or a proinsulin.

7. The method of claim 6, wherein the insulin is insulin lispro, insulin aspart, insulin glulisine, insulin detemir, insulin glargine, or a precursor thereof.

* * * * *

SEQUENCE LISTING

<160> NUMBER OF SEQ ID NOS: 46

<210> SEQ ID NO 1
<211> LENGTH: 1572
<212> TYPE: DNA
<213> ORGANISM: Escherichia coli
<220> FEATURE:
<223> OTHER INFORMATION: leuA, 2-isopropylmalate synthase

<400> SEQUENCE: 1

```
atgagccagc aagtcattat tttcgatacc acattgcgcg acggtgaaca ggcgttacag     60
gcaagcttga gtgtgaaaga aaaactgcaa attgcgctgg cccttgagcg tatgggtgtt    120
gacgtgatgg aagtcggttt ccccgtctct tcgccgggcg attttgaatc ggtgcaaacc    180
atcgcccgcc aggttaaaaa cagccgcgta tgtgcgttag ctcgctgcgt ggaaaaagat    240
atcgacgtgg cggccgaatc cctgaaagtc gccgaagcct tccgtattca tacctttatt    300
gccacttcgc caatgcacat cgccaccaag ctgcgcagca cgctggacga ggtgatcgaa    360
cgcgctatct atatggtgaa acgcgcccgt aattacaccg atgatgttga attttcttgc    420
gaagatgccg ggcgtacacc cattgccgat ctggcgcgag tggtcgaagc ggcgattaat    480
gccggtgcca ccaccatcaa cattccggac accgtgggct acaccatgcc gtttgagttc    540
gccggaatca tcagcggcct gtatgaacgc gtgcctaaca tcgacaaagc cattatctcc    600
gtacataccc acgacgattt gggcctggcg gtcggaaact cactggcggc ggtacatgcc    660
ggtgcacgcc aggtggaagg cgcaatgaac gggatcggcg agcgtgccgg aaactgttcc    720
ctggaagaag tcatcatggc gatcaaagtt cgtaaggata ttctcaacgt ccacaccgcc    780
attaatcacc aggagatatg gcgcaccagc cagttagtta gccagatttg taatatgccg    840
atcccggcaa acaaagccat tgttggcagc ggcgcattcg cacactcctc cggtatacac    900
caggatggcg tgctgaaaaa ccgcgaaaac tacgaaatca tgacaccaga atctattggt    960
ctgaaccaaa tccagctgaa tctgacctct cgttcggggc gtgcggcggt gaaacatcgc   1020
atggatgaga tggggtataa agaaagtgaa tataatttag acaatttgta cgatgctttc   1080
ctgaagctgg cggacaaaaa aggtcaggtg tttgattacg atctggaggc gctggccttc   1140
atcggtaagc agcaagaaga gccggagcat ttccgtctgg attacttcag cgtgcagtct   1200
ggctctaacg atatcgccac cgccgccgtc aaactggcct gtggcgaaga agtcaaagca   1260
gaagccgcca acggtaacgg tccggtcgat gccgtctatc aggcaattaa ccgcatcact   1320
gaatataacg tcgaactggt gaaatacagc ctgaccgcca aaggccacgg taaagatgcg   1380
ctgggtcagg tggatatcgt cgctaactac aacggtcgcc gcttccacgg cgtcggcctg   1440
gctaccgata ttgtcgagtc atctgccaaa gccatggtgc acgttctgaa caatatctgg   1500
cgtgccgcag aagtcgaaaa agagttgcaa cgcaaagctc aacacaacga aaacaacaag   1560
gaaaccgtgt ga                                                      1572
```

<210> SEQ ID NO 2
<211> LENGTH: 523
<212> TYPE: PRT
<213> ORGANISM: Escherichia coli
<220> FEATURE:
<223> OTHER INFORMATION: leuA, 2-isopropylmalate synthase

<400> SEQUENCE: 2

```
Met Ser Gln Gln Val Ile Ile Phe Asp Thr Thr Leu Arg Asp Gly Glu
1               5                   10                  15
```

```
Gln Ala Leu Gln Ala Ser Leu Ser Val Lys Glu Lys Leu Gln Ile Ala
            20                  25                  30

Leu Ala Leu Glu Arg Met Gly Val Asp Val Met Glu Val Gly Phe Pro
        35                  40                  45

Val Ser Ser Pro Gly Asp Phe Glu Ser Val Gln Thr Ile Ala Arg Gln
    50                  55                  60

Val Lys Asn Ser Arg Val Cys Ala Leu Ala Arg Cys Val Glu Lys Asp
65                  70                  75                  80

Ile Asp Val Ala Ala Glu Ser Leu Lys Val Ala Glu Ala Phe Arg Ile
                85                  90                  95

His Thr Phe Ile Ala Thr Ser Pro Met His Ile Ala Thr Lys Leu Arg
            100                 105                 110

Ser Thr Leu Asp Glu Val Ile Glu Arg Ala Ile Tyr Met Val Lys Arg
        115                 120                 125

Ala Arg Asn Tyr Thr Asp Asp Val Glu Phe Ser Cys Glu Asp Ala Gly
    130                 135                 140

Arg Thr Pro Ile Ala Asp Leu Ala Arg Val Val Glu Ala Ala Ile Asn
145                 150                 155                 160

Ala Gly Ala Thr Thr Ile Asn Ile Pro Asp Thr Val Gly Tyr Thr Met
                165                 170                 175

Pro Phe Glu Phe Ala Gly Ile Ile Ser Gly Leu Tyr Glu Arg Val Pro
            180                 185                 190

Asn Ile Asp Lys Ala Ile Ile Ser Val His Thr His Asp Asp Leu Gly
        195                 200                 205

Leu Ala Val Gly Asn Ser Leu Ala Ala Val His Ala Gly Ala Arg Gln
    210                 215                 220

Val Glu Gly Ala Met Asn Gly Ile Gly Glu Arg Ala Gly Asn Cys Ser
225                 230                 235                 240

Leu Glu Glu Val Ile Met Ala Ile Lys Val Arg Lys Asp Ile Leu Asn
                245                 250                 255

Val His Thr Ala Ile Asn His Gln Glu Ile Trp Arg Thr Ser Gln Leu
            260                 265                 270

Val Ser Gln Ile Cys Asn Met Pro Ile Pro Ala Asn Lys Ala Ile Val
        275                 280                 285

Gly Ser Gly Ala Phe Ala His Ser Ser Gly Ile His Gln Asp Gly Val
    290                 295                 300

Leu Lys Asn Arg Glu Asn Tyr Glu Ile Met Thr Pro Glu Ser Ile Gly
305                 310                 315                 320

Leu Asn Gln Ile Gln Leu Asn Leu Thr Ser Arg Ser Gly Arg Ala Ala
                325                 330                 335

Val Lys His Arg Met Asp Glu Met Gly Tyr Lys Glu Ser Glu Tyr Asn
            340                 345                 350

Leu Asp Asn Leu Tyr Asp Ala Phe Leu Lys Leu Ala Asp Lys Lys Gly
        355                 360                 365

Gln Val Phe Asp Tyr Asp Leu Glu Ala Leu Ala Phe Ile Gly Lys Gln
    370                 375                 380

Gln Glu Glu Pro Glu His Phe Arg Leu Asp Tyr Phe Ser Val Gln Ser
385                 390                 395                 400

Gly Ser Asn Asp Ile Ala Thr Ala Ala Val Lys Leu Ala Cys Gly Glu
                405                 410                 415

Glu Val Lys Ala Glu Ala Ala Asn Gly Asn Gly Pro Val Asp Ala Val
            420                 425                 430

Tyr Gln Ala Ile Asn Arg Ile Thr Glu Tyr Asn Val Glu Leu Val Lys
```

-continued

```
        435                 440                 445

Tyr Ser Leu Thr Ala Lys Gly His Gly Lys Asp Ala Leu Gly Gln Val
    450                 455                 460

Asp Ile Val Ala Asn Tyr Asn Gly Arg Arg Phe His Gly Val Gly Leu
465                 470                 475                 480

Ala Thr Asp Ile Val Glu Ser Ser Ala Lys Ala Met Val His Val Leu
                485                 490                 495

Asn Asn Ile Trp Arg Ala Ala Glu Val Glu Lys Glu Leu Gln Arg Lys
            500                 505                 510

Ala Gln His Asn Glu Asn Asn Lys Glu Thr Val
        515                 520


<210> SEQ ID NO 3
<211> LENGTH: 1476
<212> TYPE: DNA
<213> ORGANISM: Escherichia coli
<220> FEATURE:
<223> OTHER INFORMATION: ilvC, ketol-acid reductoisomerase

<400> SEQUENCE: 3

atggctaact acttcaatac actgaatctg cgccagcagc tggcacagct gggcaaatgt      60

cgctttatgg gccgcgatga attcgccgat ggcgcgagct accttcaggg taaaaaagta     120

gtcatcgtcg gctgtggcgc acagggtctg aaccagggcc tgaacatgcg tgattctggt     180

ctcgatatct cctacgctct gcgtaaagaa gcgattgccg agaagcgcgc gtcctggcgt     240

aaagcgaccg aaaatggttt taaagtgggt acttacgaag aactgatccc acaggcggat     300

ctggtgatta acctgacgcc ggacaagcag cactctgatg tagtgcgcac cgtacagcca     360

ctgatgaaag acggcgcggc gctgggctac tcgcacggtt tcaacatcgt cgaagtgggc     420

gagcagatcc gtaaagatat caccgtagtg atggttgcgc cgaaatgccc aggcaccgaa     480

gtgcgtgaag agtacaaacg tgggttcggc gtaccgacgc tgattgccgt tcacccggaa     540

aacgatccga aaggcgaagg catggcgatt gccaaagcct gggcggctgc aaccggtggt     600

caccgtgcgg gtgtgctgga atcgtccttc gttgcggaag tgaaatctga cctgatgggc     660

gagcaaacca tcctgtgcgg tatgttgcag gctggctctc tgctgtgctt cgacaagctg     720

gtggaagaag gtaccgatcc agcatacgca gaaaaactga ttcagttcgg ttgggaaacc     780

atcaccgaag cactgaaaca gggcggcatc accctgatga tggaccgtct ctctaacccg     840

gcgaaactgc gtgcttatgc gctttctgaa cagctgaaag agatcatggc acccctgttc     900

cagaaacata tggacgacat catctccggc gaattctctt ccggtatgat ggcggactgg     960

gccaacgatg ataagaaact gctgacctgg cgtgaagaga ccggcaaaac cgcgtttgaa    1020

accgcgccgc agtatgaagg caaaatcggc gagcaggagt acttcgataa aggcgtactg    1080

atgattgcga tggtgaaagc gggcgttgaa ctggcgttcg aaaccatggt cgattccggc    1140

atcattgaag agtctgcata ttatgaatca ctgcacgagc tgccgctgat tgccaacacc    1200

atcgcccgta agcgtctgta cgaaatgaac gtggttatct ctgataccgc tgagtacggt    1260

aactatctgt tctcttacgc ttgtgtgccg ttgctgaaac cgtttatggc agagctgcaa    1320

ccgggcgacc tgggtaaagc tattccggaa ggcgcggtag ataacgggca actgcgtgat    1380

gtgaacgaag cgattcgcag ccatgcgatt gagcaggtag gtaagaaact gcgcggctat    1440

atgacagata tgaaacgtat tgctgttgcg ggttaa                              1476


<210> SEQ ID NO 4
```

<211> LENGTH: 491
<212> TYPE: PRT
<213> ORGANISM: Escherichia coli
<220> FEATURE:
<223> OTHER INFORMATION: ilvC, ketol-acid reductoisomerase

<400> SEQUENCE: 4

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

```
Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490
```

<210> SEQ ID NO 5
<211> LENGTH: 1644
<212> TYPE: DNA
<213> ORGANISM: Escherichia coli
<220> FEATURE:
<223> OTHER INFORMATION: Native gene ilvG, AHAS isoform II

<400> SEQUENCE: 5

```
atgaatggcg cacagtgggt ggtacatgcg ttgcgggcac agggtgtgaa caccgttttc     60

ggttatccgg gtggcgcaat tatgccggtt tacgatgcat tgtatgacgg cggcgtggag    120

cacttgctat gccgacatga gcagggtgcg gcaatggcgg ctatcggtta tgctcgtgct    180

accggcaaaa ctggcgtatg tatcgccacg tctggtccgg gcgcaaccaa cctgataacc    240

gggcttgcgg acgcactgtt agattccatc cctgttgttg ccatcaccgg tcaagtgtcc    300

gcaccgttta tcggcactga cgcatttcag gaagtggatg tcctgggatt gtcgttagcc    360

tgtaccaagc acagctttct ggtgcagtcg ctggaagagt tgccgcgcat catggctgaa    420

gcattcgacg ttgcctgctc aggtcgtcct ggtccggttc tggtcgatat cccaaaagat    480

atccagttag ccagcggtga cctggaaccg tggttcacca ccgttgaaaa cgaagtgact    540

ttcccacatg ccgaagttga gcaagcgcgc cagatgctgg caaaagcgca aaaaccgatg    600

ctgtacgttg gcggtggcgt gggtatggcg caggcagttc cggctttgcg tgaatttctc    660

gctgccacaa aaatgcctgc cacctgtacg ctgaaagggc tgggcgcagt agaagcagat    720

tatccgtact atctgggcat gctggggatg cacggcacca aagcggcaaa cttcgcggtg    780

caggagtgtg acctgctgat cgccgtgggc gcacgttttg atgaccgggt gaccggcaaa    840

ctgaacacct tcgcgccaca cgccagtgtt atccatatgg atatcgaccc ggcagaaatg    900

aacaagctgc gtcaggcaca tgtggcatta caaggtgatt taaatgctct gttaccagca    960

ttacagcagc cgttaaatca atactggcag caacactgcg cgcagctgcg tgatgaacat   1020

tcctggcgtt acgaccatcc cggtgacgct atctacgcgc cgttgttgtt aaaacaactg   1080

tcggatcgta aacctgcgga ttgcgtcgtg accacagatg tggggcagca ccagatgtgg   1140

gctgcgcagc acatcgccca cactcgcccg gaaaatttca tcacctccag cggtttaggt   1200

accatgggtt ttggtttacc ggcggcggtt ggcgcacaag tcgcgcgacc gaacgatacc   1260

gttgtctgta tctccggtga cggctctttc atgatgaatg tgcaagagct gggcaccgta   1320

aaacgcaagc agttaccgtt gaaaatcgtc ttactcgata accaacggtt agggatggtt   1380

cgacaatggc agcaactgtt ttttcaggaa cgatacagcg aaaccaccct tactgataac   1440
```

-continued

```
cccgatttcc tcatgttagc cagcgccttc ggcatccatg gccaacacat cacccggaaa   1500

gaccaggttg aagcggcact cgacaccatg ctgaacagtg atgggccata cctgcttcat   1560

gtctcaatcg acgaacttga gaacgtctgg ccgctggtgc cgcctggcgc cagtaattca   1620

gaaatgttgg agaaattatc atga                                          1644


<210> SEQ ID NO 6
<211> LENGTH: 547
<212> TYPE: PRT
<213> ORGANISM: Escherichia coli
<220> FEATURE:
<223> OTHER INFORMATION: Native protein product ilvG, AHAS isoform II

<400> SEQUENCE: 6

Met Asn Gly Ala Gln Trp Val Val His Ala Leu Arg Ala Gln Gly Val
1               5                   10                  15

Asn Thr Val Phe Gly Tyr Pro Gly Gly Ala Ile Met Pro Val Tyr Asp
            20                  25                  30

Ala Leu Tyr Asp Gly Gly Val Glu His Leu Leu Cys Arg His Glu Gln
        35                  40                  45

Gly Ala Ala Met Ala Ala Ile Gly Tyr Ala Arg Ala Thr Gly Lys Thr
    50                  55                  60

Gly Val Cys Ile Ala Thr Ser Gly Pro Gly Ala Thr Asn Leu Ile Thr
65                  70                  75                  80

Gly Leu Ala Asp Ala Leu Leu Asp Ser Ile Pro Val Val Ala Ile Thr
                85                  90                  95

Gly Gln Val Ser Ala Pro Phe Ile Gly Thr Asp Ala Phe Gln Glu Val
            100                 105                 110

Asp Val Leu Gly Leu Ser Leu Ala Cys Thr Lys His Ser Phe Leu Val
        115                 120                 125

Gln Ser Leu Glu Glu Leu Pro Arg Ile Met Ala Glu Ala Phe Asp Val
    130                 135                 140

Ala Cys Ser Gly Arg Pro Gly Pro Val Leu Val Asp Ile Pro Lys Asp
145                 150                 155                 160

Ile Gln Leu Ala Ser Gly Asp Leu Glu Pro Trp Phe Thr Thr Val Glu
                165                 170                 175

Asn Glu Val Thr Phe Pro His Ala Glu Val Glu Gln Ala Arg Gln Met
            180                 185                 190

Leu Ala Lys Ala Gln Lys Pro Met Leu Tyr Val Gly Gly Gly Val Gly
        195                 200                 205

Met Ala Gln Ala Val Pro Ala Leu Arg Glu Phe Leu Ala Ala Thr Lys
    210                 215                 220

Met Pro Ala Thr Cys Thr Leu Lys Gly Leu Gly Ala Val Glu Ala Asp
225                 230                 235                 240

Tyr Pro Tyr Tyr Leu Gly Met Leu Gly Met His Gly Thr Lys Ala Ala
                245                 250                 255

Asn Phe Ala Val Gln Glu Cys Asp Leu Leu Ile Ala Val Gly Ala Arg
            260                 265                 270

Phe Asp Asp Arg Val Thr Gly Lys Leu Asn Thr Phe Ala Pro His Ala
        275                 280                 285

Ser Val Ile His Met Asp Ile Asp Pro Ala Glu Met Asn Lys Leu Arg
    290                 295                 300

Gln Ala His Val Ala Leu Gln Gly Asp Leu Asn Ala Leu Leu Pro Ala
305                 310                 315                 320
```

```
Leu Gln Gln Pro Leu Asn Gln Tyr Trp Gln Gln His Cys Ala Gln Leu
            325                 330                 335

Arg Asp Glu His Ser Trp Arg Tyr Asp His Pro Gly Asp Ala Ile Tyr
            340                 345                 350

Ala Pro Leu Leu Leu Lys Gln Leu Ser Asp Arg Lys Pro Ala Asp Cys
        355                 360                 365

Val Val Thr Thr Asp Val Gly Gln His Gln Met Trp Ala Ala Gln His
    370                 375                 380

Ile Ala His Thr Arg Pro Glu Asn Phe Ile Thr Ser Ser Gly Leu Gly
385                 390                 395                 400

Thr Met Gly Phe Gly Leu Pro Ala Ala Val Gly Ala Gln Val Ala Arg
            405                 410                 415

Pro Asn Asp Thr Val Val Cys Ile Ser Gly Asp Gly Ser Phe Met Met
            420                 425                 430

Asn Val Gln Glu Leu Gly Thr Val Lys Arg Lys Gln Leu Pro Leu Lys
        435                 440                 445

Ile Val Leu Leu Asp Asn Gln Arg Leu Gly Met Val Arg Gln Trp Gln
    450                 455                 460

Gln Leu Phe Phe Gln Glu Arg Tyr Ser Glu Thr Thr Leu Thr Asp Asn
465                 470                 475                 480

Pro Asp Phe Leu Met Leu Ala Ser Ala Phe Gly Ile His Gly Gln His
            485                 490                 495

Ile Thr Arg Lys Asp Gln Val Glu Ala Ala Leu Asp Thr Met Leu Asn
            500                 505                 510

Ser Asp Gly Pro Tyr Leu Leu His Val Ser Ile Asp Glu Leu Glu Asn
        515                 520                 525

Val Trp Pro Leu Val Pro Pro Gly Ala Ser Asn Ser Glu Met Leu Glu
    530                 535                 540

Lys Leu Ser
545


<210> SEQ ID NO 7
<211> LENGTH: 264
<212> TYPE: DNA
<213> ORGANISM: Escherichia coli
<220> FEATURE:
<223> OTHER INFORMATION: Native gene ilvM

<400> SEQUENCE: 7

atgatgcaac atcaggtcaa tgtatcggct cgcttcaatc cagaaacctt agaacgtgtt      60

ttacgcgtgg tgcgtcatcg tggtttccac gtctgctcaa tgaatatggc cgccgccagc     120

gatgcacaaa atataaatat cgaattgacc gttgccagcc cacggtcggt cgacttactg     180

tttagtcagt taaataaact ggtggacgtc gcacacgttg ccatctgcca gagcacaacc     240

acatcacaac aaatccgcgc ctga                                            264


<210> SEQ ID NO 8
<211> LENGTH: 87
<212> TYPE: PRT
<213> ORGANISM: Escherichia coli
<220> FEATURE:
<223> OTHER INFORMATION: Native protein product ilvM

<400> SEQUENCE: 8

Met Met Gln His Gln Val Asn Val Ser Ala Arg Phe Asn Pro Glu Thr
1               5                   10                  15

Leu Glu Arg Val Leu Arg Val Val Arg His Arg Gly Phe His Val Cys
```

```
            20                  25                  30

Ser Met Asn Met Ala Ala Ala Ser Asp Ala Gln Asn Ile Asn Ile Glu
        35                  40                  45

Leu Thr Val Ala Ser Pro Arg Ser Val Asp Leu Leu Phe Ser Gln Leu
    50                  55                  60

Asn Lys Leu Val Asp Val Ala His Val Ala Ile Cys Gln Ser Thr Thr
65                  70                  75                  80

Thr Ser Gln Gln Ile Arg Ala
                85
```

<210> SEQ ID NO 9
<211> LENGTH: 933
<212> TYPE: DNA
<213> ORGANISM: Escherichia coli
<220> FEATURE:
<223> OTHER INFORMATION: thrB, homoserine kinase

<400> SEQUENCE: 9

```
atggttaaag tttatgcccc ggcttccagt gccaatatga gcgtcgggtt tgatgtgctc     60

ggggcggcgg tgacacctgt tgatggtgca ttgctcggag atgtagtcac ggttgaggcg    120

gcagagacat tcagtctcaa caacctcgga cgctttgccg ataagctgcc gtcagaacca    180

cgggaaaata tcgtttatca gtgctgggag cgtttttgcc aggaactggg taagcaaatt    240

ccagtggcga tgaccctgga aaagaatatg ccgatcggtt cgggcttagg ctccagtgcc    300

tgttcggtgg tcgcggcgct gatggcgatg aatgaacact gcggcaagcc gcttaatgac    360

actcgtttgc tggctttgat gggcgagctg gaaggccgta tctccggcag cattcattac    420

gacaacgtgg caccgtgttt tctcggtggt atgcagttga tgatcgaaga aaacgacatc    480

atcagccagc aagtgccagg gtttgatgag tggctgtggg tgctggcgta tccggggatt    540

aaagtctcga cggcagaagc cagggctatt ttaccggcgc agtatcgccg ccaggattgc    600

attgcgcacg ggcgacatct ggcaggcttc attcacgcct gctattcccg tcagcctgag    660

cttgccgcga agctgatgaa agatgttatc gctgaaccct accgtgaacg gttactgcca    720

ggcttccggc aggcgcggca ggcggtcgcg gaaatcggcg cggtagcgag cggtatctcc    780

ggctccggcc cgaccttgtt cgctctgtgt gacaagccgg aaaccgccca gcgcgttgcc    840

gactggttgg gtaagaacta cctgcaaaat caggaaggtt ttgttcatat ttgccggctg    900

gatacggcgg gcgcacgagt actggaaaac taa                                933
```

<210> SEQ ID NO 10
<211> LENGTH: 310
<212> TYPE: PRT
<213> ORGANISM: Escherichia coli
<220> FEATURE:
<223> OTHER INFORMATION: thrB, homoserine kinase

<400> SEQUENCE: 10

```
Met Val Lys Val Tyr Ala Pro Ala Ser Ser Ala Asn Met Ser Val Gly
1               5                   10                  15

Phe Asp Val Leu Gly Ala Ala Val Thr Pro Val Asp Gly Ala Leu Leu
            20                  25                  30

Gly Asp Val Val Thr Val Glu Ala Ala Glu Thr Phe Ser Leu Asn Asn
        35                  40                  45

Leu Gly Arg Phe Ala Asp Lys Leu Pro Ser Glu Pro Arg Glu Asn Ile
    50                  55                  60

Val Tyr Gln Cys Trp Glu Arg Phe Cys Gln Glu Leu Gly Lys Gln Ile
```

```
65                  70                  75                  80

Pro Val Ala Met Thr Leu Glu Lys Asn Met Pro Ile Gly Ser Gly Leu
                85                  90                  95

Gly Ser Ser Ala Cys Ser Val Val Ala Ala Leu Met Ala Met Asn Glu
            100                 105                 110

His Cys Gly Lys Pro Leu Asn Asp Thr Arg Leu Leu Ala Leu Met Gly
        115                 120                 125

Glu Leu Glu Gly Arg Ile Ser Gly Ser Ile His Tyr Asp Asn Val Ala
    130                 135                 140

Pro Cys Phe Leu Gly Gly Met Gln Leu Met Ile Glu Glu Asn Asp Ile
145                 150                 155                 160

Ile Ser Gln Gln Val Pro Gly Phe Asp Glu Trp Leu Trp Val Leu Ala
                165                 170                 175

Tyr Pro Gly Ile Lys Val Ser Thr Ala Glu Ala Arg Ala Ile Leu Pro
            180                 185                 190

Ala Gln Tyr Arg Arg Gln Asp Cys Ile Ala His Gly Arg His Leu Ala
        195                 200                 205

Gly Phe Ile His Ala Cys Tyr Ser Arg Gln Pro Glu Leu Ala Ala Lys
    210                 215                 220

Leu Met Lys Asp Val Ile Ala Glu Pro Tyr Arg Glu Arg Leu Leu Pro
225                 230                 235                 240

Gly Phe Arg Gln Ala Arg Gln Ala Val Ala Glu Ile Gly Ala Val Ala
                245                 250                 255

Ser Gly Ile Ser Gly Ser Gly Pro Thr Leu Phe Ala Leu Cys Asp Lys
            260                 265                 270

Pro Glu Thr Ala Gln Arg Val Ala Asp Trp Leu Gly Lys Asn Tyr Leu
        275                 280                 285

Gln Asn Gln Glu Gly Phe Val His Ile Cys Arg Leu Asp Thr Ala Gly
    290                 295                 300

Ala Arg Val Leu Glu Asn
305                 310
```

<210> SEQ ID NO 11
<211> LENGTH: 1545
<212> TYPE: DNA
<213> ORGANISM: Escherichia coli
<220> FEATURE:
<223> OTHER INFORMATION: Native gene ilvA, L-threonine dehydratase

<400> SEQUENCE: 11

```
atggctgact cgcaacccct gtccggtgct ccggaaggtg ccgaatattt aagagcagtg     60

ctgcgcgcgc cggtttacga ggcggcgcag gttacgccgc tacaaaaaat ggaaaaactg    120

tcgtcgcgtc ttgataacgt cattctggtg aagcgcgaag atcgccagcc agtgcacagc    180

tttaagctgc gcggcgcata cgccatgatg gcgggcctga cggaagaaca gaaagcgcac    240

ggcgtgatca ctgcttctgc gggtaaccac gcgcagggcg tcgcgttttc ttctgcgcgg    300

ttaggcgtga aggccctgat cgttatgcca accgccaccg ccgacatcaa agtcgacgcg    360

gtgcgcggct tcggcggcga agtgctgctc cacggcgcga actttgatga agcgaaagcc    420

aaagcgatcg aactgtcaca gcagcagggg ttcacctggg tgccgccgtt cgaccatccg    480

atggtgattg ccgggcaagg cacgctggcg ctggaactgc tccagcagga cgcccatctc    540

gaccgcgtat ttgtgccagt cggcggcggc ggtctggctg ctggcgtggc ggtgctgatc    600

aaacaactga tgccgcaaat caaagtgatc gccgtagaag cggaagactc cgcctgcctg    660
```

```
aaagcagcgc tggatgcggg tcatccggtt gatctgccgc gcgtagggct atttgctgaa    720

ggcgtagcgg taaaacgcat cggtgacgaa accttccgtt tatgccagga gtatctcgac    780

gacatcatca ccgtcgatag cgatgcgatc tgtgcggcga tgaaggattt attcgaagat    840

gtgcgcgcgg tggcggaacc ctctggcgcg ctggcgctgg cgggaatgaa aaaatatatc    900

gccctgcaca acattcgcgg cgaacggctg gcgcatattc tttccggtgc caacgtgaac    960

ttccacggcc tgcgctacgt ctcagaacgc tgcgaactgg gcgaacagcg tgaagcgttg   1020

ttggcggtga ccattccgga agaaaaaggc agcttcctca aattctgcca actgcttggc   1080

gggcgttcgg tcaccgagtt caactaccgt tttgccgatg ccaaaaacgc ctgcatcttt   1140

gtcggtgtgc gcctgagccg cggcctcgaa gagcgcaaag aaattttgca gatgctcaac   1200

gacggcggct acagcgtggt tgatctctcc gacgacgaaa tggcgaagct acacgtgcgc   1260

tatatggtcg gcggacgtcc atcgcatccg ttgcaggaac gcctctacag cttcgaattc   1320

ccggaatcac cgggcgcgct gctgcgcttc ctcaacacgc tgggtacgta ctggaacatt   1380

tctttgttcc actatcgcag ccatggcacc gactacgggc gcgtactggc ggcgttcgaa   1440

cttggcgacc atgaaccgga tttcgaaacc cggctgaatg agctgggcta cgattgccac   1500

gacgaaacca ataacccggc gttcaggttc tttttggcgg gttag                   1545


<210> SEQ ID NO 12
<211> LENGTH: 514
<212> TYPE: PRT
<213> ORGANISM: Escherichia coli
<220> FEATURE:
<223> OTHER INFORMATION: Native protein product ilvA, L-threonine
      dehydratase

<400> SEQUENCE: 12

Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
            20                  25                  30

Pro Leu Gln Lys Met Glu Lys Leu Ser Ser Arg Leu Asp Asn Val Ile
        35                  40                  45

Leu Val Lys Arg Glu Asp Arg Gln Pro Val His Ser Phe Lys Leu Arg
    50                  55                  60

Gly Ala Tyr Ala Met Met Ala Gly Leu Thr Glu Glu Gln Lys Ala His
65                  70                  75                  80

Gly Val Ile Thr Ala Ser Ala Gly Asn His Ala Gln Gly Val Ala Phe
                85                  90                  95

Ser Ser Ala Arg Leu Gly Val Lys Ala Leu Ile Val Met Pro Thr Ala
            100                 105                 110

Thr Ala Asp Ile Lys Val Asp Ala Val Arg Gly Phe Gly Gly Glu Val
        115                 120                 125

Leu Leu His Gly Ala Asn Phe Asp Glu Ala Lys Ala Lys Ala Ile Glu
    130                 135                 140

Leu Ser Gln Gln Gln Gly Phe Thr Trp Val Pro Pro Phe Asp His Pro
145                 150                 155                 160

Met Val Ile Ala Gly Gln Gly Thr Leu Ala Leu Glu Leu Leu Gln Gln
                165                 170                 175

Asp Ala His Leu Asp Arg Val Phe Val Pro Val Gly Gly Gly Gly Leu
            180                 185                 190

Ala Ala Gly Val Ala Val Leu Ile Lys Gln Leu Met Pro Gln Ile Lys
        195                 200                 205
```

```
Val Ile Ala Val Glu Ala Glu Asp Ser Ala Cys Leu Lys Ala Ala Leu
    210                 215                 220

Asp Ala Gly His Pro Val Asp Leu Pro Arg Val Gly Leu Phe Ala Glu
225                 230                 235                 240

Gly Val Ala Val Lys Arg Ile Gly Asp Glu Thr Phe Arg Leu Cys Gln
                245                 250                 255

Glu Tyr Leu Asp Asp Ile Ile Thr Val Asp Ser Asp Ala Ile Cys Ala
            260                 265                 270

Ala Met Lys Asp Leu Phe Glu Asp Val Arg Ala Val Ala Glu Pro Ser
        275                 280                 285

Gly Ala Leu Ala Leu Ala Gly Met Lys Lys Tyr Ile Ala Leu His Asn
    290                 295                 300

Ile Arg Gly Glu Arg Leu Ala His Ile Leu Ser Gly Ala Asn Val Asn
305                 310                 315                 320

Phe His Gly Leu Arg Tyr Val Ser Glu Arg Cys Glu Leu Gly Glu Gln
                325                 330                 335

Arg Glu Ala Leu Leu Ala Val Thr Ile Pro Glu Glu Lys Gly Ser Phe
            340                 345                 350

Leu Lys Phe Cys Gln Leu Leu Gly Gly Arg Ser Val Thr Glu Phe Asn
        355                 360                 365

Tyr Arg Phe Ala Asp Ala Lys Asn Ala Cys Ile Phe Val Gly Val Arg
    370                 375                 380

Leu Ser Arg Gly Leu Glu Glu Arg Lys Glu Ile Leu Gln Met Leu Asn
385                 390                 395                 400

Asp Gly Gly Tyr Ser Val Val Asp Leu Ser Asp Asp Glu Met Ala Lys
                405                 410                 415

Leu His Val Arg Tyr Met Val Gly Gly Arg Pro Ser His Pro Leu Gln
            420                 425                 430

Glu Arg Leu Tyr Ser Phe Glu Phe Pro Glu Ser Pro Gly Ala Leu Leu
        435                 440                 445

Arg Phe Leu Asn Thr Leu Gly Thr Tyr Trp Asn Ile Ser Leu Phe His
    450                 455                 460

Tyr Arg Ser His Gly Thr Asp Tyr Gly Arg Val Leu Ala Ala Phe Glu
465                 470                 475                 480

Leu Gly Asp His Glu Pro Asp Phe Glu Thr Arg Leu Asn Glu Leu Gly
                485                 490                 495

Tyr Asp Cys His Asp Glu Thr Asn Asn Pro Ala Phe Arg Phe Phe Leu
            500                 505                 510

Ala Gly


<210> SEQ ID NO 13
<211> LENGTH: 1725
<212> TYPE: DNA
<213> ORGANISM: Escherichia coli
<220> FEATURE:
<223> OTHER INFORMATION: ilvI, AHAS Iso III, large subunit

<400> SEQUENCE: 13

atggagatgt tgtctggagc cgagatggtc gtccgatcgc ttatcgatca gggcgttaaa      60

caagtattcg gttatcccgg aggcgcagtc cttgatattt atgatgcatt gcataccgtg     120

ggtggtattg atcatgtatt agttcgtcat gagcaggcgg cggtgcatat ggccgatggc     180

ctggcgcgcg cgaccgggga agtcggcgtc gtgctggtaa cgtcgggtcc aggggcgacc     240

aatgcgatta ctggcatcgc caccgcttat atggattcca ttccattagt tgtcctttcc     300
```

```
gggcaggtag cgacctcgtt gataggttac gatgcctttc aggagtgcga catggtgggg    360
atttcgcgac cggtggttaa acacagtttt ctggttaagc aaacggaaga cattccgcag    420
gtgctgaaaa aggctttctg gctggcggca agtggtcgcc caggaccagt agtcgttgat    480
ttaccgaaag atattcttaa tccggcgaac aaattaccct atgtctggcc ggagtcggtc    540
agtatgcgtt cttacaatcc cactactacc ggacataaag ggcaaattaa gcgtgctctg    600
caaacgctgg tagcggcaaa aaaaccggtt gtctacgtag gcggtggggc aatcacggcg    660
ggctgccatc agcagttgaa agaaacggtg gaggcgttga atctgcccgt tgtttgctca    720
ttgatggggc tgggggcgtt tccggcaacg catcgtcagg cactgggcat gctgggaatg    780
cacggtacct acgaagccaa tatgacgatg cataacgcgg atgtgatttt cgccgtcggg    840
gtacgatttg atgaccgaac gacgaacaat ctggcaaagt actgcccaaa tgccactgtt    900
ctgcatatcg atattgatcc tacttccatt tctaaaaccg tgactgcgga tatcccgatt    960
gtgggggatg ctcgccaggt cctcgaacaa atgcttgaac tcttgtcgca agaatccgcc   1020
catcaaccac tggatgagat ccgcgactgg tggcagcaaa ttgaacagtg gcgcgctcgt   1080
cagtgcctga aatatgacac tcacagtgaa aagattaaac cgcaggcggt gatcgagact   1140
ctttggcggt tgacgaaggg agacgcttac gtgacgtccg atgtcgggca gcaccagatg   1200
tttgctgcac tttattatcc attcgacaaa ccgcgtcgct ggatcaattc cggtggcctc   1260
ggcacgatgg gttttggttt acctgcggca ctgggcgtca aaatggcgtt gccagaagaa   1320
accgtggttt gcgtcactgg cgacggcagt attcagatga acatccagga actgtctacc   1380
gcgttgcaat acgagttgcc cgtactggtg gtgaatctca ataaccgcta tctggggatg   1440
gtgaagcagt ggcaggacat gatctattcc ggccgtcatt cacaatctta tatgcaatcg   1500
ctacccgatt tcgtccgtct ggcggaagcc tatgggcatg tcgggatcca gatttctcat   1560
ccgcatgagc tggaaagcaa acttagcgag gcgctggaac aggtgcgcaa taatcgcctg   1620
gtgtttgttg atgttaccgt cgatggcagc gagcacgtct acccgatgca gattcgcggg   1680
ggcggaatgg atgaaatgtg gttaagcaaa acggagagaa cctga                    1725
```

<210> SEQ ID NO 14
<211> LENGTH: 574
<212> TYPE: PRT
<213> ORGANISM: Escherichia coli
<220> FEATURE:
<223> OTHER INFORMATION: ilvI, AHAS Iso III, large subunit

<400> SEQUENCE: 14

```
Met Glu Met Leu Ser Gly Ala Glu Met Val Val Arg Ser Leu Ile Asp
1               5                   10                  15

Gln Gly Val Lys Gln Val Phe Gly Tyr Pro Gly Gly Ala Val Leu Asp
            20                  25                  30

Ile Tyr Asp Ala Leu His Thr Val Gly Gly Ile Asp His Val Leu Val
        35                  40                  45

Arg His Glu Gln Ala Ala Val His Met Ala Asp Gly Leu Ala Arg Ala
    50                  55                  60

Thr Gly Glu Val Gly Val Val Leu Val Thr Ser Gly Pro Gly Ala Thr
65                  70                  75                  80

Asn Ala Ile Thr Gly Ile Ala Thr Ala Tyr Met Asp Ser Ile Pro Leu
                85                  90                  95

Val Val Leu Ser Gly Gln Val Ala Thr Ser Leu Ile Gly Tyr Asp Ala
            100                 105                 110
```

```
Phe Gln Glu Cys Asp Met Val Gly Ile Ser Arg Pro Val Val Lys His
        115                 120                 125

Ser Phe Leu Val Lys Gln Thr Glu Asp Ile Pro Gln Val Leu Lys Lys
    130                 135                 140

Ala Phe Trp Leu Ala Ala Ser Gly Arg Pro Gly Pro Val Val Val Asp
145                 150                 155                 160

Leu Pro Lys Asp Ile Leu Asn Pro Ala Asn Lys Leu Pro Tyr Val Trp
                165                 170                 175

Pro Glu Ser Val Ser Met Arg Ser Tyr Asn Pro Thr Thr Thr Gly His
            180                 185                 190

Lys Gly Gln Ile Lys Arg Ala Leu Gln Thr Leu Val Ala Ala Lys Lys
        195                 200                 205

Pro Val Val Tyr Val Gly Gly Gly Ala Ile Thr Ala Gly Cys His Gln
    210                 215                 220

Gln Leu Lys Glu Thr Val Glu Ala Leu Asn Leu Pro Val Val Cys Ser
225                 230                 235                 240

Leu Met Gly Leu Gly Ala Phe Pro Ala Thr His Arg Gln Ala Leu Gly
                245                 250                 255

Met Leu Gly Met His Gly Thr Tyr Glu Ala Asn Met Thr Met His Asn
            260                 265                 270

Ala Asp Val Ile Phe Ala Val Gly Val Arg Phe Asp Asp Arg Thr Thr
        275                 280                 285

Asn Asn Leu Ala Lys Tyr Cys Pro Asn Ala Thr Val Leu His Ile Asp
    290                 295                 300

Ile Asp Pro Thr Ser Ile Ser Lys Thr Val Thr Ala Asp Ile Pro Ile
305                 310                 315                 320

Val Gly Asp Ala Arg Gln Val Leu Glu Gln Met Leu Glu Leu Leu Ser
                325                 330                 335

Gln Glu Ser Ala His Gln Pro Leu Asp Glu Ile Arg Asp Trp Trp Gln
            340                 345                 350

Gln Ile Glu Gln Trp Arg Ala Arg Gln Cys Leu Lys Tyr Asp Thr His
        355                 360                 365

Ser Glu Lys Ile Lys Pro Gln Ala Val Ile Glu Thr Leu Trp Arg Leu
    370                 375                 380

Thr Lys Gly Asp Ala Tyr Val Thr Ser Asp Val Gly Gln His Gln Met
385                 390                 395                 400

Phe Ala Ala Leu Tyr Tyr Pro Phe Asp Lys Pro Arg Arg Trp Ile Asn
                405                 410                 415

Ser Gly Gly Leu Gly Thr Met Gly Phe Gly Leu Pro Ala Ala Leu Gly
            420                 425                 430

Val Lys Met Ala Leu Pro Glu Glu Thr Val Val Cys Val Thr Gly Asp
        435                 440                 445

Gly Ser Ile Gln Met Asn Ile Gln Glu Leu Ser Thr Ala Leu Gln Tyr
    450                 455                 460

Glu Leu Pro Val Leu Val Val Asn Leu Asn Asn Arg Tyr Leu Gly Met
465                 470                 475                 480

Val Lys Gln Trp Gln Asp Met Ile Tyr Ser Gly Arg His Ser Gln Ser
                485                 490                 495

Tyr Met Gln Ser Leu Pro Asp Phe Val Arg Leu Ala Glu Ala Tyr Gly
            500                 505                 510

His Val Gly Ile Gln Ile Ser His Pro His Glu Leu Glu Ser Lys Leu
        515                 520                 525
```

-continued

```
Ser Glu Ala Leu Glu Gln Val Arg Asn Asn Arg Leu Val Phe Val Asp
    530                 535                 540

Val Thr Val Asp Gly Ser Glu His Val Tyr Pro Met Gln Ile Arg Gly
545                 550                 555                 560

Gly Gly Met Asp Glu Met Trp Leu Ser Lys Thr Glu Arg Thr
                565                 570


<210> SEQ ID NO 15
<211> LENGTH: 492
<212> TYPE: DNA
<213> ORGANISM: Escherichia coli
<220> FEATURE:
<223> OTHER INFORMATION: ilvH, AHAS Iso III, small subunit

<400> SEQUENCE: 15

atgcgccgga tattatcagt cttactcgaa aatgaatcag gcgcgttatc ccgcgtgatt      60

ggcctttttt cccagcgtgg ctacaacatt gaaagcctga ccgttgcgcc aaccgacgat     120

ccgacattat cgcgtatgac catccagacc gtgggcgatg aaaaagtact tgagcagatc     180

gaaaagcaat tacacaaact ggtcgatgtc ttgcgcgtga gtgagttggg gcagggcgcg     240

catgttgagc gggaaatcat gctggtgaaa attcaggcca gcggttacgg gcgtgacgaa     300

gtgaaacgta atacggaaat attccgtggg caaattatcg atgtcacacc ctcgctttat     360

accgttcaat tagcaggcac cagcggtaag cttgatgcat tttagcatc gattcgcgat      420

gtggcgaaaa ttgtggaggt tgctcgctct ggtgtggtcg gactttcgcg cggcgataaa     480

ataatgcgtt ga                                                          492


<210> SEQ ID NO 16
<211> LENGTH: 163
<212> TYPE: PRT
<213> ORGANISM: Escherichia coli
<220> FEATURE:
<223> OTHER INFORMATION: ilvH, AHAS Iso III, small subunit

<400> SEQUENCE: 16

Met Arg Arg Ile Leu Ser Val Leu Leu Glu Asn Glu Ser Gly Ala Leu
1               5                   10                  15

Ser Arg Val Ile Gly Leu Phe Ser Gln Arg Gly Tyr Asn Ile Glu Ser
            20                  25                  30

Leu Thr Val Ala Pro Thr Asp Asp Pro Thr Leu Ser Arg Met Thr Ile
        35                  40                  45

Gln Thr Val Gly Asp Glu Lys Val Leu Glu Gln Ile Glu Lys Gln Leu
    50                  55                  60

His Lys Leu Val Asp Val Leu Arg Val Ser Glu Leu Gly Gln Gly Ala
65                  70                  75                  80

His Val Glu Arg Glu Ile Met Leu Val Lys Ile Gln Ala Ser Gly Tyr
                85                  90                  95

Gly Arg Asp Glu Val Lys Arg Asn Thr Glu Ile Phe Arg Gly Gln Ile
            100                 105                 110

Ile Asp Val Thr Pro Ser Leu Tyr Thr Val Gln Leu Ala Gly Thr Ser
        115                 120                 125

Gly Lys Leu Asp Ala Phe Leu Ala Ser Ile Arg Asp Val Ala Lys Ile
    130                 135                 140

Val Glu Val Ala Arg Ser Gly Val Val Gly Leu Ser Arg Gly Asp Lys
145                 150                 155                 160

Ile Met Arg
```

```
<210> SEQ ID NO 17
<211> LENGTH: 2463
<212> TYPE: DNA
<213> ORGANISM: Escherichia coli
<220> FEATURE:
<223> OTHER INFORMATION: thrA, aspartate kinase and homoserine
      dehydrogenase, bifunctional

<400> SEQUENCE: 17

atgcgagtgt tgaagttcgg cggtacatca gtggcaaatg cagaacgttt tctgcgtgtt     60
gccgatattc tggaaagcaa tgccaggcag ggcaggtgg ccaccgtcct ctctgccccc    120
gccaaaatca ccaaccacct ggtggcgatg attgaaaaaa ccattagcgg ccaggatgct    180
ttacccaata tcagcgatgc cgaacgtatt tttgccgaac ttttgacggg actcgccgcc    240
gcccagccgg ggttcccgct ggcgcaattg aaaactttcg tcgatcagga atttgcccaa    300
ataaaacatg tcctgcatgg cattagtttg ttggggcagt gcccggatag catcaacgct    360
gcgctgattt gccgtggcga gaaaatgtcg atcgccatta tggccggcgt attagaagcg    420
cgcggtcaca acgttactgt tatcgatccg gtcgaaaaac tgctggcagt ggggcattac    480
ctcgaatcta ccgtcgatat tgctgagtcc acccgccgta ttgcggcaag ccgcattccg    540
gctgatcaca tggtgctgat ggcaggtttc accgccggta atgaaaaagg cgaactggtg    600
gtgcttggac gcaacggttc cgactactct gctgcggtgc tggctgcctg tttacgcgcc    660
gattgttgcg agatttggac ggacgttgac ggggtctata cctgcgaccc gcgtcaggtg    720
cccgatgcga ggttgttgaa gtcgatgtcc taccaggaag cgatggagct ttcctacttc    780
ggcgctaaag ttcttcaccc ccgcaccatt acccccatcg cccagttcca gatcccttgc    840
ctgattaaaa ataccggaaa tcctcaagca ccaggtacgc tcattggtgc cagccgtgat    900
gaagacgaat taccggtcaa gggcatttcc aatctgaata acatggcaat gttcagcgtt    960
tctggtccgg ggatgaaagg gatggtcggc atggcggcgc gcgtctttgc agcgatgtca   1020
cgcgcccgta tttccgtggt gctgattacg caatcatctt ccgaatacag catcagtttc   1080
tgcgttccac aaagcgactg tgtgcgagct gaacgggcaa tgcaggaaga gttctacctg   1140
gaactgaaag aaggcttact ggagccgctg gcagtgacgg aacggctggc cattatctcg   1200
gtggtaggtg atggtatgcg caccttgcgt gggatctcgg cgaaattctt tgccgcactg   1260
gcccgcgcca atatcaacat tgtcgccatt gctcagggat cttctgaacg ctcaatctct   1320
gtcgtggtaa ataacgatga tgcgaccact ggcgtgcgcg ttactcatca gatgctgttc   1380
aataccgatc aggttatcga agtgtttgtg attggcgtcg gtggcgttgg cggtgcgctg   1440
ctggagcaac tgaagcgtca gcaaagctgg ctgaagaata aacatatcga cttacgtgtc   1500
tgcggtgttg ccaactcgaa ggctctgctc accaatgtac atggccttaa tctggaaaac   1560
tggcaggaag aactggcgca agccaaagag ccgtttaatc tcgggcgctt aattcgcctc   1620
gtgaaagaat atcatctgct gaacccggtc attgttgact gcacttccag ccaggcagtg   1680
gcggatcaat atgccgactt cctgcgcgaa ggtttccacg ttgtcacgcc gaacaaaaag   1740
gccaacacct cgtcgatgga ttactaccat cagttgcgtt atgcggcgga aaaatcgcgg   1800
cgtaaattcc tctatgacac caacgttggg gctggattac cggttattga gaacctgcaa   1860
aatctgctca atgcaggtga tgaattgatg aagttctccg gcattctttc tggttcgctt   1920
tcttatatct tcggcaagtt agacgaaggc atgagtttct ccgaggcgac cacgctggcg   1980
cgggaaatgg gttataccga accggacccg cgagatgatc tttctggtat ggatgtggcg   2040
```

-continued

```
cgtaaactat tgattctcgc tcgtgaaacg ggacgtgaac tggagctggc ggatattgaa   2100

attgaacctg tgctgcccgc agagtttaac gccgagggtg atgttgccgc ttttatggcg   2160

aatctgtcac aactcgacga tctctttgcc gcgcgcgtgg cgaaggcccg tgatgaagga   2220

aaagttttgc gctatgttgg caatattgat gaagatggcg tctgccgcgt gaagattgcc   2280

gaagtggatg gtaatgatcc gctgttcaaa gtgaaaaatg gcgaaaacgc cctggccttc   2340

tatagccact attatcagcc gctgccgttg gtactgcgcg gatatggtgc gggcaatgac   2400

gttacagctg ccggtgtctt tgctgatctg ctacgtaccc tctcatggaa gttaggagtc   2460

tga                                                                 2463


<210> SEQ ID NO 18
<211> LENGTH: 820
<212> TYPE: PRT
<213> ORGANISM: Escherichia coli
<220> FEATURE:
<223> OTHER INFORMATION: thrA, aspartate kinase and homoserine
      dehydrogenase, bifunctional

<400> SEQUENCE: 18

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile
    50                  55                  60

Ser Asp Ala Glu Arg Ile Phe Ala Glu Leu Leu Thr Gly Leu Ala Ala
65                  70                  75                  80

Ala Gln Pro Gly Phe Pro Leu Ala Gln Leu Lys Thr Phe Val Asp Gln
                85                  90                  95

Glu Phe Ala Gln Ile Lys His Val Leu His Gly Ile Ser Leu Leu Gly
            100                 105                 110

Gln Cys Pro Asp Ser Ile Asn Ala Ala Leu Ile Cys Arg Gly Glu Lys
        115                 120                 125

Met Ser Ile Ala Ile Met Ala Gly Val Leu Glu Ala Arg Gly His Asn
    130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
            180                 185                 190

Gly Asn Glu Lys Gly Glu Leu Val Val Leu Gly Arg Asn Gly Ser Asp
        195                 200                 205

Tyr Ser Ala Ala Val Leu Ala Ala Cys Leu Arg Ala Asp Cys Cys Glu
    210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln Glu Ala Met Glu
                245                 250                 255

Leu Ser Tyr Phe Gly Ala Lys Val Leu His Pro Arg Thr Ile Thr Pro
            260                 265                 270

Ile Ala Gln Phe Gln Ile Pro Cys Leu Ile Lys Asn Thr Gly Asn Pro
```

```
        275                 280                 285

Gln Ala Pro Gly Thr Leu Ile Gly Ala Ser Arg Asp Glu Asp Glu Leu
    290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Ser Val Val Leu Ile Thr Gln Ser
            340                 345                 350

Ser Ser Glu Tyr Ser Ile Ser Phe Cys Val Pro Gln Ser Asp Cys Val
        355                 360                 365

Arg Ala Glu Arg Ala Met Gln Glu Glu Phe Tyr Leu Glu Leu Lys Glu
    370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
            420                 425                 430

Gly Ser Ser Glu Arg Ser Ile Ser Val Val Val Asn Asn Asp Asp Ala
        435                 440                 445

Thr Thr Gly Val Arg Val Thr His Gln Met Leu Phe Asn Thr Asp Gln
    450                 455                 460

Val Ile Glu Val Phe Val Ile Gly Val Gly Gly Val Gly Gly Ala Leu
465                 470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
            500                 505                 510

Val His Gly Leu Asn Leu Glu Asn Trp Gln Glu Glu Leu Ala Gln Ala
        515                 520                 525

Lys Glu Pro Phe Asn Leu Gly Arg Leu Ile Arg Leu Val Lys Glu Tyr
    530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
                565                 570                 575

Pro Asn Lys Lys Ala Asn Thr Ser Ser Met Asp Tyr Tyr His Gln Leu
            580                 585                 590

Arg Tyr Ala Ala Glu Lys Ser Arg Arg Lys Phe Leu Tyr Asp Thr Asn
        595                 600                 605

Val Gly Ala Gly Leu Pro Val Ile Glu Asn Leu Gln Asn Leu Leu Asn
    610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
                645                 650                 655

Thr Thr Leu Ala Arg Glu Met Gly Tyr Thr Glu Pro Asp Pro Arg Asp
            660                 665                 670

Asp Leu Ser Gly Met Asp Val Ala Arg Lys Leu Leu Ile Leu Ala Arg
        675                 680                 685

Glu Thr Gly Arg Glu Leu Glu Leu Ala Asp Ile Glu Ile Glu Pro Val
    690                 695                 700
```

```
Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
                725                 730                 735

Arg Asp Glu Gly Lys Val Leu Arg Tyr Val Gly Asn Ile Asp Glu Asp
            740                 745                 750

Gly Val Cys Arg Val Lys Ile Ala Glu Val Asp Gly Asn Asp Pro Leu
        755                 760                 765

Phe Lys Val Lys Asn Gly Glu Asn Ala Leu Ala Phe Tyr Ser His Tyr
    770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
                805                 810                 815

Lys Leu Gly Val
            820


<210> SEQ ID NO 19
<211> LENGTH: 285
<212> TYPE: DNA
<213> ORGANISM: Escherichia coli
<220> FEATURE:
<223> OTHER INFORMATION: araBAD promoter

<400> SEQUENCE: 19

aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccat                    285


<210> SEQ ID NO 20
<211> LENGTH: 879
<212> TYPE: DNA
<213> ORGANISM: Escherichia coli
<220> FEATURE:
<223> OTHER INFORMATION: Gene araC

<400> SEQUENCE: 20

atggctgaag cgcaaaatga tcccctgctg ccgggatact cgtttaatgc ccatctggtg     60

gcgggtttaa cgccgattga ggccaacggt tatctcgatt tttttatcga ccgaccgctg    120

ggaatgaaag gttatattct caatctcacc attcgcggtc aggggggtggt gaaaaatcag   180

ggacgagaat ttgtttgccg accgggtgat attttgctgt tcccgccagg agagattcat    240

cactacggtc gtcatccgga ggctcgcgaa tggtatcacc agtgggttta ctttcgtccg    300

cgcgcctact ggcatgaatg gcttaactgg ccgtcaatat ttgccaatac ggggttcttt    360

cgcccggatg aagcgcacca gccgcatttc agcgacctgt ttgggcaaat cattaacgcc    420

gggcaagggg aagggcgcta ttcggagctg ctggcgataa atctgcttga gcaattgtta    480

ctgcggcgca tggaagcgat taacgagtcg ctccatccac cgatggataa tcgggtacgc    540

gaggcttgtc agtacatcag cgatcacctg gcagacagca attttgatat cgccagcgtc    600

gcacagcatg tttgcttgtc gccgtcgcgt ctgtcacatc ttttccgcca gcagttaggg    660

attagcgtct taagctggcg cgaggaccaa cgtatcagcc aggcgaagct gcttttgagc    720
```

```
accacccgga tgcctatcgc caccgtcggt cgcaatgttg gttttgacga tcaactctat    780

ttctcgcggg tatttaaaaa atgcaccggg gccagcccga gcgagttccg tgccggttgt    840

gaagaaaaag tgaatgatgt agccgtcaag ttgtcataa                           879


<210> SEQ ID NO 21
<211> LENGTH: 81
<212> TYPE: DNA
<213> ORGANISM: Escherichia coli
<220> FEATURE:
<223> OTHER INFORMATION: Pm promoter

<400> SEQUENCE: 21

agtccagcct tgcaagaagc ggatacagga gtgcaaaaaa tggctatctc tagaaaggcc     60

taccccttag gctttatgca a                                               81


<210> SEQ ID NO 22
<211> LENGTH: 1135
<212> TYPE: DNA
<213> ORGANISM: Escherichia coli
<220> FEATURE:
<223> OTHER INFORMATION: XylS promoter and gene xylS

<400> SEQUENCE: 22

cttggcgtta tttttgcttg gaaaagtggt cactgattgc aaaaaggatg gcgcaacgtg     60

gcaatggggg taacccgtat acgcatcacg tcgagatgca ttttcatcga cttggcgcct    120

ttctacatca caccaagcag cccacattaa aataagagaa ccgtgaacta tggatttttg    180

cttattgaac gagaaaagtc agatcttcgt ccacgccgag ccctatgcag tctccgatta    240

tgttaaccag tatgtcggta cgcactctat tcgcctgccc aagggcgggc ccccggcagg    300

caggctgcac cacagaatct tcggatgcct cgacctgtgt cgaatcagct acggcggtag    360

cgtgagggta atctcgcctg gattagagac ctgttatcat ctgcaaataa tactcaaagg    420

ccattgcctg tggcgtggcc atggccagga gcactatttt gcgccgggcg aactattgct    480

gctcaatccg gatgaccaag ccgacctgac ctattcagaa gattgcgaga aatttatcgt    540

taaattgccc tcagtggtcc ttgatcgggc atgcagtgac aacaattggc acaagccgag    600

ggagggtatc cgtttcgccg cgcgacacaa tctccagcaa ctcgatggct ttatcaatct    660

actcgggtta gtttgtgacg aagcggaaca tacaaagtcg atgcctcggg tccaagagca    720

ctatgcgggg atcatcgctt ccaagctgct cgaaatgctg ggcagcaatg tcagccgtga    780

aattttcagc aaaggtaacc cgtctttcga gcgagtcgtt caattcattg aggagaatct    840

caaacggaat atcagccttg agcggttagc ggagctggcg atgatgagtc cacgctcgct    900

ctacaatttg ttcgagaagc atgccggcac cacgccgaag aactacatcc gcaaccgcaa    960

gctcgaaagc atccgcgcct gcttgaacga tcccagtgcc aatgtgcgta gtataactga   1020

gatagcccta gactacggct tcttacattt gggacgcttc gctgaaaact ataggagcgc   1080

gttcggcgag ttgccttccg acaccctgcg tcaatgcaaa aaggaagtgg cttga        1135


<210> SEQ ID NO 23
<211> LENGTH: 1689
<212> TYPE: DNA
<213> ORGANISM: Escherichia coli
<220> FEATURE:
<223> OTHER INFORMATION: ilvB, AHAS Iso I, large subunit

<400> SEQUENCE: 23

atggcaagtt cgggcacaac atcgacgcgt aagcgcttta ccggcgcaga atttatcgtt     60
```

```
catttcctgg aacagcaggg cattaagatt gtgacaggca ttccgggcgg ttctatcctg    120

cctgtttacg atgccttaag ccaaagcacg caaatccgcc atattctggc ccgtcatgaa    180

cagggcgcgg gctttatcgc tcagggaatg gcgcgcaccg acggtaaacc ggcggtctgt    240

atggcctgta gcggaccggg tgcgactaac ctggtgaccg ccattgccga tgcgcggctg    300

gactccatcc cgctgatttg catcactggt caggttcccg cctcgatgat cggcaccgac    360

gccttccagg aagtggacac ctacggcatc tctatcccca tcaccaaaca caactatctg    420

gtcagacata tcgaagaact cccgcaggtc atgagcgatg ccttccgcat tgcgcaatca    480

ggccgcccag gcccggtgtg gatagacatt cctaaggatg tgcaaacggc agtttttgag    540

attgaaacac agcccgctat ggcagaaaaa gccgccgccc ccgcctttag cgaagaaagc    600

attcgtgacg cagcggcgat gattaacgct gccaaacgcc cggtgcttta tctgggcggc    660

ggtgtgatca atgcgcccgc acgggtgcgt gaactggcgg agaaagcgca actgcctacc    720

accatgactt taatggcgct gggcatgttg ccaaaagcgc atccgttgtc gctgggtatg    780

ctggggatgc acggcgtgcg cagcaccaac tatattttgc aggaggcgga tttgttgata    840

gtgctcggtg cgcgttttga tgaccgggcg attggcaaaa ccgagcagtt ctgtccgaat    900

gccaaaatca ttcatgtcga tatcgaccgt gcagagctgg gtaaaatcaa gcagccgcac    960

gtggcgattc aggcggatgt tgatgacgtg ctggcgcagt tgatcccgct ggtggaagcg   1020

caaccgcgtg cagagtggca ccagttggta gcggatttgc agcgtgagtt tccgtgtcca   1080

atcccgaaag cgtgcgatcc gttaagccat tacggcctga tcaacgccgt tgccgcctgt   1140

gtcgatgaca atgcaattat caccaccgac gttggtcagc atcagatgtg gaccgcgcaa   1200

gcttatccgc tcaatcgccc acgccagtgg ctgacctccg gtgggctggg cacgatgggt   1260

tttggcctgc ctgcggcgat tggcgctgcg ctggcgaacc cggatcgcaa agtgttgtgt   1320

ttctccggcg acggcagcct gatgatgaat attcaggaga tggcgaccgc cagtgaaaat   1380

cagctggatg tcaaaatcat tctgatgaac aacgaagcgc tggggctggt gcatcagcaa   1440

cagagtctgt tctacgagca aggcgttttt gccgccacct atccgggcaa aatcaacttt   1500

atgcagattg ccgccggatt cggcctcgaa acctgtgatt tgaataacga agccgatccg   1560

caggcttcat tgcaggaaat catcaatcgc cctggcccgg cgctgatcca tgtgcgcatt   1620

gatgccgaag aaaaagttta cccgatggtg ccgccaggtg cggcgaatac tgaaatggtg   1680

ggggaataa                                                           1689
```

```
<210> SEQ ID NO 24
<211> LENGTH: 562
<212> TYPE: PRT
<213> ORGANISM: Escherichia coli
<220> FEATURE:
<223> OTHER INFORMATION: ilvB, AHAS Iso I, large subunit

<400> SEQUENCE: 24

Met Ala Ser Ser Gly Thr Thr Ser Thr Arg Lys Arg Phe Thr Gly Ala
1               5                   10                  15

Glu Phe Ile Val His Phe Leu Glu Gln Gln Gly Ile Lys Ile Val Thr
            20                  25                  30

Gly Ile Pro Gly Gly Ser Ile Leu Pro Val Tyr Asp Ala Leu Ser Gln
        35                  40                  45

Ser Thr Gln Ile Arg His Ile Leu Ala Arg His Glu Gln Gly Ala Gly
    50                  55                  60
```

-continued

```
Phe Ile Ala Gln Gly Met Ala Arg Thr Asp Gly Lys Pro Ala Val Cys
65                  70                  75                  80

Met Ala Cys Ser Gly Pro Gly Ala Thr Asn Leu Val Thr Ala Ile Ala
                85                  90                  95

Asp Ala Arg Leu Asp Ser Ile Pro Leu Ile Cys Ile Thr Gly Gln Val
            100                 105                 110

Pro Ala Ser Met Ile Gly Thr Asp Ala Phe Gln Glu Val Asp Thr Tyr
        115                 120                 125

Gly Ile Ser Ile Pro Ile Thr Lys His Asn Tyr Leu Val Arg His Ile
    130                 135                 140

Glu Glu Leu Pro Gln Val Met Ser Asp Ala Phe Arg Ile Ala Gln Ser
145                 150                 155                 160

Gly Arg Pro Gly Pro Val Trp Ile Asp Ile Pro Lys Asp Val Gln Thr
                165                 170                 175

Ala Val Phe Glu Ile Glu Thr Gln Pro Ala Met Ala Glu Lys Ala Ala
            180                 185                 190

Ala Pro Ala Phe Ser Glu Glu Ser Ile Arg Asp Ala Ala Ala Met Ile
        195                 200                 205

Asn Ala Ala Lys Arg Pro Val Leu Tyr Leu Gly Gly Gly Val Ile Asn
    210                 215                 220

Ala Pro Ala Arg Val Arg Glu Leu Ala Glu Lys Ala Gln Leu Pro Thr
225                 230                 235                 240

Thr Met Thr Leu Met Ala Leu Gly Met Leu Pro Lys Ala His Pro Leu
                245                 250                 255

Ser Leu Gly Met Leu Gly Met His Gly Val Arg Ser Thr Asn Tyr Ile
            260                 265                 270

Leu Gln Glu Ala Asp Leu Leu Ile Val Leu Gly Ala Arg Phe Asp Asp
        275                 280                 285

Arg Ala Ile Gly Lys Thr Glu Gln Phe Cys Pro Asn Ala Lys Ile Ile
    290                 295                 300

His Val Asp Ile Asp Arg Ala Glu Leu Gly Lys Ile Lys Gln Pro His
305                 310                 315                 320

Val Ala Ile Gln Ala Asp Val Asp Asp Val Leu Ala Gln Leu Ile Pro
                325                 330                 335

Leu Val Glu Ala Gln Pro Arg Ala Glu Trp His Gln Leu Val Ala Asp
            340                 345                 350

Leu Gln Arg Glu Phe Pro Cys Pro Ile Pro Lys Ala Cys Asp Pro Leu
        355                 360                 365

Ser His Tyr Gly Leu Ile Asn Ala Val Ala Ala Cys Val Asp Asp Asn
    370                 375                 380

Ala Ile Ile Thr Thr Asp Val Gly Gln His Gln Met Trp Thr Ala Gln
385                 390                 395                 400

Ala Tyr Pro Leu Asn Arg Pro Arg Gln Trp Leu Thr Ser Gly Gly Leu
                405                 410                 415

Gly Thr Met Gly Phe Gly Leu Pro Ala Ala Ile Gly Ala Ala Leu Ala
            420                 425                 430

Asn Pro Asp Arg Lys Val Leu Cys Phe Ser Gly Asp Gly Ser Leu Met
        435                 440                 445

Met Asn Ile Gln Glu Met Ala Thr Ala Ser Glu Asn Gln Leu Asp Val
    450                 455                 460

Lys Ile Ile Leu Met Asn Asn Glu Ala Leu Gly Leu Val His Gln Gln
465                 470                 475                 480

Gln Ser Leu Phe Tyr Glu Gln Gly Val Phe Ala Ala Thr Tyr Pro Gly
```

```
            485                 490                 495

Lys Ile Asn Phe Met Gln Ile Ala Ala Gly Phe Gly Leu Glu Thr Cys
            500                 505                 510

Asp Leu Asn Asn Glu Ala Asp Pro Gln Ala Ser Leu Gln Glu Ile Ile
        515                 520                 525

Asn Arg Pro Gly Pro Ala Leu Ile His Val Arg Ile Asp Ala Glu Glu
    530                 535                 540

Lys Val Tyr Pro Met Val Pro Pro Gly Ala Ala Asn Thr Glu Met Val
545                 550                 555                 560

Gly Glu


<210> SEQ ID NO 25
<211> LENGTH: 291
<212> TYPE: DNA
<213> ORGANISM: Escherichia coli
<220> FEATURE:
<223> OTHER INFORMATION: ilvN, AHAS Iso I, small subunit

<400> SEQUENCE: 25

atgcaaaaca caactcatga caacgtaatt ctggagctca ccgttcgcaa ccatccgggc      60

gtaatgaccc acgtttgtgg cctttttgcc cgccgcgctt ttaacgttga aggcattctt     120

tgtctgccga ttcaggacag cgacaaaagc catatctggc tactggtcaa tgacgaccag     180

cgtctggagc agatgataag ccaaatcgat aagctggaag atgtcgtgaa agtgcagcgt     240

aatcagtccg atccgacgat gtttaacaag atcgcggtgt tttttcagta a              291


<210> SEQ ID NO 26
<211> LENGTH: 96
<212> TYPE: PRT
<213> ORGANISM: Escherichia coli
<220> FEATURE:
<223> OTHER INFORMATION: ilvN, AHAS Iso I, small subunit

<400> SEQUENCE: 26

Met Gln Asn Thr Thr His Asp Asn Val Ile Leu Glu Leu Thr Val Arg
1               5                   10                  15

Asn His Pro Gly Val Met Thr His Val Cys Gly Leu Phe Ala Arg Arg
            20                  25                  30

Ala Phe Asn Val Glu Gly Ile Leu Cys Leu Pro Ile Gln Asp Ser Asp
        35                  40                  45

Lys Ser His Ile Trp Leu Leu Val Asn Asp Asp Gln Arg Leu Glu Gln
    50                  55                  60

Met Ile Ser Gln Ile Asp Lys Leu Glu Asp Val Val Lys Val Gln Arg
65                  70                  75                  80

Asn Gln Ser Asp Pro Thr Met Phe Asn Lys Ile Ala Val Phe Phe Gln
                85                  90                  95


<210> SEQ ID NO 27
<211> LENGTH: 1647
<212> TYPE: DNA
<213> ORGANISM: Shigella boydii
<220> FEATURE:
<223> OTHER INFORMATION: AHAS II, large subunit

<400> SEQUENCE: 27

atgaatggcg cacagtgggt ggtacatgcg ttgcgggcac agggtgtgaa caccgttttc      60

ggttatccgg gtggcgcaat tatgccggtt tacgatgcat tgtatgacgg cggcgtggag     120

cacttgctgt gccgacatga gcagggtgcg gcaatggcgg ctatcggtta tgcccgtgct     180
```

```
accggcaaaa ctggcgtatg tatcgccacg tctggtccgg gcgcaaccaa cctgataacc    240
gggcttgcgg acgcactgtt agattctatc cctgttgttg ccatcaccgg tcaagtgtcc    300
gcaccgttta tcggcactga tgcatttcag gaagtggatg tcctgggatt gtcgttagcc    360
tgtaccaagc acagctttct ggtgcagtcg ctggaagagt tgccgcgcat tatggctgaa    420
gcattcgacg ttgccagctc aggtcgtcct ggtccggttc tggtcgatat cccaaaagat    480
atccagctag ccagcggtga cctggaaccg tggttcacca ccgttgaaaa cgaagtgact    540
ttcccacatg ccgaagttga gcaagcgcgc cagatgctgg caaaagcgca aaaaccgatg    600
ctgtacgttg gtggtggcgt gggtatggcg caggcagttc ctgctttacg agaatttctc    660
gctaccacaa aaatgcctgc cacctgcacg ctgaaagggc tgggcgcagt tgaagcagat    720
tatccgtact atctgggcat gctgggaatg catggcacca aagcggcgaa cttcgcggtg    780
caggagtgcg acttgctgat cgccgtgggt gcacgttttg atgaccgggt gaccggcaaa    840
ctgaacacct tcgcaccaca cgccagcgtt atccatatgg atatcgaccc ggcagaaatg    900
aacaagctgc gtcaggcaca tgtggcatta caaggtgatt taaatgctct gttaccagaa    960
ttacagcagc cgttaaatat caatgactgg cagcaatact gcgcgcagct gcgtgatgaa   1020
catgcctggc gttacgacca tcccggcgac gctatctacg cgccgttgtt gttaaaacaa   1080
ctgtcggatc gtaaacctgc ggattgcgtc gtgaccacag atgtggggca gcaccagatg   1140
tgggctgcgc aacacatcgc ccacactcgc ccggaaaatt tcatcacctc cagcggctta   1200
ggcactatgg gttttggttt accagcggcg gttggcgcac aagtcgcgcg accgaacgat   1260
accgtcgtct gtatctccgg tgacggctct ttcatgatga atgtgcaaga gctgggcacc   1320
gtaaaacgca agcagttacc gttgaaaatc gtcttactcg ataaccaacg gttagggatg   1380
gttcgacaat ggcagcaact gttttttcag gaacgataca gcgaaaccac ccttactgat   1440
aaccccgatt tcctcatgtt agccagcgcc ttcggcatcc ctggccaaca catcacccgt   1500
aaagaccagg ttgaagcggc actcgacacc atgctgaaca gtgatgggcc atacctgctt   1560
catgtctcaa tcgacgaact tgagaacgtc tggccgctgg tgccgcctgg cgccagtaat   1620
tcagaaatgt tggagaaatt atcatga                                       1647
```

<210> SEQ ID NO 28
<211> LENGTH: 548
<212> TYPE: PRT
<213> ORGANISM: Shigella boydii
<220> FEATURE:
<223> OTHER INFORMATION: AHAS II, large subunit

<400> SEQUENCE: 28

```
Met Asn Gly Ala Gln Trp Val Val His Ala Leu Arg Ala Gln Gly Val
1               5                   10                  15

Asn Thr Val Phe Gly Tyr Pro Gly Gly Ala Ile Met Pro Val Tyr Asp
            20                  25                  30

Ala Leu Tyr Asp Gly Gly Val Glu His Leu Leu Cys Arg His Glu Gln
        35                  40                  45

Gly Ala Ala Met Ala Ala Ile Gly Tyr Ala Arg Ala Thr Gly Lys Thr
    50                  55                  60

Gly Val Cys Ile Ala Thr Ser Gly Pro Gly Ala Thr Asn Leu Ile Thr
65                  70                  75                  80

Gly Leu Ala Asp Ala Leu Leu Asp Ser Ile Pro Val Val Ala Ile Thr
                85                  90                  95
```

```
Gly Gln Val Ser Ala Pro Phe Ile Gly Thr Asp Ala Phe Gln Glu Val
            100                 105                 110

Asp Val Leu Gly Leu Ser Leu Ala Cys Thr Lys His Ser Phe Leu Val
        115                 120                 125

Gln Ser Leu Glu Glu Leu Pro Arg Ile Met Ala Glu Ala Phe Asp Val
    130                 135                 140

Ala Ser Ser Gly Arg Pro Gly Pro Val Leu Val Asp Ile Pro Lys Asp
145                 150                 155                 160

Ile Gln Leu Ala Ser Gly Asp Leu Glu Pro Trp Phe Thr Thr Val Glu
                165                 170                 175

Asn Glu Val Thr Phe Pro His Ala Glu Val Glu Gln Ala Arg Gln Met
            180                 185                 190

Leu Ala Lys Ala Gln Lys Pro Met Leu Tyr Val Gly Gly Gly Val Gly
        195                 200                 205

Met Ala Gln Ala Val Pro Ala Leu Arg Glu Phe Leu Ala Thr Thr Lys
    210                 215                 220

Met Pro Ala Thr Cys Thr Leu Lys Gly Leu Gly Ala Val Glu Ala Asp
225                 230                 235                 240

Tyr Pro Tyr Tyr Leu Gly Met Leu Gly Met His Gly Thr Lys Ala Ala
                245                 250                 255

Asn Phe Ala Val Gln Glu Cys Asp Leu Leu Ile Ala Val Gly Ala Arg
            260                 265                 270

Phe Asp Asp Arg Val Thr Gly Lys Leu Asn Thr Phe Ala Pro His Ala
        275                 280                 285

Ser Val Ile His Met Asp Ile Asp Pro Ala Glu Met Asn Lys Leu Arg
    290                 295                 300

Gln Ala His Val Ala Leu Gln Gly Asp Leu Asn Ala Leu Leu Pro Glu
305                 310                 315                 320

Leu Gln Gln Pro Leu Asn Ile Asn Asp Trp Gln Gln Tyr Cys Ala Gln
                325                 330                 335

Leu Arg Asp Glu His Ala Trp Arg Tyr Asp His Pro Gly Asp Ala Ile
            340                 345                 350

Tyr Ala Pro Leu Leu Leu Lys Gln Leu Ser Asp Arg Lys Pro Ala Asp
        355                 360                 365

Cys Val Val Thr Thr Asp Val Gly Gln His Gln Met Trp Ala Ala Gln
    370                 375                 380

His Ile Ala His Thr Arg Pro Glu Asn Phe Ile Thr Ser Ser Gly Leu
385                 390                 395                 400

Gly Thr Met Gly Phe Gly Leu Pro Ala Ala Val Gly Ala Gln Val Ala
                405                 410                 415

Arg Pro Asn Asp Thr Val Val Cys Ile Ser Gly Asp Gly Ser Phe Met
            420                 425                 430

Met Asn Val Gln Glu Leu Gly Thr Val Lys Arg Lys Gln Leu Pro Leu
        435                 440                 445

Lys Ile Val Leu Leu Asp Asn Gln Arg Leu Gly Met Val Arg Gln Trp
    450                 455                 460

Gln Gln Leu Phe Phe Gln Glu Arg Tyr Ser Glu Thr Thr Leu Thr Asp
465                 470                 475                 480

Asn Pro Asp Phe Leu Met Leu Ala Ser Ala Phe Gly Ile Pro Gly Gln
                485                 490                 495

His Ile Thr Arg Lys Asp Gln Val Glu Ala Ala Leu Asp Thr Met Leu
            500                 505                 510

Asn Ser Asp Gly Pro Tyr Leu Leu His Val Ser Ile Asp Glu Leu Glu
```

515 520 525

Asn Val Trp Pro Leu Val Pro Pro Gly Ala Ser Asn Ser Glu Met Leu
530 535 540

Glu Lys Leu Ser
545

<210> SEQ ID NO 29
<211> LENGTH: 264
<212> TYPE: DNA
<213> ORGANISM: Shigella boydii
<220> FEATURE:
<223> OTHER INFORMATION: AHAS II, small subunit

<400> SEQUENCE: 29
atgatgcaat atcaggtcaa tgtatcggct cgcttcaatc cggaaacctt agaacgtgtt 60
ttacgcgtgg tgcgtcatcg tggtttccac gtctgctcaa tgaatatggc cgccgccagc 120
gatgcacaaa atataaatat cgaattgacc gttgccagcc cacggtcggt cgacttactg 180
tttagtcagt taaataaact ggtggacgtc gcacacgttg ccatctgcca gagcacaacc 240
acatcacaac aaatccgcgc ctga 264

<210> SEQ ID NO 30
<211> LENGTH: 87
<212> TYPE: PRT
<213> ORGANISM: Shigella boydii
<220> FEATURE:
<223> OTHER INFORMATION: AHAS II, small subunit

<400> SEQUENCE: 30

Met Met Gln Tyr Gln Val Asn Val Ser Ala Arg Phe Asn Pro Glu Thr
1 5 10 15

Leu Glu Arg Val Leu Arg Val Val Arg His Arg Gly Phe His Val Cys
20 25 30

Ser Met Asn Met Ala Ala Ala Ser Asp Ala Gln Asn Ile Asn Ile Glu
35 40 45

Leu Thr Val Ala Ser Pro Arg Ser Val Asp Leu Leu Phe Ser Gln Leu
50 55 60

Asn Lys Leu Val Asp Val Ala His Val Ala Ile Cys Gln Ser Thr Thr
65 70 75 80

Thr Ser Gln Gln Ile Arg Ala
85

<210> SEQ ID NO 31
<211> LENGTH: 1647
<212> TYPE: DNA
<213> ORGANISM: Serratia marcescens
<220> FEATURE:
<223> OTHER INFORMATION: AHAS II, large subunit

<400> SEQUENCE: 31
atgaatggcg ctcagtgggt agttcaagcg ttgcgtgcgc agggtgtgga taccgtattc 60
ggctatccgg gtggggcaat catgccggtg tacgatgcgc tgtacgacgg cggtgtggaa 120
cacctgctgt gtcgccatga acagggcgcc gcgatggccg ccatcggcta cgcccgcgcc 180
accggcaaag tcggcgtttg catcgccact tccggccctg gcgccaccaa cctgatcact 240
ggcctggctg atgcgctgct cgattccgtt cccgttgtcg ccatcaccgg tcaggtgggt 300
tccgcgctga tcggcaccga tgcctttcag gagatcgatg ttctcggcct gtctctggcc 360
tgcaccaagc acagcttcct ggtggaatcg ctggacgcct tgccgggcat catggcggaa 420

```
gcgttcgcca tcgccgcagg cggccgccct ggcccggtgc tgatcgatat cccgaaagac    480
attcagctgg cgcagggcga cttgcacccg catctgatgc cggtcgacga agcgccggcg    540
ttcccggcgg cagcgttggc agaagcggcc gagctgctgg cgcaggccca aaaaccgatg    600
ctgtacgtcg gcggcggcgt gggcatggcg caggcggtgc cggcgctgcg tgaatttatc    660
gccgtgaccc gcatgccgaa cgtcgccacc ctgaaggggc tgggtgcgcc ggatgcgcaa    720
gatccgctgt acctcggcat gttgggcatg cacggcacca aggctgccaa cctggcggtg    780
caggcgtgcg atttgctgat tgccgtcggc gcgcgtttcg atgaccgcgt aaccggcaaa    840
ctgaacgcct tcgcaccgca tgccaaagtg atccacatgg atatcgatcc ggcggagatg    900
agcaagctgc gccaggcgca tgtggccctg cagggcgatc tgaaagcgtt gctgccggcg    960
ttgcagcgcc cgctgaatat cgccgcctgg cagcagcagg tggcggtact gaaagctgag   1020
cacgcctgtc gctacgatca ccccggccag ccgatctacg cgccattgtt cttgcgccag   1080
ctgtccgccc gcaagccggc caacagcgtg gtgaccaccg acgtgggcca gcatcagatg   1140
tggagcgcgc agcacatgac gttcgaacgc ccggagaatt tcatcacctc cagcggcctc   1200
ggcaccatgg ggttcggcgt gccggcggcg gtgggggccc agatcgcgcg cccgcaagat   1260
acggtgatct gcgtctcggg cgatggctcc ttcatgatga acgtacagga gctgggcacc   1320
atcaagcgta aacagctgcc gctcaagatc gtgctgctgg acaaccaacg cctcggaatg   1380
gtgcgtcagt ggcagcagct gttcttcgac ggccgctaca gcgaaaccaa cctgtccgat   1440
aaccccgact tcctgatgct ggccgccgcc ttcggcattc ccggccagcg catcagccgc   1500
aaggatcagg tggaggacgc gctcgaggcg ctgttcaaca ccgaaggccc ttatctgctg   1560
caggtctcta tcgacgaact cgaaaacgtc tggccgctgg tgccgccggg cgccggcaac   1620
gaaaccatgt tggaggaaat atcatga                                       1647
```

<210> SEQ ID NO 32
<211> LENGTH: 548
<212> TYPE: PRT
<213> ORGANISM: Serratia marcescens
<220> FEATURE:
<223> OTHER INFORMATION: AHAS II, large subunit

<400> SEQUENCE: 32

```
Met Asn Gly Ala Gln Trp Val Val Gln Ala Leu Arg Ala Gln Gly Val
1               5                   10                  15

Asp Thr Val Phe Gly Tyr Pro Gly Gly Ala Ile Met Pro Val Tyr Asp
            20                  25                  30

Ala Leu Tyr Asp Gly Gly Val Glu His Leu Leu Cys Arg His Glu Gln
        35                  40                  45

Gly Ala Ala Met Ala Ala Ile Gly Tyr Ala Arg Ala Thr Gly Lys Val
    50                  55                  60

Gly Val Cys Ile Ala Thr Ser Gly Pro Gly Ala Thr Asn Leu Ile Thr
65                  70                  75                  80

Gly Leu Ala Asp Ala Leu Leu Asp Ser Val Pro Val Val Ala Ile Thr
                85                  90                  95

Gly Gln Val Gly Ser Ala Leu Ile Gly Thr Asp Ala Phe Gln Glu Ile
            100                 105                 110

Asp Val Leu Gly Leu Ser Leu Ala Cys Thr Lys His Ser Phe Leu Val
        115                 120                 125

Glu Ser Leu Asp Ala Leu Pro Gly Ile Met Ala Glu Ala Phe Ala Ile
    130                 135                 140
```

```
Ala Ala Gly Gly Arg Pro Gly Pro Val Leu Ile Asp Ile Pro Lys Asp
145                 150                 155                 160

Ile Gln Leu Ala Gln Gly Asp Leu His Pro His Leu Met Pro Val Asp
                165                 170                 175

Glu Ala Pro Ala Phe Pro Ala Ala Ala Leu Ala Glu Ala Ala Glu Leu
            180                 185                 190

Leu Ala Gln Ala Gln Lys Pro Met Leu Tyr Val Gly Gly Gly Val Gly
        195                 200                 205

Met Ala Gln Ala Val Pro Ala Leu Arg Glu Phe Ile Ala Val Thr Arg
    210                 215                 220

Met Pro Asn Val Ala Thr Leu Lys Gly Leu Gly Ala Pro Asp Ala Gln
225                 230                 235                 240

Asp Pro Leu Tyr Leu Gly Met Leu Gly Met His Gly Thr Lys Ala Ala
                245                 250                 255

Asn Leu Ala Val Gln Ala Cys Asp Leu Leu Ile Ala Val Gly Ala Arg
            260                 265                 270

Phe Asp Asp Arg Val Thr Gly Lys Leu Asn Ala Phe Ala Pro His Ala
        275                 280                 285

Lys Val Ile His Met Asp Ile Asp Pro Ala Glu Met Ser Lys Leu Arg
    290                 295                 300

Gln Ala His Val Ala Leu Gln Gly Asp Leu Lys Ala Leu Leu Pro Ala
305                 310                 315                 320

Leu Gln Arg Pro Leu Asn Ile Ala Ala Trp Gln Gln Gln Val Ala Val
                325                 330                 335

Leu Lys Ala Glu His Ala Cys Arg Tyr Asp His Pro Gly Gln Pro Ile
            340                 345                 350

Tyr Ala Pro Leu Phe Leu Arg Gln Leu Ser Ala Arg Lys Pro Ala Asn
        355                 360                 365

Ser Val Val Thr Thr Asp Val Gly Gln His Gln Met Trp Ser Ala Gln
    370                 375                 380

His Met Thr Phe Glu Arg Pro Glu Asn Phe Ile Thr Ser Ser Gly Leu
385                 390                 395                 400

Gly Thr Met Gly Phe Gly Val Pro Ala Ala Val Gly Ala Gln Ile Ala
                405                 410                 415

Arg Pro Gln Asp Thr Val Ile Cys Val Ser Gly Asp Gly Ser Phe Met
            420                 425                 430

Met Asn Val Gln Glu Leu Gly Thr Ile Lys Arg Lys Gln Leu Pro Leu
        435                 440                 445

Lys Ile Val Leu Leu Asp Asn Gln Arg Leu Gly Met Val Arg Gln Trp
    450                 455                 460

Gln Gln Leu Phe Phe Asp Gly Arg Tyr Ser Glu Thr Asn Leu Ser Asp
465                 470                 475                 480

Asn Pro Asp Phe Leu Met Leu Ala Ala Ala Phe Gly Ile Pro Gly Gln
                485                 490                 495

Arg Ile Ser Arg Lys Asp Gln Val Glu Asp Ala Leu Glu Ala Leu Phe
            500                 505                 510

Asn Thr Glu Gly Pro Tyr Leu Leu Gln Val Ser Ile Asp Glu Leu Glu
        515                 520                 525

Asn Val Trp Pro Leu Val Pro Pro Gly Ala Gly Asn Glu Thr Met Leu
    530                 535                 540

Glu Glu Ile Ser
545
```

<210> SEQ ID NO 33
<211> LENGTH: 258
<212> TYPE: DNA
<213> ORGANISM: Serratia marcescens
<220> FEATURE:
<223> OTHER INFORMATION: AHAS II, small subunit

<400> SEQUENCE: 33
atgatgcagc atcaactctc tatccaggcg cgttttcgcc ccgaaatgtt agagcgcgta 60
ttgcgggtcg tgcgtcatcg cggctttcag gtttgtgcta tgaatatggt ttctccggcc 120
aacgccgaca gcatcaatat cgaattgacc gttgccagcc cacgtccggt cgccctgttg 180
tcatctcagt taagcaaact gctggacgtc tcctgcgtcg agatccagca gccaacatca 240
caacaaatac gcgcctga 258

<210> SEQ ID NO 34
<211> LENGTH: 85
<212> TYPE: PRT
<213> ORGANISM: Serratia marcescens
<220> FEATURE:
<223> OTHER INFORMATION: AHAS II, small subunit

<400> SEQUENCE: 34

Met Met Gln His Gln Leu Ser Ile Gln Ala Arg Phe Arg Pro Glu Met
1 5 10 15

Leu Glu Arg Val Leu Arg Val Val Arg His Arg Gly Phe Gln Val Cys
20 25 30

Ala Met Asn Met Val Ser Pro Ala Asn Ala Asp Ser Ile Asn Ile Glu
35 40 45

Leu Thr Val Ala Ser Pro Arg Pro Val Ala Leu Leu Ser Ser Gln Leu
50 55 60

Ser Lys Leu Leu Asp Val Ser Cys Val Glu Ile Gln Gln Pro Thr Ser
65 70 75 80

Gln Gln Ile Arg Ala
85

<210> SEQ ID NO 35
<211> LENGTH: 1725
<212> TYPE: DNA
<213> ORGANISM: Shigella boydii
<220> FEATURE:
<223> OTHER INFORMATION: AHAS III, large subunit

<400> SEQUENCE: 35
atggagatgt tgtctggagc cgagatggtc gtccgatcgc ttatcgatca gggcgttaaa 60
caagtattcg gttatcctgg aggcgcagtc cttgatattt acgatgcatt gcataccgtg 120
ggtggtatcg atcatgtttt agttcgtcat gagcaggcgg cagtgcatat ggccgatggt 180
ctggcgcgcg cgaccgggga agtcggcgtc gtgctggtaa cgtcgggtcc aggggcgacc 240
aatgcgatta ccggcatcgc caccgcttat atggattcca ttccattagt tgtcctttcc 300
gggcaggtag cgacctcgtt gataggttac gatgcctttc aggagtgcga catggtgggg 360
atttcgcgac cagtggttaa acacagtttt ctggttaagc aaacggaaga cattccgcag 420
gtgctgaaaa aggctttctg gctggcggca agtggtcgtc ctggaccagt agtcgttgat 480
ttaccgaaag atattcttaa tccggcgaac aaattaccct atgtctggcc ggagtcggtc 540
agtatgcgtt cttacaatcc cactactacc ggacataaag ggcaaattaa gcgtgctctg 600
caaacgctgg tagtggcaaa aaaaccggtt gtctacgtag gcggtggggc aatcatggcg 660

```
ggctgccatc agcagttgaa agaaacggtg gaggcgttga atctgcccgt tgtttcctca    720

ttgatggggc tgggggcgtt tccggcaacg catcgtcagg cactgggcat gctgggaatg    780

cacggtacct acgaagccaa tatgacgatg cataacgcgg atgtgatttt cgccgtcggg    840

gtacgatttg atgaccgaac gacgaacaat ctggcaaagt actgcccaaa tgccactgtt    900

ctgcatatcg atattgatcc tacttccatt tctaaaaccg tgactgcgga tatcccgatt    960

gtgggggatg ctcgccaggt cctcgaacaa atgcttgaac tcttgtcgca agaatccgcc   1020

catcaaccac tggatgagat ccgcgactgg tggcagcaaa ttgaacagtg gcgcgctcgt   1080

cagtgcctga aatatgacac tcacagtgaa aagattaaac cgcaggcggt gatcgagact   1140

ctttggcggt tgacgaaggg agacgcttac gtgacgtccg atgtcgggca gcaccagatg   1200

tttgctgcac tttattatcc attcgacaaa ccgcgtcgct ggatcaattc cggtggcctc   1260

ggcacgatgg gttttggttt acctgcggca ctgggcgtca aaatggcgtt gccagaagaa   1320

accgtggttt gcgtcactgg cgacggcagt attcagatga acattcagga actgtctacc   1380

gcgttgcaat acgagttgcc cgtactggtg gtgaatctca ataaccgcta tctggggatg   1440

gtgaaacagt ggcaggacat gatctattcc ggccgtcatt cacaatctta tatgcaatca   1500

ctacccgatt tcgtccgtct ggcggaagcc tatggtcacg tcgggatcca gatctctcat   1560

ccgcatgagc tggaaagcaa acttagcgag gcgctggaac aggtgcgcaa taatcgcctg   1620

gtgtttgttg atgttaccgt cgatggcagt gagcacgtct acccgatgca gattcgcggg   1680

ggcggaatgg atgaaatgtg gttaagcaaa acggagagaa cctga                   1725
```

<210> SEQ ID NO 36
<211> LENGTH: 574
<212> TYPE: PRT
<213> ORGANISM: Shigella boydii
<220> FEATURE:
<223> OTHER INFORMATION: AHAS III, large subunit

<400> SEQUENCE: 36

```
Met Glu Met Leu Ser Gly Ala Glu Met Val Val Arg Ser Leu Ile Asp
1               5                   10                  15

Gln Gly Val Lys Gln Val Phe Gly Tyr Pro Gly Gly Ala Val Leu Asp
            20                  25                  30

Ile Tyr Asp Ala Leu His Thr Val Gly Gly Ile Asp His Val Leu Val
        35                  40                  45

Arg His Glu Gln Ala Ala Val His Met Ala Asp Gly Leu Ala Arg Ala
    50                  55                  60

Thr Gly Glu Val Gly Val Val Leu Val Thr Ser Gly Pro Gly Ala Thr
65                  70                  75                  80

Asn Ala Ile Thr Gly Ile Ala Thr Ala Tyr Met Asp Ser Ile Pro Leu
                85                  90                  95

Val Val Leu Ser Gly Gln Val Ala Thr Ser Leu Ile Gly Tyr Asp Ala
            100                 105                 110

Phe Gln Glu Cys Asp Met Val Gly Ile Ser Arg Pro Val Val Lys His
        115                 120                 125

Ser Phe Leu Val Lys Gln Thr Glu Asp Ile Pro Gln Val Leu Lys Lys
    130                 135                 140

Ala Phe Trp Leu Ala Ala Ser Gly Arg Pro Gly Pro Val Val Val Asp
145                 150                 155                 160

Leu Pro Lys Asp Ile Leu Asn Pro Ala Asn Lys Leu Pro Tyr Val Trp
                165                 170                 175
```

```
Pro Glu Ser Val Ser Met Arg Ser Tyr Asn Pro Thr Thr Thr Gly His
            180                 185                 190

Lys Gly Gln Ile Lys Arg Ala Leu Gln Thr Leu Val Val Ala Lys Lys
        195                 200                 205

Pro Val Val Tyr Val Gly Gly Gly Ala Ile Met Ala Gly Cys His Gln
    210                 215                 220

Gln Leu Lys Glu Thr Val Glu Ala Leu Asn Leu Pro Val Val Ser Ser
225                 230                 235                 240

Leu Met Gly Leu Gly Ala Phe Pro Ala Thr His Arg Gln Ala Leu Gly
                245                 250                 255

Met Leu Gly Met His Gly Thr Tyr Glu Ala Asn Met Thr Met His Asn
            260                 265                 270

Ala Asp Val Ile Phe Ala Val Gly Val Arg Phe Asp Asp Arg Thr Thr
        275                 280                 285

Asn Asn Leu Ala Lys Tyr Cys Pro Asn Ala Thr Val Leu His Ile Asp
    290                 295                 300

Ile Asp Pro Thr Ser Ile Ser Lys Thr Val Thr Ala Asp Ile Pro Ile
305                 310                 315                 320

Val Gly Asp Ala Arg Gln Val Leu Glu Gln Met Leu Glu Leu Leu Ser
                325                 330                 335

Gln Glu Ser Ala His Gln Pro Leu Asp Glu Ile Arg Asp Trp Trp Gln
            340                 345                 350

Gln Ile Glu Gln Trp Arg Ala Arg Gln Cys Leu Lys Tyr Asp Thr His
        355                 360                 365

Ser Glu Lys Ile Lys Pro Gln Ala Val Ile Glu Thr Leu Trp Arg Leu
    370                 375                 380

Thr Lys Gly Asp Ala Tyr Val Thr Ser Asp Val Gly Gln His Gln Met
385                 390                 395                 400

Phe Ala Ala Leu Tyr Tyr Pro Phe Asp Lys Pro Arg Arg Trp Ile Asn
                405                 410                 415

Ser Gly Gly Leu Gly Thr Met Gly Phe Gly Leu Pro Ala Ala Leu Gly
            420                 425                 430

Val Lys Met Ala Leu Pro Glu Glu Thr Val Val Cys Val Thr Gly Asp
        435                 440                 445

Gly Ser Ile Gln Met Asn Ile Gln Glu Leu Ser Thr Ala Leu Gln Tyr
    450                 455                 460

Glu Leu Pro Val Leu Val Val Asn Leu Asn Asn Arg Tyr Leu Gly Met
465                 470                 475                 480

Val Lys Gln Trp Gln Asp Met Ile Tyr Ser Gly Arg His Ser Gln Ser
                485                 490                 495

Tyr Met Gln Ser Leu Pro Asp Phe Val Arg Leu Ala Glu Ala Tyr Gly
            500                 505                 510

His Val Gly Ile Gln Ile Ser His Pro His Glu Leu Glu Ser Lys Leu
        515                 520                 525

Ser Glu Ala Leu Glu Gln Val Arg Asn Asn Arg Leu Val Phe Val Asp
    530                 535                 540

Val Thr Val Asp Gly Ser Glu His Val Tyr Pro Met Gln Ile Arg Gly
545                 550                 555                 560

Gly Gly Met Asp Glu Met Trp Leu Ser Lys Thr Glu Arg Thr
                565                 570
```

<210> SEQ ID NO 37
<211> LENGTH: 492

<212> TYPE: DNA
<213> ORGANISM: Shigella boydii
<220> FEATURE:
<223> OTHER INFORMATION: AHAS III, small subunit

<400> SEQUENCE: 37

```
atgcgccgga tattatcagt cttactcgaa aatgaatcag gcgcgttatc ccgcgtgatt     60

ggcctttttt cccagcgagg ctacaacatt gaaagcctga ccgttgcgcc aaccgacgat    120

ccgacattat cgcgtatgac catccagacc gtgggcgatg aaaaagtact tgagcagatc    180

gaaaagcaat tacacaagct ggtcgatgtc ttgcgcgtga gtgagttggg gcagggcgcg    240

catgttgagc gggaaattat gctggtgaaa attcaggcca gcggttacgg gcgtgacgaa    300

gtgaaacgta atacggaaat attccgtggg caaattatcg atgtcacccc ctcgctttat    360

accgttcaat tagcaggcac cagcgataag cttgatgcat ttttagcatc gattcgcgag    420

gtggcgaaaa ttgtggaagt tgctcgctct ggtgtggtcg gactttcgcg cggcgataaa    480

ataatgcgtt ga                                                        492
```

<210> SEQ ID NO 38
<211> LENGTH: 163
<212> TYPE: PRT
<213> ORGANISM: Shigella boydii
<220> FEATURE:
<223> OTHER INFORMATION: AHAS III, small subunit

<400> SEQUENCE: 38

```
Met Arg Arg Ile Leu Ser Val Leu Leu Glu Asn Glu Ser Gly Ala Leu
1               5                   10                  15

Ser Arg Val Ile Gly Leu Phe Ser Gln Arg Gly Tyr Asn Ile Glu Ser
            20                  25                  30

Leu Thr Val Ala Pro Thr Asp Asp Pro Thr Leu Ser Arg Met Thr Ile
        35                  40                  45

Gln Thr Val Gly Asp Glu Lys Val Leu Glu Gln Ile Glu Lys Gln Leu
    50                  55                  60

His Lys Leu Val Asp Val Leu Arg Val Ser Glu Leu Gly Gln Gly Ala
65                  70                  75                  80

His Val Glu Arg Glu Ile Met Leu Val Lys Ile Gln Ala Ser Gly Tyr
                85                  90                  95

Gly Arg Asp Glu Val Lys Arg Asn Thr Glu Ile Phe Arg Gly Gln Ile
            100                 105                 110

Ile Asp Val Thr Pro Ser Leu Tyr Thr Val Gln Leu Ala Gly Thr Ser
        115                 120                 125

Asp Lys Leu Asp Ala Phe Leu Ala Ser Ile Arg Glu Val Ala Lys Ile
    130                 135                 140

Val Glu Val Ala Arg Ser Gly Val Val Gly Leu Ser Arg Gly Asp Lys
145                 150                 155                 160

Ile Met Arg
```

<210> SEQ ID NO 39
<211> LENGTH: 1719
<212> TYPE: DNA
<213> ORGANISM: Serratia marcescens
<220> FEATURE:
<223> OTHER INFORMATION: AHAS III, large subunit

<400> SEQUENCE: 39

```
atggagatgt tgtcaggagc cgagatggtc gtccgatcgt tgatcgatca gggcgttaaa     60
```

```
catgtattcg gctaccccgg cggggcggtg ctcgatatct acgacgccct gcatacggtc    120

ggagggatcg atcatattct ggtgcgccac gagcaaggtg cggtgcacat ggccgacggt    180

tacgcgcgcg ccaccggcga agtgggcgtg gtgctggtga cgtccggccc cggcgccacc    240

aacgccatta ccggtatcgc taccgcttat atggactcga tcccgatggt cgtcctgtcg    300

gggcaggtgc ccagctcgct gatcggctac gacgcctttc aggagtgcga tatggtgggg    360

atttctcggc cggtggtgaa acacagcttc ctggtaaaac gcaccgaaga catcccggcg    420

gtgttgaaga aggcctttta cctggcctcc agcggccgcc ccggcccggt ggtgatcgat    480

ctgccgaaag acatcgtcgg cccggcggtg cggatgcctt atgcctaccc gcaggacgtg    540

agcatgcgtt cttataaccc gacggtgcag ggccatcgcg ggcaaatcaa acgcgcgttg    600

caaaccatcc tggcggccaa gaagccggtg atgtatgtcg gcggcggcgc gatcaacgcc    660

ggttgcgaag ccgaactgct ggcgttggcg gagcagctga acctgccggt gaccagcagc    720

ctgatgggac tgggcgcttt ccccggcacc catcgccaga gtgtcggcat gctcggtatg    780

cacggcactt atgaagccaa caaaaccatg caccatgccg acgtgatctt cgcggtcggc    840

gtgcgtttcg acgatcgcac gaccaacaat ctggccaaat actgcccgga tgccaccgtg    900

ctgcatatcg atatcgatcc gacctcgatc tccaaaacgg tggatgccga tattccgatc    960

gtcggcgatg ccaaacaggt gttggtgcag atgctggagc tgttggcgca ggatgacaag   1020

gcgcaggatc acgatgcgtt gcgcgattgg tggcagtcta ttgaacagtg gcgcgcccgc   1080

gactgtttgg ggtacgacaa aaacagcggc accatcaagc cgcaggcggt gatcgaaacc   1140

ctgcatcgcc tgaccaaagg cgatgcctat gtgacctccg acgtggggca gcaccagatg   1200

tttgccgcgc tctattaccc gttcgacaaa ccgcgccgtt ggatcaactc cggcggcctc   1260

ggcaccatgg gcttcggcct gccggcggca ttgggcgtca agctggcgct gccggaggaa   1320

accgtggtgt gcgtcaccgg cgacggcagc atccagatga acattcagga gctgtccacc   1380

gcgctgcaat ataacctgcc ggtggtggtg gtgaacctca acaaccgcta tctgggcatg   1440

gtcaagcagt ggcaggacat gatttattcc ggccgccact cgcagtctta catggattcg   1500

ctgccggact ttgtcaagct ggccgaggct tacggccatg tcggcatcgc catccgcacg   1560

ccggatgagc tggaaagcaa gctggcgcag gcgctggcgg aaaaagagcg gctggtgttc   1620

gtcgacgtga ccgtcgatga aaccgaacat gtttacccga tgcagatccg cggcggaagc   1680

atggacgaaa tgtggcttag caaaacggag aggacctga                          1719
```

<210> SEQ ID NO 40
<211> LENGTH: 572
<212> TYPE: PRT
<213> ORGANISM: Serratia marcescens
<220> FEATURE:
<223> OTHER INFORMATION: AHAS III, largeV subunit

<400> SEQUENCE: 40

```
Met Glu Met Leu Ser Gly Ala Glu Met Val Val Arg Ser Leu Ile Asp
1               5                   10                  15

Gln Gly Val Lys His Val Phe Gly Tyr Pro Gly Gly Ala Val Leu Asp
            20                  25                  30

Ile Tyr Asp Ala Leu His Thr Val Gly Gly Ile Asp His Ile Leu Val
        35                  40                  45

Arg His Glu Gln Gly Ala Val His Met Ala Asp Gly Tyr Ala Arg Ala
    50                  55                  60

Thr Gly Glu Val Gly Val Val Leu Val Thr Ser Gly Pro Gly Ala Thr
```

-continued

```
65                  70                  75                  80

Asn Ala Ile Thr Gly Ile Ala Thr Ala Tyr Met Asp Ser Ile Pro Met
                85                  90                  95

Val Val Leu Ser Gly Gln Val Pro Ser Ser Leu Ile Gly Tyr Asp Ala
            100                 105                 110

Phe Gln Glu Cys Asp Met Val Gly Ile Ser Arg Pro Val Val Lys His
        115                 120                 125

Ser Phe Leu Val Lys Arg Thr Glu Asp Ile Pro Ala Val Leu Lys Lys
    130                 135                 140

Ala Phe Tyr Leu Ala Ser Ser Gly Arg Pro Gly Pro Val Val Ile Asp
145                 150                 155                 160

Leu Pro Lys Asp Ile Val Gly Pro Ala Val Arg Met Pro Tyr Ala Tyr
                165                 170                 175

Pro Gln Asp Val Ser Met Arg Ser Tyr Asn Pro Thr Val Gln Gly His
            180                 185                 190

Arg Gly Gln Ile Lys Arg Ala Leu Gln Thr Ile Leu Ala Ala Lys Lys
        195                 200                 205

Pro Val Met Tyr Val Gly Gly Gly Ala Ile Asn Ala Gly Cys Glu Ala
    210                 215                 220

Glu Leu Leu Ala Leu Ala Glu Gln Leu Asn Leu Pro Val Thr Ser Ser
225                 230                 235                 240

Leu Met Gly Leu Gly Ala Phe Pro Gly Thr His Arg Gln Ser Val Gly
                245                 250                 255

Met Leu Gly Met His Gly Thr Tyr Glu Ala Asn Lys Thr Met His His
            260                 265                 270

Ala Asp Val Ile Phe Ala Val Gly Val Arg Phe Asp Asp Arg Thr Thr
        275                 280                 285

Asn Asn Leu Ala Lys Tyr Cys Pro Asp Ala Thr Val Leu His Ile Asp
    290                 295                 300

Ile Asp Pro Thr Ser Ile Ser Lys Thr Val Asp Ala Asp Ile Pro Ile
305                 310                 315                 320

Val Gly Asp Ala Lys Gln Val Leu Val Gln Met Leu Glu Leu Leu Ala
                325                 330                 335

Gln Asp Asp Lys Ala Gln Asp His Asp Ala Leu Arg Asp Trp Trp Gln
            340                 345                 350

Ser Ile Glu Gln Trp Arg Ala Arg Asp Cys Leu Gly Tyr Asp Lys Asn
        355                 360                 365

Ser Gly Thr Ile Lys Pro Gln Ala Val Ile Glu Thr Leu His Arg Leu
    370                 375                 380

Thr Lys Gly Asp Ala Tyr Val Thr Ser Asp Val Gly Gln His Gln Met
385                 390                 395                 400

Phe Ala Ala Leu Tyr Tyr Pro Phe Asp Lys Pro Arg Arg Trp Ile Asn
                405                 410                 415

Ser Gly Gly Leu Gly Thr Met Gly Phe Gly Leu Pro Ala Ala Leu Gly
            420                 425                 430

Val Lys Leu Ala Leu Pro Glu Glu Thr Val Val Cys Val Thr Gly Asp
        435                 440                 445

Gly Ser Ile Gln Met Asn Ile Gln Glu Leu Ser Thr Ala Leu Gln Tyr
    450                 455                 460

Asn Leu Pro Val Val Val Val Asn Leu Asn Asn Arg Tyr Leu Gly Met
465                 470                 475                 480

Val Lys Gln Trp Gln Asp Met Ile Tyr Ser Gly Arg His Ser Gln Ser
                485                 490                 495
```

```
Tyr Met Asp Ser Leu Pro Asp Phe Val Lys Leu Ala Glu Ala Tyr Gly
            500                 505                 510

His Val Gly Ile Ala Ile Arg Thr Pro Asp Glu Leu Glu Ser Lys Leu
        515                 520                 525

Ala Gln Ala Leu Ala Glu Lys Glu Arg Leu Val Phe Val Asp Val Thr
    530                 535                 540

Val Asp Glu Thr Glu His Val Tyr Pro Met Gln Ile Arg Gly Gly Ser
545                 550                 555                 560

Met Asp Glu Met Trp Leu Ser Lys Thr Glu Arg Thr
                565                 570


<210> SEQ ID NO 41
<211> LENGTH: 495
<212> TYPE: DNA
<213> ORGANISM: Serratia marcescens
<220> FEATURE:
<223> OTHER INFORMATION: AHAS III, small subunit

<400> SEQUENCE: 41

atcatgcgcc gtattttatc tgtcttgctg gaaaacgaat ccggcgccct ctcgcgcgtg      60

gtggggttgt tctcccagcg tggttataac attgagagcc tgacggtggc gccgaccgac     120

gatccgacgc tgtcgcgtat gactatccag accgtcggcg acgagaaagt gctggagcag     180

attgagaagc agttgcacaa gctggtggac gtgctgcgcg tcagcgagct ggtgcagggc     240

gctcacgtcg agcgcgagat catgctggtg aaactgcagg ccagcggcta cggccgtgaa     300

gaggtgaagc gctgcgccga cattttccgc ggccagatcg tcgatgtgac ggcgacgttg     360

tatacggtgc agttggccgg caccagcgat aaactggacg ccttcctgag tgcggtgcga     420

gacgtcgcgg agatcgtgga agtggcgcgt tccggcgtgg tcggcgtgtc gcgcggcgac     480

aaaatcatgc gctga                                                      495


<210> SEQ ID NO 42
<211> LENGTH: 164
<212> TYPE: PRT
<213> ORGANISM: Serratia marcescens
<220> FEATURE:
<223> OTHER INFORMATION: AHAS III, small subunit

<400> SEQUENCE: 42

Met Met Arg Arg Ile Leu Ser Val Leu Leu Glu Asn Glu Ser Gly Ala
1               5                   10                  15

Leu Ser Arg Val Val Gly Leu Phe Ser Gln Arg Gly Tyr Asn Ile Glu
            20                  25                  30

Ser Leu Thr Val Ala Pro Thr Asp Asp Pro Thr Leu Ser Arg Met Thr
        35                  40                  45

Ile Gln Thr Val Gly Asp Glu Lys Val Leu Glu Gln Ile Glu Lys Gln
    50                  55                  60

Leu His Lys Leu Val Asp Val Leu Arg Val Ser Glu Leu Val Gln Gly
65                  70                  75                  80

Ala His Val Glu Arg Glu Ile Met Leu Val Lys Leu Gln Ala Ser Gly
                85                  90                  95

Tyr Gly Arg Glu Glu Val Lys Arg Cys Ala Asp Ile Phe Arg Gly Gln
            100                 105                 110

Ile Val Asp Val Thr Ala Thr Leu Tyr Thr Val Gln Leu Ala Gly Thr
        115                 120                 125

Ser Asp Lys Leu Asp Ala Phe Leu Ser Ala Val Arg Asp Val Ala Glu
```

-continued

```
130                 135                 140

Ile Val Glu Val Ala Arg Ser Gly Val Val Gly Val Ser Arg Gly Asp
145                 150                 155                 160

Lys Ile Met Arg


<210> SEQ ID NO 43
<211> LENGTH: 1725
<212> TYPE: DNA
<213> ORGANISM: Bacillus subtilis
<220> FEATURE:
<223> OTHER INFORMATION: AHAS III, large subunit

<400> SEQUENCE: 43

atggggacta atgtacaggt ggattcagca tctgccgaat gtacacagac gatgagcgga      60

gcattaatgc tgattgaatc attaaaaaaa gagaaagtag aaatgatctt cggttatccg     120

ggcggggctg tgcttccgat ttacgataag ctatacaatt cagggttggt acatatcctt     180

ccccgtcacg aacaaggagc aattcatgca gcggagggat acgcaagggt ctccggaaaa     240

ccgggtgtcg tcattgccac gtcagggccg ggagcgacaa accttgttac aggccttgct     300

gatgccatga ttgattcatt gccgttagtc gtctttacag ggcaggtagc aacctctgta     360

atcgggagcg atgcatttca ggaagcagac attttaggga ttacgatgcc agtaacaaaa     420

cacagctacc aggttcgcca gccggaagat ctgccgcgca tcattaaaga agcgttccat     480

attgcaacaa ctggaagacc cggacctgta ttgattgata ttccgaaaga tgtagcaaca     540

attgaaggag aattcagcta cgatcatgag atgaatctcc cgggatacca gccgacaaca     600

gagccgaatt atttgcagat ccgcaagctt gtggaagccg tgagcagtgc gaaaaaaccg     660

gtgatcctgg cgggtgcggg cgtactgcac ggaaaagcgt cagaagaatt aaaaaattat     720

gctgaacagc agcaaatccc tgtggcacac accctttttgg ggctcggagg cttcccggct     780

gaccatccgc ttttcctagg gatggcggga atgcacggta cttatacagc caatatggcc     840

cttcatgaat gtgatctatt aatcagtatc ggcgcccgtt ttgatgaccg tgtcacagga     900

aacctgaaac actttgccag aaacgcaaag atagcccaca tcgatattga tccagctgaa     960

atcggaaaaa tcatgaaaac acagattcct gtagtcggag acagcaaaat tgtcctgcag    1020

gagctgatca aacaagacgg caaacaaagc gattcaagcg aatggaaaaa acagctcgca    1080

gaatggaaag aagagtatcc gctctggtat gtagataatg aagaagaagg ttttaaacct    1140

cagaaattga ttgaatatat tcatcaattt acaaaaggag aggccattgt cgcaacggat    1200

gtaggccagc atcaaatgtg gtcagcgcaa ttttatccgt tccaaaaagc agataaatgg    1260

gtcacgtcag gcggacttgg aacgatggga ttcggtcttc cggcggcgat cggcgcacag    1320

ctggccgaaa aagatgctac tgttgtcgcg gttgtcggag acggcggatt ccaaatgacg    1380

cttcaagaac tcgatgttat tcgcgaatta aatcttccgg tcaaggtagt gattttaaat    1440

aacgcttgtc tcggaatggt cagacagtgg caggaaattt tctatgaaga acgttattca    1500

gaatctaaat tcgcttctca gcctgacttc gtcaaattgt ccgaagcata cggcattaaa    1560

ggcatcagaa tttcatcaga agcggaagca aaggaaaagc tggaagaggc attaacatca    1620

agagaacctg ttgtcattga cgtgcgggtt gccagcgaag aaaaagtatt cccgatggtg    1680

gctccgggga aagggctgca tgaaatggtg gggtgaaac cttga                    1725


<210> SEQ ID NO 44
<211> LENGTH: 574
<212> TYPE: PRT
```

```
<213> ORGANISM: Bacillus subtilis
<220> FEATURE:
<223> OTHER INFORMATION: AHAS III, large subunit

<400> SEQUENCE: 44

Met Gly Thr Asn Val Gln Val Asp Ser Ala Ser Ala Glu Cys Thr Gln
1               5                   10                  15

Thr Met Ser Gly Ala Leu Met Leu Ile Glu Ser Leu Lys Lys Glu Lys
            20                  25                  30

Val Glu Met Ile Phe Gly Tyr Pro Gly Gly Ala Val Leu Pro Ile Tyr
        35                  40                  45

Asp Lys Leu Tyr Asn Ser Gly Leu Val His Ile Leu Pro Arg His Glu
    50                  55                  60

Gln Gly Ala Ile His Ala Ala Glu Gly Tyr Ala Arg Val Ser Gly Lys
65                  70                  75                  80

Pro Gly Val Val Ile Ala Thr Ser Gly Pro Gly Ala Thr Asn Leu Val
                85                  90                  95

Thr Gly Leu Ala Asp Ala Met Ile Asp Ser Leu Pro Leu Val Val Phe
            100                 105                 110

Thr Gly Gln Val Ala Thr Ser Val Ile Gly Ser Asp Ala Phe Gln Glu
        115                 120                 125

Ala Asp Ile Leu Gly Ile Thr Met Pro Val Thr Lys His Ser Tyr Gln
    130                 135                 140

Val Arg Gln Pro Glu Asp Leu Pro Arg Ile Ile Lys Glu Ala Phe His
145                 150                 155                 160

Ile Ala Thr Thr Gly Arg Pro Gly Pro Val Leu Ile Asp Ile Pro Lys
                165                 170                 175

Asp Val Ala Thr Ile Glu Gly Glu Phe Ser Tyr Asp His Glu Met Asn
            180                 185                 190

Leu Pro Gly Tyr Gln Pro Thr Thr Glu Pro Asn Tyr Leu Gln Ile Arg
        195                 200                 205

Lys Leu Val Glu Ala Val Ser Ser Ala Lys Lys Pro Val Ile Leu Ala
    210                 215                 220

Gly Ala Gly Val Leu His Gly Lys Ala Ser Glu Glu Leu Lys Asn Tyr
225                 230                 235                 240

Ala Glu Gln Gln Gln Ile Pro Val Ala His Thr Leu Leu Gly Leu Gly
                245                 250                 255

Gly Phe Pro Ala Asp His Pro Leu Phe Leu Gly Met Ala Gly Met His
            260                 265                 270

Gly Thr Tyr Thr Ala Asn Met Ala Leu His Glu Cys Asp Leu Leu Ile
        275                 280                 285

Ser Ile Gly Ala Arg Phe Asp Asp Arg Val Thr Gly Asn Leu Lys His
    290                 295                 300

Phe Ala Arg Asn Ala Lys Ile Ala His Ile Asp Ile Asp Pro Ala Glu
305                 310                 315                 320

Ile Gly Lys Ile Met Lys Thr Gln Ile Pro Val Val Gly Asp Ser Lys
                325                 330                 335

Ile Val Leu Gln Glu Leu Ile Lys Gln Asp Gly Lys Gln Ser Asp Ser
            340                 345                 350

Ser Glu Trp Lys Lys Gln Leu Ala Glu Trp Lys Glu Glu Tyr Pro Leu
        355                 360                 365

Trp Tyr Val Asp Asn Glu Glu Glu Gly Phe Lys Pro Gln Lys Leu Ile
    370                 375                 380

Glu Tyr Ile His Gln Phe Thr Lys Gly Glu Ala Ile Val Ala Thr Asp
```

```
385                 390                 395                 400

Val Gly Gln His Gln Met Trp Ser Ala Gln Phe Tyr Pro Phe Gln Lys
                405                 410                 415

Ala Asp Lys Trp Val Thr Ser Gly Gly Leu Gly Thr Met Gly Phe Gly
            420                 425                 430

Leu Pro Ala Ala Ile Gly Ala Gln Leu Ala Glu Lys Asp Ala Thr Val
        435                 440                 445

Val Ala Val Val Gly Asp Gly Gly Phe Gln Met Thr Leu Gln Glu Leu
    450                 455                 460

Asp Val Ile Arg Glu Leu Asn Leu Pro Val Lys Val Val Ile Leu Asn
465                 470                 475                 480

Asn Ala Cys Leu Gly Met Val Arg Gln Trp Gln Glu Ile Phe Tyr Glu
                485                 490                 495

Glu Arg Tyr Ser Glu Ser Lys Phe Ala Ser Gln Pro Asp Phe Val Lys
            500                 505                 510

Leu Ser Glu Ala Tyr Gly Ile Lys Gly Ile Arg Ile Ser Ser Glu Ala
        515                 520                 525

Glu Ala Lys Glu Lys Leu Glu Glu Ala Leu Thr Ser Arg Glu Pro Val
    530                 535                 540

Val Ile Asp Val Arg Val Ala Ser Glu Glu Lys Val Phe Pro Met Val
545                 550                 555                 560

Ala Pro Gly Lys Gly Leu His Glu Met Val Gly Val Lys Pro
                565                 570
```

<210> SEQ ID NO 45
<211> LENGTH: 519
<212> TYPE: DNA
<213> ORGANISM: Bacillus subtilis
<220> FEATURE:
<223> OTHER INFORMATION: AHAS III, small subunit

<400> SEQUENCE: 45

```
ttgaaaagaa ttatcacatt gactgtggtg aaccgctccg ggtgttaaa ccggatcacc      60

ggtctattca caaaaaggca ttacaacatt gaaagcatta cagttggaca cacagaaaca    120

gccggcgttt ccagaatcac cttcgtcgtt catgttgaag gtgaaaatga tgttgaacag    180

ttaacgaaac agctcaacaa acagattgat gtgctgaaag tcacagacat cacaaatcaa    240

tcgattgtcc agagggagct ggccttaatc aaggttgtct ccgcaccttc aacaagaaca    300

gagattaatg gaatcataga accgtttaga gcctctgtcg ttgatgtcag cagagacagc    360

atcgttgttc aggtgacagg tgaatctaac aaaattgaag cgcttattga gttattaaaa    420

ccttatggca ttaaagaaat cgcgagaaca ggtacaacgg cttttgcgag gggaacccag    480

caaaaggcgt catccaataa aacaatatct attgtataa                           519
```

<210> SEQ ID NO 46
<211> LENGTH: 172
<212> TYPE: PRT
<213> ORGANISM: Bacillus subtilis
<220> FEATURE:
<223> OTHER INFORMATION: AHAS III, small subunit

<400> SEQUENCE: 46

```
Met Lys Arg Ile Ile Thr Leu Thr Val Val Asn Arg Ser Gly Val Leu
1               5                   10                  15

Asn Arg Ile Thr Gly Leu Phe Thr Lys Arg His Tyr Asn Ile Glu Ser
            20                  25                  30
```

-continued

```
Ile Thr Val Gly His Thr Glu Thr Ala Gly Val Ser Arg Ile Thr Phe
        35                  40                  45

Val Val His Val Glu Gly Glu Asn Asp Val Glu Gln Leu Thr Lys Gln
    50                  55                  60

Leu Asn Lys Gln Ile Asp Val Leu Lys Val Thr Asp Ile Thr Asn Gln
65                  70                  75                  80

Ser Ile Val Gln Arg Glu Leu Ala Leu Ile Lys Val Val Ser Ala Pro
                85                  90                  95

Ser Thr Arg Thr Glu Ile Asn Gly Ile Ile Glu Pro Phe Arg Ala Ser
            100                 105                 110

Val Val Asp Val Ser Arg Asp Ser Ile Val Val Gln Val Thr Gly Glu
        115                 120                 125

Ser Asn Lys Ile Glu Ala Leu Ile Glu Leu Leu Lys Pro Tyr Gly Ile
    130                 135                 140

Lys Glu Ile Ala Arg Thr Gly Thr Thr Ala Phe Ala Arg Gly Thr Gln
145                 150                 155                 160

Gln Lys Ala Ser Ser Asn Lys Thr Ile Ser Ile Val
                165                 170
```